(12) United States Patent
Park et al.

(10) Patent No.: US 10,914,665 B2
(45) Date of Patent: Feb. 9, 2021

(54) APPARATUS FOR DETECTING SAMPLE PROPERTIES USING CHAOTIC WAVE SENSOR

(71) Applicants: Korea Advanced Institute of Science and Technology, Daejeon (KR); The Wave Talk, Inc., Daejeon (KR)

(72) Inventors: YongKeun Park, Daejeon (KR); JongHee Yoon, Daejeon (KR); Kyeoreh Lee, Daejeon (KR); Young Dug Kim, Gyeonggi-do (KR); Nam Kyun Kim, Gyeonggi-do (KR)

(73) Assignees: Korea Advanced Institute of Science and Technology, Daejeon (KR); The Wave Talk, Inc., Daejeon (KR)

( * ) Notice: Subject to any disclaimer, the term of this patent is extended or adjusted under 35 U.S.C. 154(b) by 0 days.

(21) Appl. No.: 16/697,373

(22) Filed: Nov. 27, 2019

(65) Prior Publication Data

US 2020/0116618 A1 Apr. 16, 2020

Related U.S. Application Data

(63) Continuation of application No. 15/776,584, filed as application No. PCT/KR2016/013288 on Nov. 17, (Continued)

(30) Foreign Application Priority Data

Nov. 17, 2015 (KR) .......................... 10-2015-0160915
Mar. 10, 2016 (KR) .......................... 10-2016-0028966
(Continued)

(51) Int. Cl.
*G01N 15/06* (2006.01)
*C12Q 1/18* (2006.01)
(Continued)

(52) U.S. Cl.
CPC .............. *G01N 15/06* (2013.01); *C12Q 1/18* (2013.01); *G01N 33/483* (2013.01);
(Continued)

(58) Field of Classification Search
CPC ............. G01N 21/45; G01N 2021/479; G01N 21/4788; G01N 21/49; G01N 2201/06113;
(Continued)

(56) References Cited

U.S. PATENT DOCUMENTS 4,676,951 A * 6/1987 Armes .................. G01N 35/00
222/136
4,985,205 A * 1/1991 Fritsche ............. G01N 21/8483
356/408

(Continued)

FOREIGN PATENT DOCUMENTS

CN 101271156 A 9/2008
CN 102565002 A 7/2012
(Continued)

OTHER PUBLICATIONS

Bin Zheng et al. "Feature Information Extraction From Dynamic Biospeckle" Applied Optics, vol. 33, No. 2, (Jan. 10, 1994), pp. 231-237.
(Continued)

*Primary Examiner* — Michael P Stafira
(74) *Attorney, Agent, or Firm* — Harrington & Smith

(57) ABSTRACT

Provided is a sample property detecting apparatus including: a wave source configured to irradiate a wave towards a sample; a detector configured to detect a laser speckle that is generated when the wave is multiple-scattered by the sample, at every time point that is set in advance; and a controller configured to obtain a temporal correlation that is a variation in the detected laser speckle according to time,
(Continued)

and to detect properties of the sample in real-time based on the temporal correlation, wherein the detector detects the laser speckle between the sample and the detector or from a region in the detector.

7 Claims, 55 Drawing Sheets

Related U.S. Application Data 2016, now Pat. No. 10,551,293, which is a continuation-in-part of application No. 15/170,508, filed on Jun. 1, 2016, now Pat. No. 10,001,467.

(30) Foreign Application Priority Data

| Jun. 2, 2016 | (KR) | 10-2016-0068563 |
|---|---|---|
| Jun. 3, 2016 | (EP) | 16172885 |
| Jul. 18, 2016 | (KR) | 10-2016-0090961 |
| Jul. 21, 2016 | (KR) | 10-2016-0092901 |
| Jul. 22, 2016 | (KR) | 10-2016-0093466 |
| Sep. 21, 2016 | (KR) | 10-2016-0120764 |
| Oct. 12, 2016 | (KR) | 10-2016-0132149 |
| Oct. 12, 2016 | (KR) | 10-2016-0132150 |
| Nov. 1, 2016 | (KR) | 10-2016-0144640 |
| Nov. 16, 2016 | (KR) | 10-2016-0152973 |

(51) Int. Cl.
*G01N 33/483* (2006.01)
*G01N 15/00* (2006.01)

(52) U.S. Cl.
CPC .......... *G01N 2015/0065* (2013.01); *G01N 2015/0687* (2013.01); *G01N 2015/0693* (2013.01)

(58) Field of Classification Search
CPC .......... G01N 15/1434; G01N 21/47; G01N 21/4795; G01N 29/2418; G01N 15/0211; G01N 2015/0065; G01N 2015/0222; G01N 2021/1706; G01N 2021/3129; G01N 21/1702; G01N 21/4738; G01N 21/51; G01N 21/7746; G01N 21/85; G01N 21/95623; G01N 15/06; G01N 15/10; G01N 15/1429; G01N 15/1463; G01N 2015/0038; G01N 2015/0687; G01N 2015/0693; G01N 2015/1087; G01N 2015/1093; G01N 2015/1454; G01N 2021/458; G01N 21/21; G01N 21/95607; G01N 21/958; G01N 2201/0683; G01N 2201/08; G01N 33/483; G01N 33/54373; G01N 15/0227; G01N 2021/4735; G01N 2021/4792; G01N 2021/655; G01N 21/33; G01N 21/3563; G01N 24/455; G01N 21/474; G01N 21/53; G01N 21/84; G01N 21/8901; G01N 21/94; G01N 21/954; G01N 2201/0221; G01N 2201/0634; G01N 2201/0636; G01N 2201/0638; G01N 2201/066; G01N 2201/0668; G01N 2201/1244; G01N 2291/014; G01N 2291/2695; G01N 29/12; G01N 33/0027; G01N 33/4905; G01N 33/5011; G02B 27/48; G02B 6/02; G02B 6/028; G02B 6/0281; G02B 6/0283; G02B 6/0285; G02B 6/0286; G02B 6/0288; G02B 6/421; G02B 13/22; G02B 2027/0105; G02B 2027/0138; G02B 2027/0174; G02B 2027/0187; G02B 27/017; G02B 27/0172; G02B 21/0056; G02B 21/04; G02B 21/125; G02B 21/16; G02B 21/24; G02B 21/26; G02B 21/28; G02B 21/361; G02B 21/362; G02B 26/06; G02B 27/0006; G02B 27/42; G01B 11/002; G01B 9/02094; G01B 9/02002; G01B 9/0201; G01B 9/02031; G01B 9/02091; G01B 11/007; G01B 11/03; G01B 11/162; G01B 11/303; G01B 5/012; G01B 11/02; G01B 11/043; G01B 11/22; G01B 11/25; G01B 11/30; G01B 9/02004; G01B 9/02027; G01B 9/02028; G01B 9/02032; G01B 9/02095; G01J 1/0425; G01J 1/44; G01J 2001/442; G01J 2001/4466; G01J 2001/448; G01J 3/32; G01J 3/42

See application file for complete search history.

(56) References Cited

U.S. PATENT DOCUMENTS

| 6,076,010 | A | 6/2000 | Boas et al. |
|---|---|---|---|
| 7,231,243 | B2* | 6/2007 | Tearney ............ A61B 1/00082 |
| | | | 600/407 |
| 7,310,139 | B2 | 12/2007 | Takai et al. |
| 7,418,169 | B2 | 8/2008 | Tearney |
| 7,746,453 | B2 | 6/2010 | Nishiyama et al. |
| 8,400,494 | B2 | 3/2013 | Zalevsky |
| 9,915,813 | B2 | 3/2018 | Olesen et al. |
| 2004/0070756 | A1 | 4/2004 | Rastopov |
| 2006/0066850 | A1* | 3/2006 | Kimura .................... G01J 3/10 |
| | | | 356/328 |
| 2008/0106737 | A1 | 5/2008 | Weichselbaum et al. |
| 2008/0231514 | A1 | 9/2008 | Matsuura et al. ............ 342/453 |
| 2008/0242557 | A1 | 10/2008 | Kim et al. |
| 2009/0115996 | A1* | 5/2009 | Serebrennikova ..... G01N 21/31 |
| | | | 356/39 |
| 2009/0118622 | A1 | 5/2009 | Durkin |
| 2009/0122312 | A1* | 5/2009 | Reddy ................ G01N 21/3504 |
| | | | 356/321 |
| 2009/0242799 | A1* | 10/2009 | Bolotin ............. G01N 15/1459 |
| | | | 250/459.1 |
| 2010/0277734 | A1 | 11/2010 | Weichselbaum et al. |
| 2010/0331672 | A1* | 12/2010 | Nolte ................. G01B 9/02082 |
| | | | 600/425 |
| 2012/0022381 | A1 | 1/2012 | Tearney et al. |
| 2012/0130253 | A1 | 5/2012 | Nadkarni et al. |
| 2014/0178865 | A1 | 6/2014 | Reed et al. |
| 2015/0098126 | A1* | 4/2015 | Keller ................ G02B 21/0076 |
| | | | 359/385 |
| 2015/0226733 | A1 | 8/2015 | Verschuren et al. |
| 2015/0276571 | A1 | 10/2015 | Hajjarian et al. |
| 2016/0289729 | A1* | 10/2016 | Richards .................. G02B 7/28 |
| 2017/0023599 | A1* | 1/2017 | Richards ............. C12Q 1/6841 |
| 2018/0123314 | A1* | 5/2018 | Hunter, Jr. ............. H01S 3/305 |
| 2018/0143418 | A1* | 5/2018 | Kapanidis ............. G02B 21/28 |

FOREIGN PATENT DOCUMENTS

| CN | 202394176 U | 8/2012 |
|---|---|---|
| CN | 103063145 A | 4/2013 |
| CN | 103759651 A | 4/2014 |
| CN | 103983340 A | 8/2014 |
| JP | 2006-515420 A | 5/2006 |
| JP | 2008275540 A | 11/2008 |
| JP | 2015121552 A | 7/2015 |
| KR | 20040094817 A | 11/2004 |
| KR | 10-2012-0089769 A | 8/2012 |
| KR | 10-2013-0001739 A | 1/2013 |
| KR | 20140058589 A | 5/2014 |

(56) References Cited

FOREIGN PATENT DOCUMENTS

| KR | 10-2014-0109158 A | 9/2014 |
| KR | 10-2015-0050265 A | 5/2015 |
| KR | 10-2016-0109901 A | 9/2016 |

OTHER PUBLICATIONS

Vincitorio F M et al. "Dynamic Speckle Study of Microbial Growth", Visual Communications and Image processing; Jan. 20, 2004 vol. 9660, (Aug. 23, 2015), pp. 96601Q1-6.

Andre V Saude et al. "On Generalized Differences for Biospeckle Image Analysis" Graphic, Patterns and images, 2010 $23^{rd}$ SIBGRAPI, IEEE, (Aug. 30, 2010), pp. 209-215.

Ramirez-Miquet, Evelio E., et al., "*Escherichia coli* Activity Characterization Using a Laser Dynamic Speckle Technique", Revista Cubana De Fisica, vol. 28, No. 1E, Dec. 2011, 5 pgs.

\* cited by examiner

| LIGHT SCATTERED BY MEASUREMENT TARGET | CONTROL LIGHT WAVEFRONT | INTEGRATE (LENS) | DETECT RECONSTRUCTED LIGHT |

--- SCANNING PATH OF WAVE

APPARATUS FOR DETECTING SAMPLE PROPERTIES USING CHAOTIC WAVE SENSOR

RELATED APPLICATION

This application is a continuation of U.S. patent application Ser. No. 15/776,584, filed May 16, 2018, which is incorporated herein by reference in its entirety.

TECHNICAL FIELD

The present disclosure relates to an apparatus for detecting sample properties by using a chaotic wave sensor.

BACKGROUND ART

Human beings coexist with other lives. Invisible lives, as well as visible lives, coexist with human beings, and directly/indirectly affect human lives. Among them, microbes or fine lives affecting health states of the human beings are not visible to human eyes, but exist around human beings and trigger various illnesses.

In order to measure invisible microbes, a microbe cultivation method, a mass spectrometry method, an unclear magnetic resonance method, etc. is used according to the related art. When the microbe cultivation method, the mass spectrometry method, and the unclear magnetic resonance method are used, it takes a long time period to cultivate bacteria and precise and complicated equipment of high expenses is necessary.

Alternately, a method of measuring microbes by using an optical method may be used. For example, a Raman spectrometry or a multispectral imaging method may be used as the optical method, but a complicated optical system is necessary, professional knowledge about the complicated optical system and equipment of laboratory level are also necessary, and measurement takes a long time period. Thus, it may be difficult for the general public to access the system.

DESCRIPTION OF EMBODIMENTS

Technical Problem

Provided is an apparatus of detecting sample properties by using a chaotic wave sensor.

Solution to Problem

According to an aspect of the present disclosure, a sample property detecting apparatus includes: a wave source configured to irradiate a wave towards a sample; a detector configured to detect a laser speckle that is generated when the wave is multiple-scattered by the sample, at every time point that is set in advance; and a controller configured to obtain a temporal correlation that is a variation in the detected laser speckle according to time, and to detect properties of the sample in real-time based on the temporal correlation, wherein the detector detects the laser speckle between the sample and the detector or from a region in the detector.

Advantageous Effects of Disclosure

In a sample property detecting apparatus according to embodiments of the present disclosure, an optical system may be implemented only by using a laser light source and an image sensor, and thus, the optical system may be provided at low costs, and moreover, the optical system may be manufactured in a small size and may be applied widely to various fields. In addition, since an optical measurement is only used to detect microbes, there is no need to use target matters such as antigen-antibody, and there is no need to take a sample as in a gene amplification technique. Thus, costs incurred during a microbe measurement process may be reduced.

BEST MODE

Figure 1:
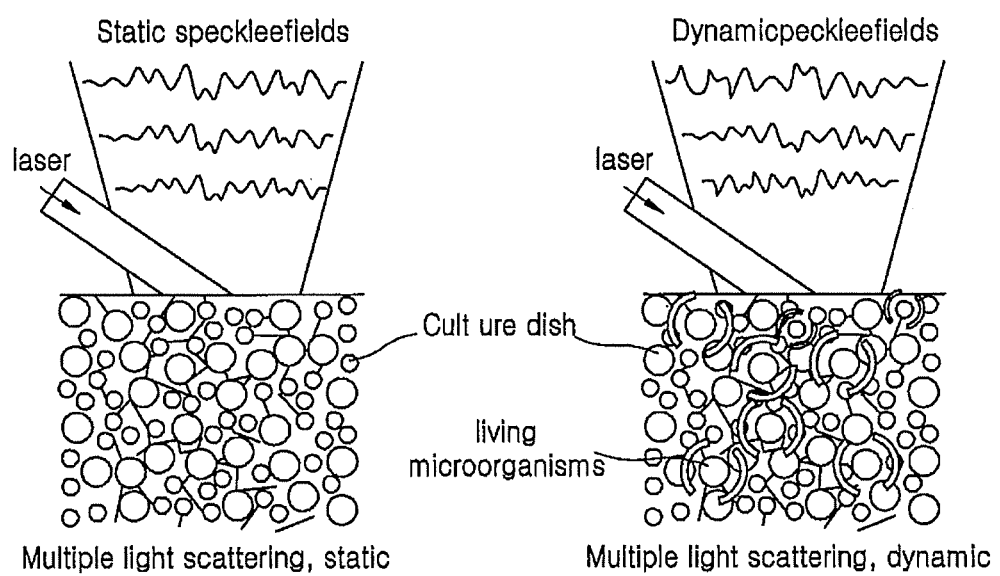
FIG. 1 is a diagram illustrating principles of a chaotic wave sensor according to an embodiment.

According to an aspect, a sample property detecting apparatus includes: a wave source configured to irradiate a wave towards a sample; a detector configured to detect a laser speckle that is generated when the wave is multiple-scattered by the sample, at every time point that is set in advance; and a controller configured to obtain a temporal correlation that is a variation in the detected laser speckle according to time, and to detect properties of the sample in real-time based on the temporal correlation, wherein the detector detects the laser speckle between the sample and the detector or from a region in the detector.

The controller may be configured to estimate in real-time an existence of a germ or a microbe, or a virus, or a concentration of the germ or the microbe, or the virus according to a variation in the speckle generated from the germ or the microbe, or the virus moving in the sample.

The detector may be configured to detect the laser speckle from a first region that is spaced a predetermined distance apart from a surface of the sample.

The first region may be arranged between a first surface including a first point spaced a first distance apart from the surface of the sample and a second surface including a second point that is spaced a second distance apart from the surface of the sample, wherein the second distance may be greater than the first distance.

The temporal correlation may include a difference between first image information of the laser speckle detected at a first time point and second image information of the laser speckle detected at a second time point that is different from the first time point.

The first image information and the second image information may include at least one of pattern information of the laser speckle and intensity information of the wave.

The sample property detecting apparatus may further include a sample arranging portion configured to accommodate the sample.

The sample property detecting apparatus may further include an antibiotic applier configured to inject a predetermined antibiotic to the sample in the sample arranging portion, wherein the controller may be configured to estimate existence of a microbe or concentration of a microbe in the sample before or after injecting the antibiotic into the sample based on the temporal correlation of the laser speckle, and to determine compatibility of the antibiotic in real-time according to the estimated existence of the microbe or a variation in the concentration of the microbe.

The sample property detecting apparatus may further include: a cover member configured to cover at least the sample arranging portion, not to expose the sample to an external environment; and a cultivation environment adjuster configured to adjust an environmental condition and to maintain a constant cultivation environment of the sample.

The sample property detecting apparatus may further include a three-dimensional (3D) image generator configured to generate a 3D speckle image by using a plurality of laser speckles detected by a plurality of detectors, when two or more detectors are provided, wherein the controller may detect sample properties by using the 3D speckle image.

The sample property detecting apparatus may further include a multiple scattering amplifier configured to increase a number of multiple scattering operations in the sample by reflecting at least some of the wave that is multiple-scattered and emitted from the sample.

The multiple scattering amplifier may include: a first multiple scattering amplifier arranged on an extending line passing through a center of the sample and configured to reflect at least some of the wave multiple-scattered and emitted from the sample towards the sample; and a second multiple scattering amplifier arranged facing the first multiple scattering amplifier based on the sample, and configured to reflect at least some of the wave multiple-scattered and emitted from the sample towards the sample.

According to an aspect, a sample property detecting apparatus includes: a sample arranging portion configured to accommodate a sample; a reference sample arranging portion arranged adjacent to the sample arranging portion and configured to accommodate a reference sample; a wave source configured to irradiate a wave towards the sample in the sample arranging portion and the reference sample in the reference sample arranging portion; a detector configured to detect a first laser speckle and a reference laser speckle that are respectively generated when the wave is multiple-scattered respectively by the sample and the reference sample, at every time point set in advance; and configured to obtain a temporal correlation that is a variation in the first laser speckle according to time by using the first laser speckle, and to detect properties of the sample in real-time based on the temporal correlation, wherein the detector may detect the laser speckle between the sample and the detector or from a region in the detector.

The controller may be configured to estimate in real-time an existence of a germ or a microbe, or a virus, or a concentration of the germ or the microbe, or the virus according to a variation in the speckle generated from the germ or the microbe, or the virus moving in the sample.

The sample property detecting apparatus may further include an antibiotic applier configured to inject a predetermined antibiotic to the sample in the sample arranging portion, wherein the controller may be configured to estimate existence of a microbe or concentration of a microbe in the sample before or after injecting the antibiotic into the sample based on the temporal correlation of the laser speckle, and to determine compatibility of the antibiotic in real-time according to the estimated existence of the microbe or a variation in the concentration of the microbe.

The temporal correlation may include a difference between first image information of the first laser speckle detected at a first time point and second image information of the first laser speckle detected at a second time point that is different from the first time point.

The first image information and the second image information may include at least one of pattern information of the laser speckle and intensity information of the wave.

The controller may be configured to obtain reference information of the reference laser speckle by using the reference laser speckle, and to remove noise applied to the temporal correlation of the first laser speckle by using the reference information.

The sample property detecting apparatus may further include: a multiple beam reflector configured to split the wave incident from the wave source to provide the wave to a plurality of wave paths; and a beam splitter arranged on the wave paths provided from the multiple beam reflector and configured to change paths of waves reflected and emitted from the sample and the reference sample and provide the changed paths to the detector.

According to an aspect, a sample property detecting apparatus includes: a wave source configured to irradiate a wave towards a sample; a detector configured to detect a laser speckle that is generated when the wave is multiple-scattered by the sample, and to detect the laser speckle on a region on a diffusing path of the laser speckle at every time point that is set in advance; and a controller configured to obtain a temporal correlation of the detected laser speckle according to time, and to detect properties of the sample in real-time based on the temporal correlation.

Other aspects, features and advantages of the present disclosure will become better understood through the accompanying drawings, the claims and the detailed description.

MODE OF DISCLOSURE

The exemplary embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it can be directly connected or coupled to the other element or intervening elements may be present.

It will be further understood that the terms "comprises," "comprising," "includes" and/or "including," when used herein, specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

Hereinafter, principles of a chaotic wave sensor according to an embodiment will be described with reference to FIG. 1.

FIG. 1 is a diagram illustrating principles of a chaotic wave sensor according to an embodiment.

When light is irradiated to a material having a uniform internal refractive index, e.g., glass, the light is refracted in a constant direction. However, when coherent light such as a laser is irradiated to a material having a non-uniform internal refractive index, multiple scattering that is very complicated occurs in the material.

Referring to FIG. 1, in light or waves (hereinafter, referred to as waves for convenience' sake) irradiated from a wave source 120, some of the waves scatter through complicated paths due to the multiple scattering pass through a test target surface. Waves passing through multiple points in the test target surface generate constructive interference or destructive interference, and the constructive/destructive interference of the waves generates grain patterns (speckles).

In the present specification, the waves scattered in the complicated paths are referred to as "chaotic wave", and the chaotic wave may be detected through laser speckles.

The left side of FIG. 1 shows a state in which a laser is irradiated to a stabilized medium. When interference light (e.g., laser) is irradiated to the stabilized medium, in which internal component material does not move, a stabilized speckle pattern without a variation may be observed.

However, as shown at the right side of FIG. 1, when the medium has a non-stabilized internal component that is moving, such as bacteria, the speckle pattern varies.

That is, fine activity of life, e.g., movement of microbes, may finely change an optical path according to time. Since the speckle pattern is generated due to interference of the waves, a fine change in the optical path may cause variation in the speckle pattern. Accordingly, when a temporal variation in the speckle pattern is measured, the activities of microbes may be rapidly measured. As described above, when the variation in the speckle pattern according to time is measured, existence of the microbes and concentration of the microbes may be identified, and further, kinds of the microbes may be identified.

In the present specification, a structure for measuring the variation in the speckle pattern is defined as a chaotic wave sensor.

Figure 2:
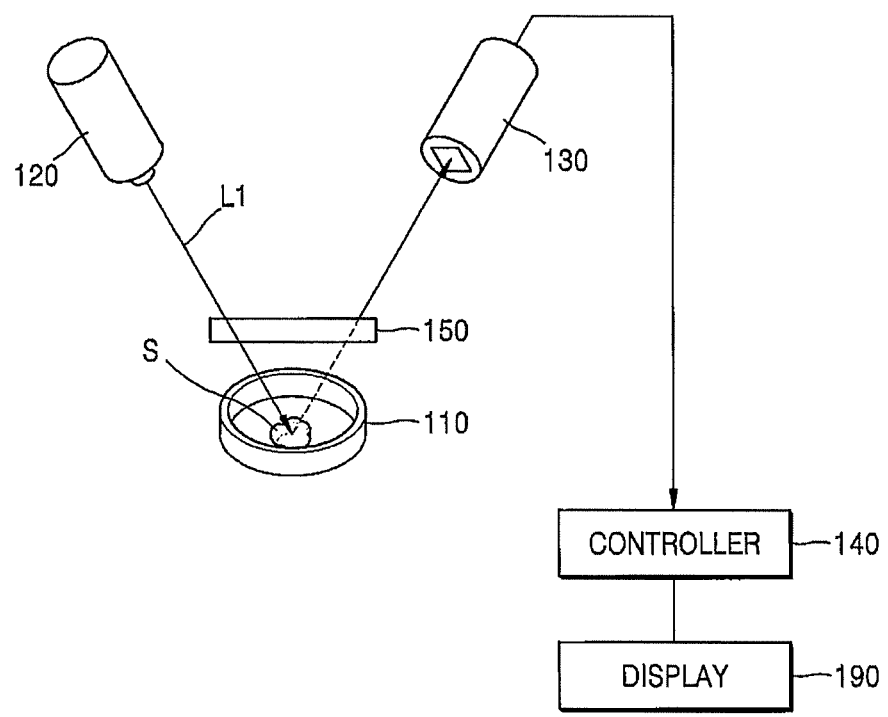
FIG. 2 is a conceptual diagram schematically showing an apparatus for detecting sample properties, according to an embodiment.
Figure 3:
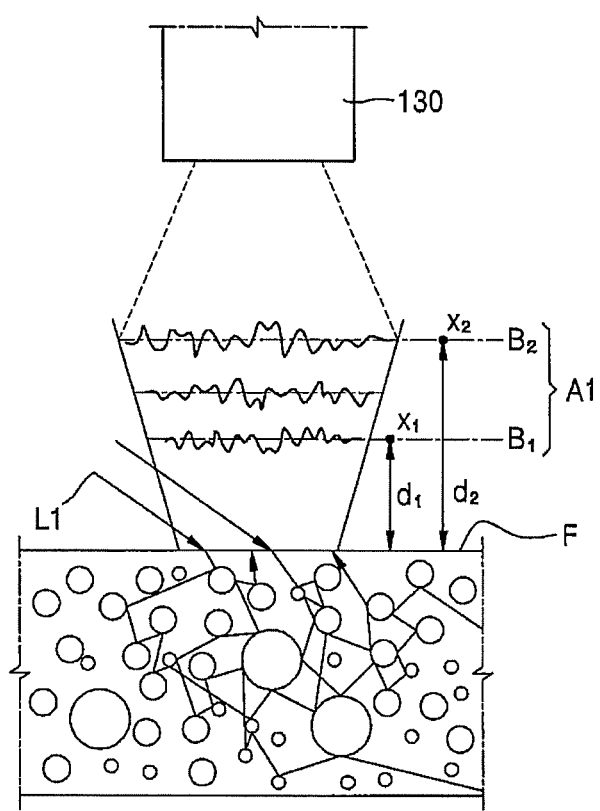
FIG. 3 illustrates a method of detecting laser speckles by using a detector of FIG. 1.
Figure 4A:
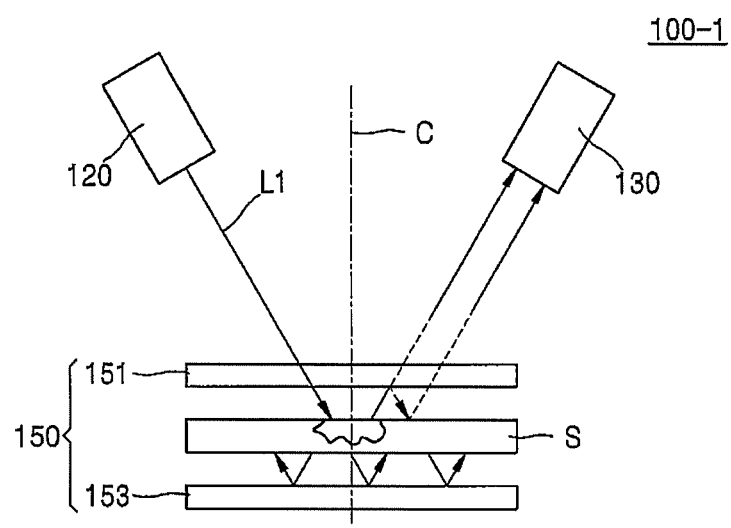
FIG. 4A, FIG. 4B, and FIG. 4C are schematic conceptual diagrams showing examples of the apparatus of detecting sample properties of FIG. 1.
Figure 4B:
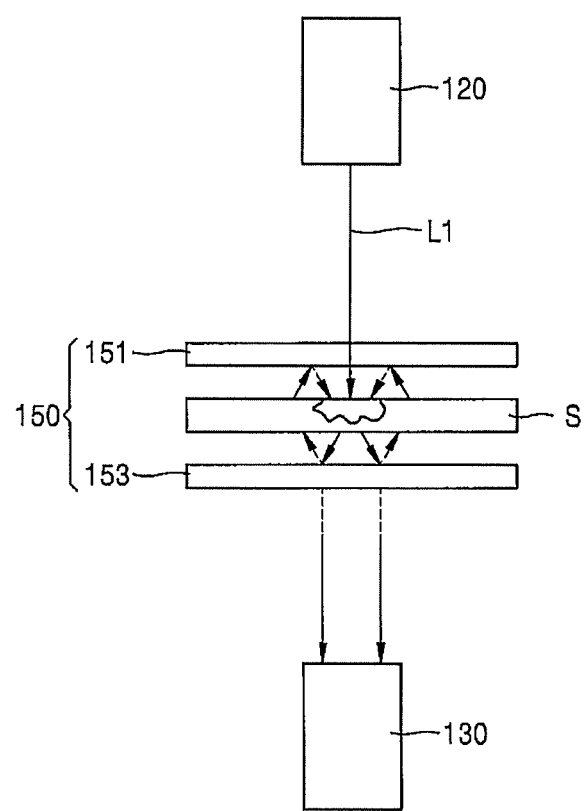
Figure 4C:
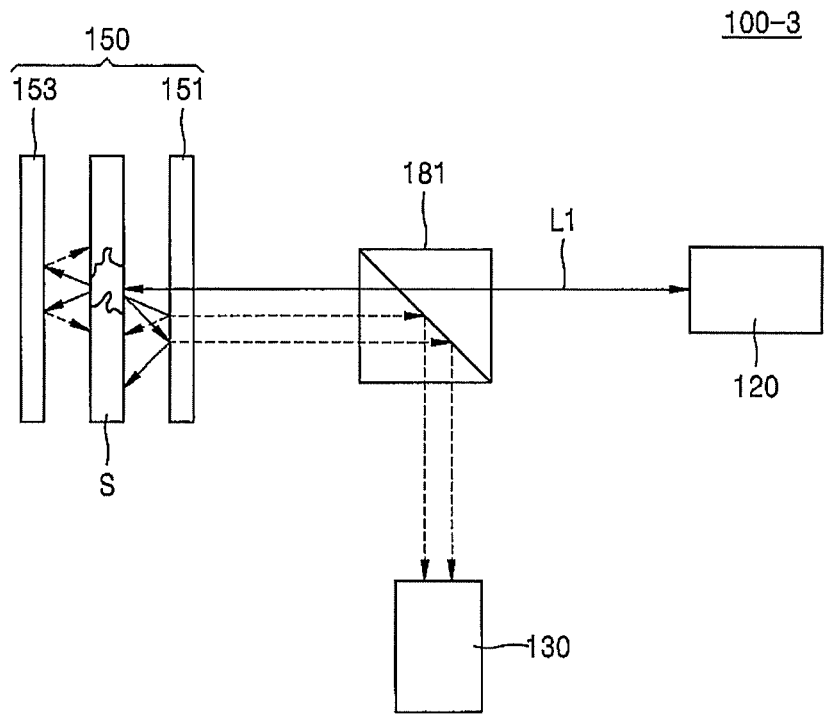

Hereinafter, one or more embodiments will be described based on the principles of the chaotic wave sensor described above. FIG. 2 is a conceptual diagram schematically showing a sample property detecting apparatus 100 according to an embodiment, and FIG. 3 is a diagram illustrating a method of detecting laser speckles by a detector 130 of FIG. 1. FIGS. 4A to 4C are schematic conceptual diagrams showing examples of the sample property detecting apparatus 100 of FIG.

Referring to FIG. 2, the sample property detecting apparatus 100 according to the embodiment may include a wave source 120, a detector 130, and a controller 140. Also, the sample property detecting apparatus 100 may further include a sample arranging portion 110, a multiple scattering amplifier 150, and a display 190.

A sample S that may be measured by the sample property detecting apparatus 100 according to the embodiment may be a sample taken from an entity to be measured, e.g., saliva, blood, and tissues, or a sample discharged out of the entity, e.g., stool, urine, and dead skin cells. Otherwise, the sample may include an organic sample taken from an entity such as food. In addition, the sample S may denote the entity to be measured itself. That is, in a case where the food is the entity and whether there is the microbe is to be measured without damaging the food, the food itself may be a sample S. For example, an entity such as meat that is packaged for selling may be the sample S. The sample S may be entirely used, or may be prepared by using a unit to which microbes may be transferred, for example, a tape, a membrane, etc. In addition, the sample S may be taken when the entity blows or is taken from the skin of the entity, or may be taken by filtering stool, etc. As an embodiment, the sample S may be accommodated in the sample arranging portion 110. The sample arranging portion 110 may have a container shape in which the sample S may be accommodated. The sample arranging portion 110 may support the sample S while restricting the movement of the sample S. In other words, the detection is performed in a state where the motion of the sample S is restricted. According to the present disclosure, the sample S may not be essentially accommodated in the sample arranging portion 110. However, for convenience of description, a case where the sample S is arranged in the sample arranging portion 110 will be described. In addition, the sample arranging portion 110 may be a petri dish such as an agar plate.

Here, the microbe may include germs selected from a group consisting of *Staphylococcus, staph Coagulase* negative, *Staph. aureus, Streptococcus* spp., *Streptococcus viridans* group, *Enterococcus* spp., *Corynebacterium* spp., *Aerococcus* spp., *Micrococcus* spp., *Peptostreptococcus* spp., *Lactococcus* spp., *Leuconostoc* spp., *Tothia* spp., *Gemella* spp., *Alcaligenes* spp., *Alternaria* spp., *Flavobacterium* spp., *Bacillus* spp., *Achromobacter* spp., *Acinetobacter* spp., *Actinobacillus* spp., *Alcaligenes* spp., *Campylobacter* spp., *Edwardsiella* spp., *Ehrlichia* spp., *Enterobacter* spp., *Ewingella* spp., *Flavobacteria, Hafnia* spp., *Klebsiella* spp., *Kluyvera* spp., *Legionella* spp., *Morxella* spp., *Morganella* spp., *Neisseria* spp., *Pasteurella* spp., *Prevotella* spp., *Proteus* spp., *Providencia* spp., *Pseudomonas* spp., *Rahnella* spp., *Salmonella* spp., *Serratia* spp., *Shigella* spp., *Sphingobacterium* spp., *Vibrio* spp.,

*Yersinia* spp., *Neisseria* spp., *Kingella* spp., *Cardiobacterium*, non-Tuberculosis mycobacteria (NTB), *Mycobacterium tuberculosis*, and *Mycobacterium avium*.

The wave source 120 may irradiate the wave towards the sample S in the sample arranging portion 110. The wave source 120 may include all kinds of source devices capable of generating waves, for example, may be a laser irradiating light of a certain wavelength band. Although the present disclosure is not limited to the kind of wave source, for convenience of description, a case where the wave source is a laser will be described below.

For example, the laser having excellent coherence may be used as the wave source 120 in order to form speckles on the sample arranging portion 110. Here, when a spectral bandwidth of the wave source is shorter, a measuring accuracy may increase, wherein the spectral bandwidth determines the coherence of the laser wave source. That is, when a coherence length increases, the measuring accuracy also increases. Accordingly, a wave source irradiating the laser having a spectral bandwidth that is less than a reference bandwidth set in advance may only be used as the wave source 120, and when the spectral bandwidth is reduced to be less than the reference bandwidth, the measuring accuracy may increase. For example, the spectral bandwidth of the wave source may be set to satisfy the following condition of Equation 1 below.

$$\text{Spectral bandwidth} < 1 \text{ nm} \qquad \text{[Equation 1]}$$

According to Equation 1 above, when the light is irradiated into the petri dish at every reference time in order to measure a variation in the laser speckle pattern, the spectral bandwidth of the wave source 120 may be maintained to be less than 1 nm.

Referring back to FIG. 2, the detector 130 may detect the laser speckle that is generated by the multiple scattering of the irradiated wave due to the sample S at every predetermined time point. Here, the time point may denote one instant during continuous flow of time, and time points may be set in advance with constant time intervals therebetween, but are not limited thereto, that is, may be set in advance with an arbitrary time interval. The detector 130 may include a sensing unit corresponding to the kind of the wave source 120, for example, an image sensor that is an imaging device in a case where a light source of a visible ray wavelength band is used. As an embodiment, the detector 130 may detect the laser speckle by using an image sensor and one or more lenses having a predetermined focal length. Here, the focal length may be shorter than a distance between the sample S and the detector 130, but is not limited thereto. As another embodiment, the detector 130 may include an image sensor having no lens. The detector 130 may detect the laser speckle at a first time point at least, and may detect the laser speckle at a second time point, and then, may provide the controller 140 with the detected laser speckles. The first time point and the second time point are just examples selected for convenience of description, and the detector 130 may detect laser speckles at a plurality of time points more than the first and second time points.

In detail, when the wave is irradiated to the sample S, the incident wave may generate a laser speckle due to the multiple scattering. The laser speckle is generated by a light interference effect, and thus, when there is no motion in the sample S, a constant interference pattern may be shown according to time. Compared to this, when microbes such as bacteria exist in the sample S, the laser speckle may vary according to time due to the movement of the microbes. The detector 130 detects the laser speckle varying according to time at every time point set in advance, to provide the laser speckle to the controller 140. The detector 130 may detect the laser speckle at a sufficient speed to sense the movement of the microbes, for example, 25 frames to 30 frames per second.

Referring to FIG. 3, the detector 130 may detect the laser speckle that is generated when the wave irradiated to the sample S is multiple scattered due to the sample S. In other words, the detector 130 may detect the laser speckle caused by the sample S. In detail, the detector 130 may detect the laser speckle from a surface F of the sample S, or may detect the laser speckle from a region A1 on a path, through which the wave multiple-scattered by the sample S moves, at every time point set in advance. Here, the first region A1 may be spaced a predetermined distance apart from the surface F of the sample S. As an embodiment, the first region A1 may be arranged between a first surface B1 including a first point x1 that is spaced a first distance d1 from the surface F of the sample S, and a second surface B2 including a second point x2 that is spaced a second distance d2 from the surface F of the sample S, wherein the second distance d2 is greater than the first distance d1. That is, the laser speckle may be detected from the first region A1 between the detector 130 and the sample S. Otherwise, the laser speckle may be detected in the detector, for example, when the detector 130 is a charge coupled device (CCD) sensor, the laser speckle may be detected from the surface of the CCD sensor. As another embodiment, the detector 130 may detect the laser speckle by using the image sensor. When the laser speckle is detected by using the image sensor, the focal length may be reduced to be less than that of a case where the laser speckle is observed from the surface of the sample S.

In addition, in a case where the image sensor is used as the detector 130, the image sensor may be arranged so that a side d of one pixel in the image sensor is equal to or less than a grain size of the speckle pattern. For example, the image sensor may be arranged in the optical system of FIGS. 4A to 4C, to satisfy the condition of Equation 2 below.

$$d \leq \text{speckle grain size} \qquad \text{[Equation 2]}$$

As expressed by Equation 2 above, the size d of one pixel in the image sensor has to be equal to or less than the grain size of the speckle pattern, but if the size of the pixel is too small, an undersampling may occur and it may be difficult to utilize the pixel resolution. Accordingly, in order to achieve an effective signal to noise ratio (SNR), the image sensor may be arranged to make five or less pixels correspond to the speckle grain size.

In order to compare dynamic change in a speckle signal, at least two images measured at different time points from each other may be necessary. For example, two or more laser speckle images may be generated at every reference time with a predetermined interval. For example, there may be a first laser speckle image generated by capturing an image of a test target after irradiating laser at a current time, and a second laser speckle image generated by capturing an image of the petri dish after irradiating light ten seconds later. In addition, a third laser speckle image may be generated ten seconds later, and a fourth laser speckle image may be generated again ten seconds later. That is, the light may be irradiated with predetermined intervals after initially irradiating light, and then, n laser speckle images may be generated after 10(n−1) seconds. Then, a difference between the generated laser speckle images may be analyzed to detect whether the microbes exist in the petri dish.

Here, the method of detecting microbes may vary according to whether the existence of microbes is detected by using two speckle images or three or more speckle images.

As an example, when two speckle images generated at different time points by irradiating light with a predetermined time interval are used, a difference between the speckle image measured at 0 seconds and the speckle image generated at 10 seconds may be very small, that is, equal to or less than a first reference value if there is no microbe in the test target. Although there may be a small signal difference, this may be interpreted as influence of noise existing during the experiment, e.g., moisture evaporation, vibration, etc. Here, when the microbes exist in the petri dish (for example, B. cereus, E. coli, etc.), the difference between the speckle image generated at 0 seconds and the speckle image generated at 10 seconds may be equal to or greater than a second reference value defined in advance. That is, when the difference between the speckle images at 0 seconds and 10 seconds is equal to or greater than a second reference value, that is, when there is a large variation in the signal, it may be detected that microbes such as bacteria exist in the test target.

The controller 140 obtains temporal correlation by using the detected laser speckles, and may estimate the existence of the microbes or concentration of the microbes included in the sample S in real-time based on the temporal correlation. In the present specification, real-time denotes determining of suitability of antibiotics by estimating whether the microbes exist or estimating variation in concentration of the microbes within one hour, for example, the existence of microbes or the variation in the concentration of the microbes may be estimated within five minutes. In detail, the existence of the microbes or the variation in concentration of the microbes may be estimated within twenty (20) seconds. As such, the controller 140 may detect whether the microbes exist in the petri dish, by checking whether the difference between two speckle images (e.g., difference between pixel values) is equal to or less than a first reference value, and equal to or higher than the second reference value. Here, the first reference value and the second reference value may be defined as equivalent values, or different values from each other. As another example, when three or more speckle images generated with predetermined time intervals are used, the controller 140 may perform a time correlation analysis on the three or more speckle images to detect whether the microbes exist in the petri dish. That is, the detector 130 may detect whether the microbes exist in the petri dish based on the temporal correlation between the laser speckles that are generated by irradiating light to the test target at different time points with a predetermined time interval and causing multiple scattering. For example, assuming that data standardizing the speckle image measured at each time point t is I(x,y;t), the controller 140 may calculate the temporal correlation coefficient at each time point, with respect to a certain time delay $\tau$. The method of estimating the existence of the microbes or the variation in the concentration of microbes, performed by the controller 140, will be described later.

In addition, referring to FIGS. 4A to 4C, the sample property detecting apparatus 100 according to the embodiment may further include the multiple scattering amplifier 150.

The multiple scattering amplifier 150 may reflect at least some of the waves that are emitted from the sample S after being multiple scattered towards the sample S, in order to increase the number of multiple scattering operations in the sample S. The multiple scattering amplifier 150 may include a multiple scattering material. For example, the multiple scattering material may include a particle having a diameter equal to or less than a micrometer and having a large refractive index, for example, titanium oxide ($TiO_2$) nanoparticles, and the multiple scattering amplifier 150 may reflect at least some of the waves incident into the multiple scattering amplifier 150. The multiple scattering amplifier 150 is arranged adjacent to the sample S, and thus, the waves multiple-scattered and emitted from the sample S may reciprocate at least once between the sample S and the multiple scattering amplifier 150. Although the microbes may exist in the sample S, the number of microbes may be insignificant. According to the related art, the microbes have to be multiplied for a long time period, e.g., a few days, in order to detect the microbes in the sample S, and thus, it takes a long time period to detect the microbes. However, the sample property detecting apparatus 100 according to the embodiment increase the number of multiple scattering of the waves in the sample S by using the multiple scattering amplifier 150, and thus, the microbes may be rapidly and accurately detected.

The multiple scattering amplifier 150 may reflect some of the incident waves, and may transmit the other waves. Otherwise, the multiple scattering amplifier 150 may transmit some of the incident waves, and may reflect the other waves. Otherwise, the multiple scattering amplifier 150 may reflect all of the incident waves. The multiple scattering amplifier 150 may include at least one of above-described structures to correspond to the optical system structure including the wave source 120 and the detector 130.

Referring to FIG. 4A, a sample property detecting apparatus 100-1 may include an optical system including the wave source 120 and the detector 130 as a reflective type. A wave L1 incident to the sample S may be partially reflected because multiple scattering occurs due to uneven optical characteristics of the sample S. Here, the detector 130 captures an image of a laser speckle signal generated when the wave is reflected by and emitted from the sample S due to the uneven optical characteristics of the sample S to measure a laser speckle caused by the sample S.

The sample property detecting apparatus 100-1 may include a first multiple scattering amplifier 151 and a second multiple scattering amplifier 153. The first multiple scattering amplifier 151 is arranged on an extending line C passing through a center of the sample S, and may reflect at least some of the waves emitted from the sample S after being multiple-scattered towards the sample S. The second multiple scattering amplifier 153 may face the first multiple scattering amplifier 151 based on the sample S, and may reflect at least some of the waves emitted from the sample S after being multiple-scattered towards the sample S. In a case of the reflective optical system, the first multiple scattering amplifier 151 may be a semi-transmission type that transmits some of the waves and reflects some other of the waves. Also, the second multiple scattering amplifier 153 may be a reflective type that reflects all of the incident waves. As such, the number of multiple-scattering of the waves in the sample S may be greatly increased.

In FIG. 4A, the wave source 120 may be used without limitation in a wavelength, an intensity of the wave, etc., and a camera capable of measuring two-dimensional information is preferred as the detector 130, but a camera measuring one-dimensional information may be used.

In FIG. 4A, locations of the wave source 120 and the sample S are not restricted, and the detector 130 measuring a reflected laser speckle signal may be located to make one measured speckle size correspond to two or three pixels among the pixels of the detector 130. For example, the detector 130 may be inclined by a predetermined angle with respect to a light incident surface of the sample S in order to measure the laser speckle signal caused by the reflection of the wave from the sample S.

Referring to FIG. 4B, a sample property detecting apparatus 100-2 may include the optical system including the wave source 120 and the detector 130 as a transmission type. The waves incident to the sample S are multiple-scattered due to the uneven optical characteristics of the sample S, and thus, some waves may be emitted from the sample S after passing through it. Then, the detector 130 captures an image of a laser speckle signal generated when the wave transmits through and emits from the sample S, to measure the laser speckle caused by the wave transmitting through the sample S. When the optical system of the sample property detecting apparatus 100-2 is configured as a transmission type, the first multiple scattering amplifier 151 and the second multiple scattering amplifier 153 may be a semi-transmission type that transmits some of the waves and reflects some other of the waves.

Referring to FIG. 4C, a sample property detecting apparatus 100-3 may include an optical system including the wave source 120 and the detector 130 as a spectral type. Waves L1 are incident to the sample S, and some waves are reflected due to the multiple-scattering caused by the uneven optical characteristics of the sample S. Then, paths of some waves may be changed to the detector 130 by using a beam splitter 181. Since the spectral type uses a polarized state of the wave, an optical unit such as a phase retardation plate or a polarizing plate may be further provided. Here, the detector 130 is located between the wave source 120 and the sample S to change the paths of the waves reflected by the sample S. Also, the detector 130 may measure the laser speckle generated when the waves are reflected by the sample S and the optical paths are changed.

In addition, when the optical system of the sample property detecting apparatus 100-3 is a spectral type, the first multiple scattering amplifier 151 may be a semi-transmission type that transmits some of the waves and reflects some other of the waves. Also, the second multiple scattering amplifier 153 may be a reflective type that reflects all of the incident waves.

Figure 5:
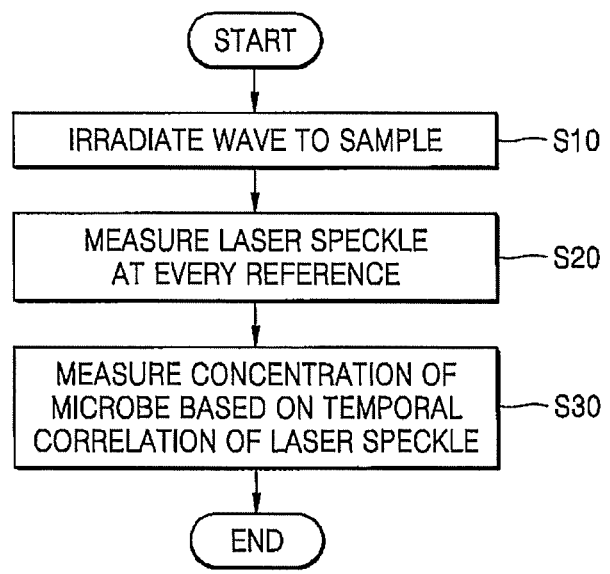
FIG. 5 is a flowchart illustrating a method of detecting microbes by using the apparatus for detecting sample properties, according to an embodiment.

FIG. 5 is a flowchart illustrating a method of detecting microbes by using the sample property detecting apparatus 100, according to an embodiment.

Referring to FIG. 5, waves may be irradiated to the sample S from the wave source 120 (S10). Next, the detector 130 may detect the laser speckles at every time point set in advance, wherein the laser speckles are generated due to the multiple-scattering of the waves incident to the sample S. Next, the controller 140 may calculate the temporal correlation coefficient between laser speckle images by using the laser speckle images generated at the time points set in advance, and may estimate whether microbes exist in the sample S based on the temporal correlation coefficient (S30). Also, the controller 140 may measure the concentration of the microbes based on a variation rate of the temporal correlation coefficient.

Here, during the measurement of the laser speckles generated by the sample S, the optical system including the wave source 120 and the detector 130 may be restricted from moving. For example, the concentration of the microbes may be exactly measured only when the wave source 120 and the detector 130 do not move until the waves are irradiated from the wave source 120 to the sample S and the concentration of the microbes is measured. The optical system may be configured as a reflective type, a transmission type, or a spectral type, as described above.

In addition, the sample property detecting apparatus 100 may further include a display 190. The display 190 may display the existence of the microbes estimated by the controller 140 or a result of measuring concentration of the microbes to outside.

Hereinafter, a controlling method of the controller 140 according to an embodiment will be described below with reference to FIG. 6.

Figure 6:
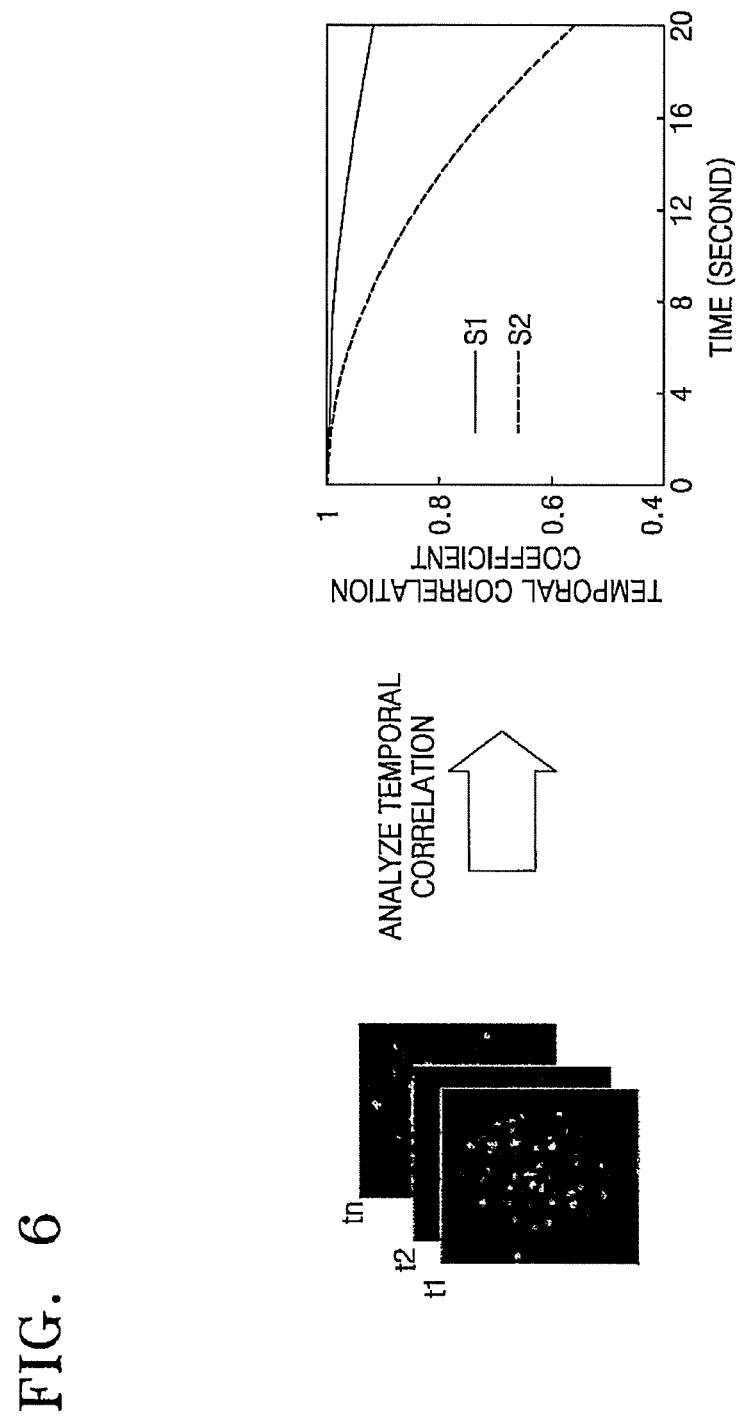
FIG. 6 is a diagram illustrating a method, performed by a controller, of analyzing correlation between laser speckles and time.

FIG. 6 is a diagram illustrating a method, performed by the controller 140, of analyzing correlation between laser speckles and time.

Referring to FIG. 6, as an embodiment, the controller 140 may estimate whether the microbes exist or the concentration of the microbes by using a difference between first image information of the laser speckle detected at a first time point and second image information of the laser speckle detected at a second time point that is different from the first time point. Here, the first image information and the second image information may include at least one of laser speckle pattern information and wave intensity information. In addition, according to the embodiment, the difference between the first image information at the first time point and the second image information at the second time point is not only used, but image information of a plurality of laser speckles detected from a plurality of time points may be also used. The controller 140 may calculate a temporal correlation coefficient between the images by using image information of the laser speckles generated at the plurality of time points set in advance, and may estimate the existence of the microbes or concentration of the microbes in the sample S based on the time correlation coefficient.

The temporal correlation coefficient between the detected laser speckle images may be calculated by using Equation 3 below.

$$\bar{C}(x, y; \tau) = \frac{1}{T-\tau}\sum_{t=1}^{T-\tau} \bar{I}(x, y; t)\bar{I}(x, y; t+\tau)\delta t \qquad \text{[Equation 3]}$$

In Equation 3 above, C denotes a temporal correlation coefficient, I denotes a standardized light intensity, (x,y) denotes a pixel coordinate of a camera, t denotes a measurement time, T denotes a total measurement time, and τ denotes a time lag.

According to Equation 3, the temporal correlation coefficient may be calculated, and as an embodiment, the existence of the microbes or the concentration of the microbes may be estimated by analyzing whether the temporal correlation coefficient is below a reference value set in advance. In more detail, when the temporal correlation coefficient is below the reference value beyond an error range set in advance, it may be estimated that the microbes exist. Also, since a time period during which the temporal correlation coefficient is below the reference value is reduced when the concentration of microbes increases, the concentration of microbes may be estimated via an inclination value of a graph showing the time correlation coefficient. The reference value may vary depending on environmental elements such as a kind of the microbe and a temperature. In the graph of FIG. 6, a solid line S1 denotes the temporal correlation coefficient of a sample in which microbes do not exist, and a dashed line S2 denotes the temporal correlation coefficient of a sample in which microbes exist. When the concentration of the microbes changes, an inclination value of the dashed line S2 may also change.

Hereinafter, the controller 140 determining the concentration of microbes in the sample by using the laser speckles will be described in detail with reference to FIG. 7.

Figure 7:
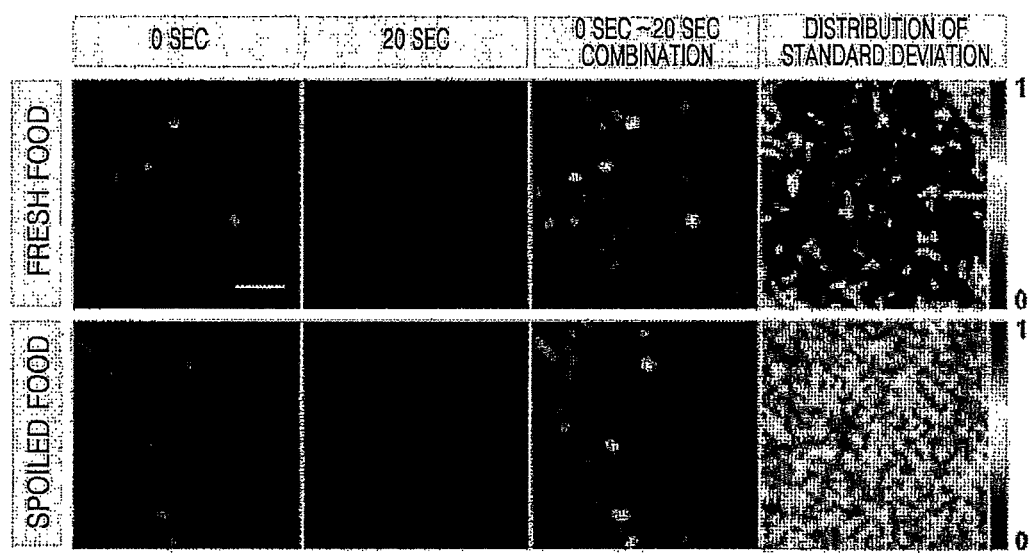
FIG. 7 shows distribution of standard deviation in a light intensity of laser speckles measured according to time by the apparatus for detecting sample properties according to the embodiment.

FIG. 7 shows distribution of standard deviation in a light intensity of laser speckles measured according to time by the apparatus for detecting sample properties according to the embodiment.

Referring to FIG. 7, the controller 140 may calculate a standard deviation of light intensity of the laser speckle, on a laser speckle image captured at every reference time.

Since bacteria and microbes existing in the sample continuously move, constructive interference and destructive interference may vary according to the movements. Here, when the constructive interference and the destructive interference change, the light intensity may largely change. Then, the controller 140 may calculate the standard deviation representing the variation degree of the light intensity, to identify whether bacteria and microbes exist in the sample.

For example, the controller 140 detects the laser speckle image at every time point determined in advance, and may calculate the standard deviation of the light intensity of the laser speckle according to time in the detected images. The standard deviation of the light intensity of the laser speckle according to time may be calculated by using Equation 4 below.

$$S(x, y) = \sqrt{\frac{1}{T}\sum_{t=1}^{T}(I_t(x, y) - \bar{I})^2}$$ [Equation 4]

In Equation 4 above, S denotes the standard deviation, (x,y) denotes a pixel coordinate of the camera, T denotes a total measurement time, t denotes a measurement time, $I_t$ denotes a light intensity measured at the time t, and I denotes an average light intensity according to time.

The constructive and destructive interferences may vary depending on the movements of the bacteria and microbes, and the standard deviation value calculated according to Equation 4. Thus, the concentration of the bacteria and the microbes may be measured based on the standard deviation value.

In addition, the controller 140 may measure distribution, that is, concentration of the bacteria and microbes included in the sample, based on a linear relationship between a magnitude of the standard deviation value of the laser speckle light intensity and the concentration of the bacteria and the microbes.

Figure 8A:
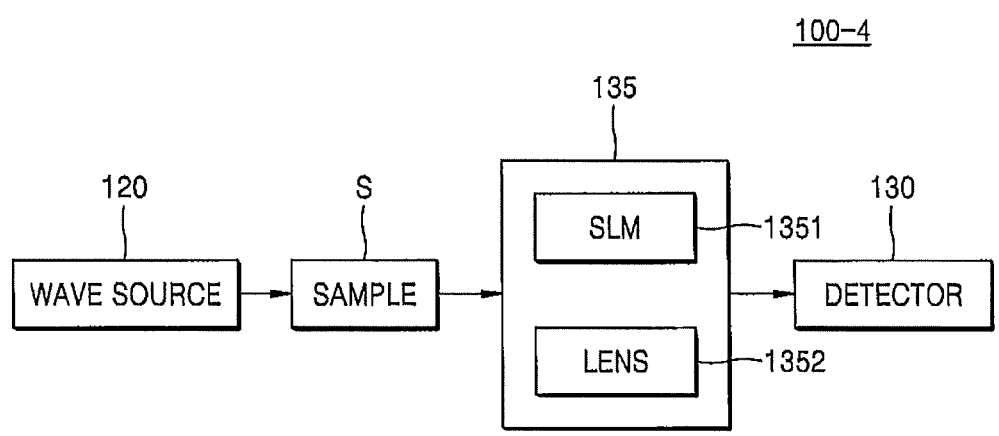
FIGS. 8A and 8B are conceptual diagram schematically showing an apparatus for detecting sample properties according to an embodiment.
Figure 8B:
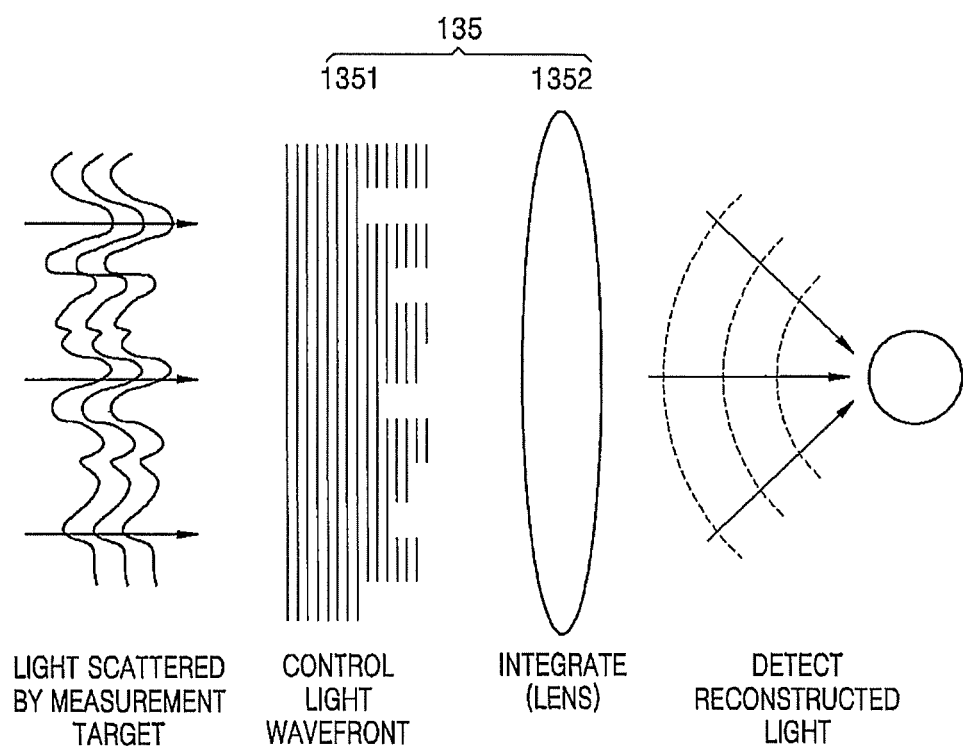

FIGS. 8A and 8B are conceptual diagrams schematically showing a sample property detecting apparatus 100-4 according to an embodiment. In FIGS. 8A and 8B, the relation between an optical portion 135 and the detector 130 will be described for convenience of description.

Referring to FIGS. 8A and 8B, the sample property detecting apparatus 100-4 may further include the optical portion 135 that modulates to reconstruct a first wave signal scattered by the sample into a second optical signal before the wave of the wave source 120 is scattered by the sample. Here, the optical portion 135 may include a spatial light modulator (SLM) 1351 and the detector 130. When the waves scattered by a measurement target are incident to the optical portion 135, the optical portion 135 controls a wave front of the scattered wave to reconstruct the wave (light) before being scattered and provides the reconstructed wave to the detector 130.

The wave (light) scattered by the sample may be incident to the SLM 1351. The SLM 1351 may control the wave front of the wave scattered by the sample and provide the wave to a lens 1352. The lens 1352 may concentrate controlled light and provide the concentrated light to the detector 130. The detector 130 senses a wave concentrated on the lens and reconstructs the wave output from the wave source before being scattered, and then, outputs reconstructed wave.

Here, the optical portion 135 may reconstruct the first optical signal scattered by the sample into the light before being scattered, in a case where there is no movement of a life in a stabilized medium, that is, the measurement target. However, in a case where viruses exist in the measurement target, the first optical signal varies due to movement of a detecting complex, a phase control wave front may not be sensed, and accordingly, the first optical signal may not be modulated into a second optical signal having an optical phase conjugate wave front. The sample property detecting apparatus 100-4 including the optical portion 135 may estimate more accurately the existence of the microbes or the concentration of the microbes by using the difference of the second optical signal.

Hereinafter, a sample property detecting apparatus 200 according to another embodiment will be described.

Figure 9:
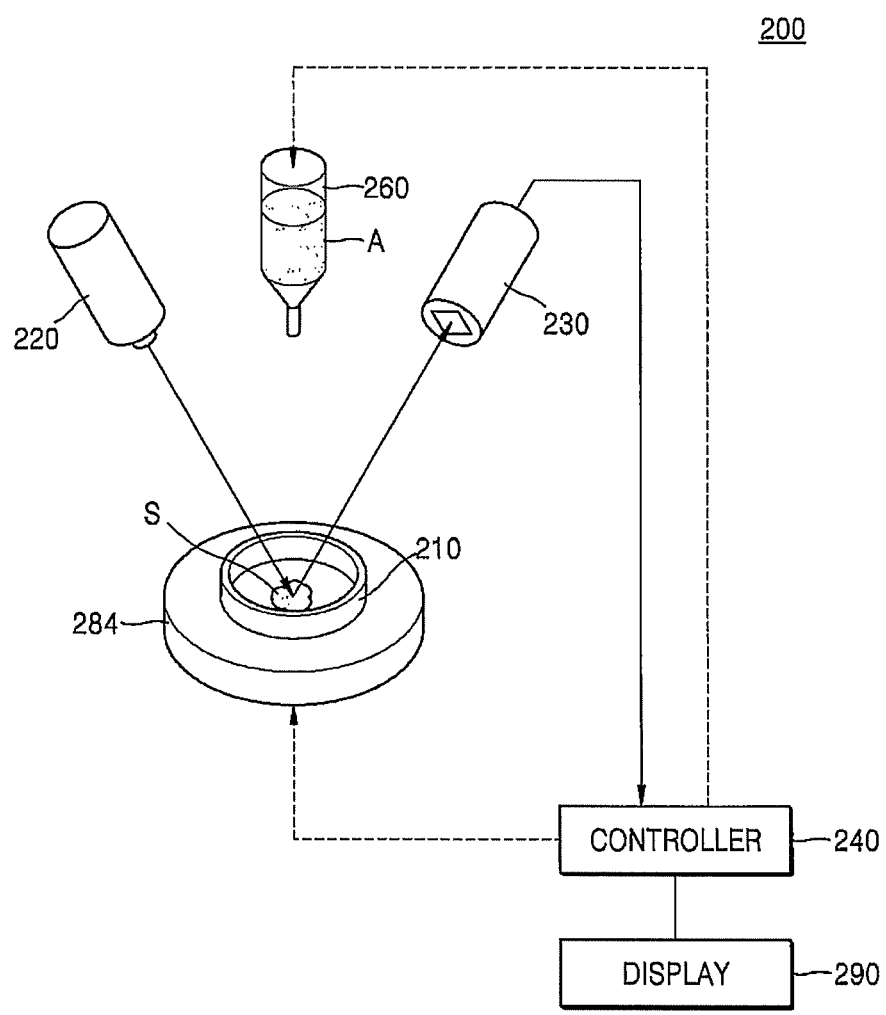
FIG. 9 is a conceptual diagram schematically showing an apparatus for detecting sample properties, according to another embodiment.

FIG. 9 is a conceptual diagram schematically showing a sample property detecting apparatus 200, according to another embodiment.

Referring to FIG. 9, the sample property detecting apparatus 200 according to the embodiment may include a sample arranging portion 210, an antibiotic applier 260, a wave source 220, a detector 230, and a controller 240. Structures of the wave source 220, the detector 230, and the controller 240 and the method of detecting microbes by using the elements according to the embodiment are the same as those of the previous embodiment, and thus, detailed descriptions thereof are omitted here.

The sample arranging portion 210 may accommodate a sample S. Here, the sample S may include a sample such as saliva, blood, or tissues, or an organic sample such as food. The sample arranging portion 210 may have a container shape in which the sample S may be accommodated. The sample S may be entirely used, or may be prepared by using a unit to which microbes may be transferred, for example, a tape, a membrane, etc.

The antibiotic applier 260 may inject a predetermined antibiotic A to the sample S in the sample arranging portion 210. The antibiotic applier 260 may be adjacent to the sample arranging portion 210, for example, as shown in the drawings, the antibiotic applier 260 may be arranged facing the sample arranging portion 210 to supply the antibiotics to the sample S. The antibiotic applier 260 may inject a kind of antibiotic, and if the injected antibiotic does not have compatibility, another kind of antibiotic may be injected. As another embodiment, a plurality of antibiotic appliers 260 corresponding to a plurality of antibiotics may be provided, and the antibiotic appliers 260 may be replaced if necessary.

The wave source 220 may irradiate the wave towards the sample S in the sample arranging portion 210. The wave source 220 may include all kinds of source devices capable of generating waves, for example, may be a laser irradiating light of a certain wavelength band.

The detector 230 may detect the laser speckle that is generated by the multiple scattering of the irradiated wave due to the sample S at every predetermined time point. Here, the time point may denote one instant during continuous flow of time, and time points may be set in advance with constant time intervals therebetween, but is not limited thereto, that is, may be set in advance with an arbitrary time interval. The detector 230 may include a sensing unit corresponding to the kind of the wave source 220, for example, a CCD camera that is an imaging device in a case where a light source of a visible ray wavelength band is used. The detector 230 may detect the laser speckle at a first time point at least, and may detect the laser speckle at a second time point, and then, may provide the controller 240 with the detected laser speckles. Here, the first time point may be before injecting the antibiotic to the sample S, and the second time point may be after injecting the antibiotic to the sample S. The first time point and the second time point are just examples selected for convenience of description, and the detector 230 may detect laser speckles at a plurality of time points more than the first and second time points.

The controller 240 obtains temporal correlation by using the detected laser speckles, and may estimate the existence of the microbes or concentration of the microbes before or after injecting the antibiotic to the sample S based on the temporal correlation. The controller 240 may determine compatibility of the applied antibiotic in real-time, according to the estimated existence of the microbes or a variation in the concentration of the microbes. In the present specification, real-time denotes determining of compatibility of antibiotics by estimating whether the microbes exist or estimating variation in concentration of the microbes within one hour, for example, the compatibility of the antibiotic may be determined by estimating the existence of microbes or the variation in the concentration of the microbes within five minutes. In more detail, the compatibility of the antibiotic may be determined by estimating the variation in the concentration of the microbes in 20 seconds.

In addition, the sample property detecting apparatus 200 according to the present embodiment may further include a temperature adjuster 284 connected to the sample arranging portion 210 to supply heat of a preset temperature to the sample arranging portion 210. The temperature adjuster 284 is controlled by the controller 240, and may provide heat for maintaining an appropriate temperature to accelerate propagation of the microbes in the sample S. For example, the controller 240 may control the temperature adjuster 284 to maintain the temperature of the sample S at about 30° C. to about 40° C. However, the present disclosure is not limited thereto, and the controller 240 may control the temperature adjuster 284 to a set temperature that varies depending on the kinds of microbes to be detected.

Figure 10:
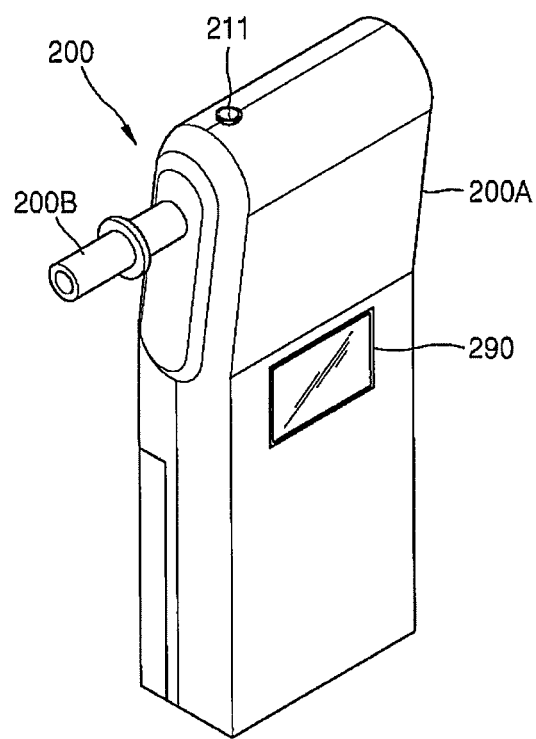
FIG. 10 is a perspective view schematically showing an example of the apparatus for detecting sample properties, according to another embodiment.
Figure 11:
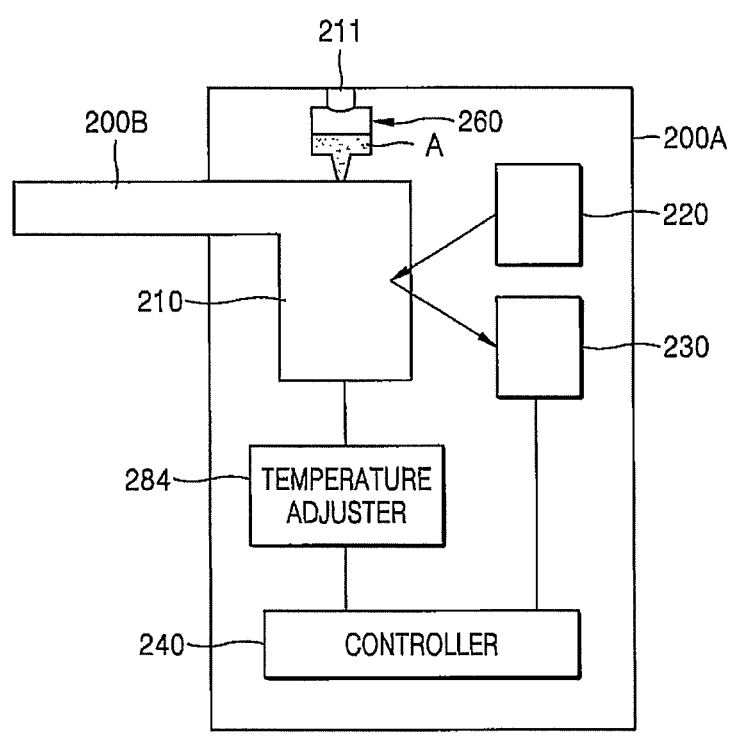
FIG. 11 is a block diagram of the apparatus for detecting sample properties of FIG. 10.

FIG. 10 is a schematic perspective view of the sample property detecting apparatus 200 according to the embodiment, and FIG. 11 is a block diagram of the sample property detecting apparatus 200 of FIG. 10.

Referring to FIGS. 10 and 11, the sample property detecting apparatus 200 may further include a cover member 200A and a sample transfer portion 200B.

The cover member 200A may cover at least the sample arranging portion 210 in order not to expose the sample S to an external environment. As an embodiment, the cover member 200A may include the above components, that is, the sample arranging portion 210, the antibiotic applier 260, the wave source 220, the detector 230, and the controller 240 therein. When the sample S is exposed to the external environment and noise occurs during the test for the compatibility of antibiotic, the test may not be accurately performed. Therefore, the cover member 200A may isolate the sample S from the external environment, in particular, from the external air, in order to reduce contamination and improve accuracy.

The sample transfer portion 200B has an end connected to the sample arranging portion 210 and the other end protruding out of the cover member 200A, and includes a through hole extending in a lengthwise direction between the end and the other end so that the sample S may be transferred to the sample arranging portion 210 via the other end. The sample S may be taken by a syringe, and may be directly transferred to the sample arranging portion 210 via the sample transfer portion 200B without being exposed to the external air. As another embodiment, a test target may blow the other end of the sample transfer portion 200B to transfer the sample S to the sample arranging portion 210.

Here, the antibiotic applier 260 may include an antibiotic injection hole 211 connected to an outer portion of the cover member 200A, in order to supply the antibiotic to the antibiotic applier 260 from outside.

In addition, the sample property detecting apparatus 200 may further include a display 290. A display 290 may display the existence of the microbes or the concentration of the microbes estimated by the controller 240 to outside, and as shown in the drawings, the display 290 may be arranged on an outer portion of the cover member 200A.

Figure 12:
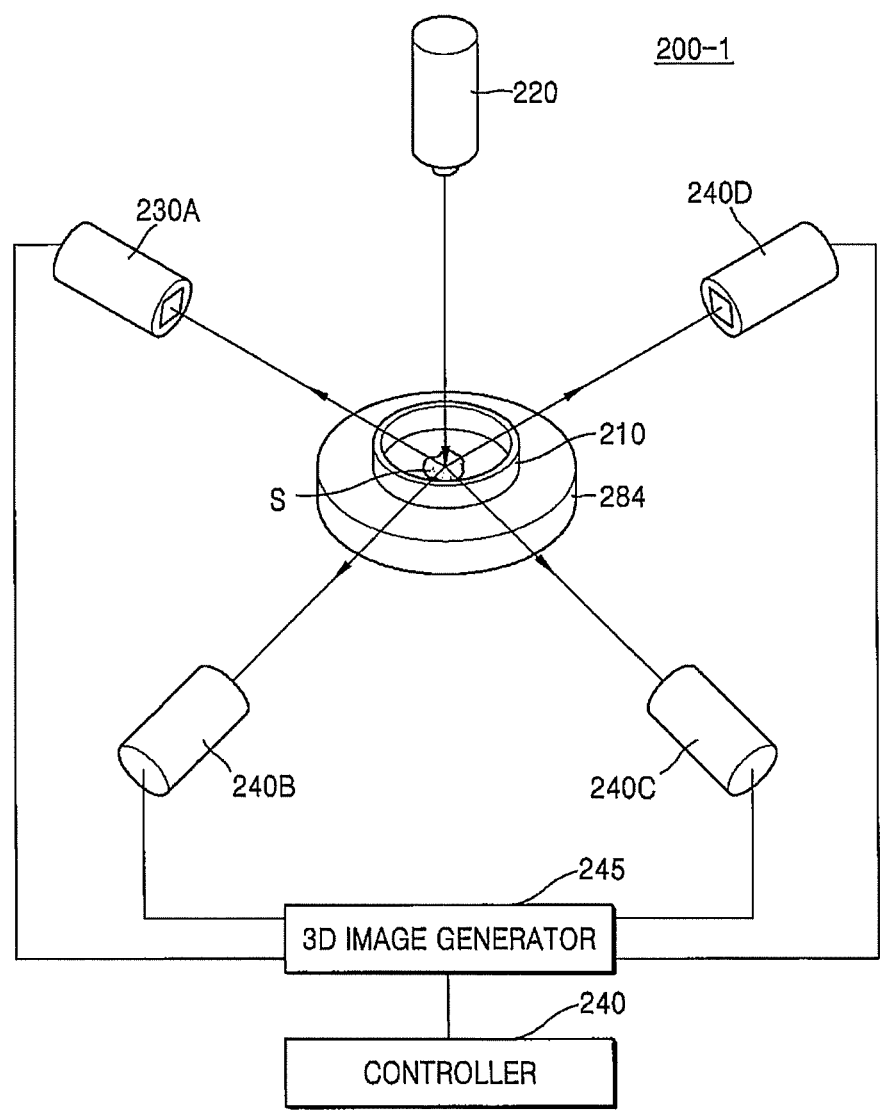
FIG. 12 is a schematic diagram of another example of the apparatus for detecting sample properties according to another embodiment.

In addition, FIG. 12 is a schematic diagram of another example of a sample property detecting apparatus 200-1 according to another embodiment.

As another embodiment, the sample property detecting apparatus 200-1 may include two or more detectors 230A, 230B, 230C, and 230D. Here, the sample property detecting apparatus 200-1 may further include a three-dimensional (3D) image generator 245 that generates a 3D speckle image by using a plurality of laser speckles detected by the plurality of detectors 230A, 230B, 230C, and 230D. The number of detectors 230 that are theoretically necessary for generating a 3D image is two, but two detectors are to identify relative images. Thus, at least three detectors 230 may be provided in order to generate an absolute 3D image. In FIG. 12, four detectors 230A, 230B, 230C, and 230D are shown in order to improve accuracy.

Figure 13:
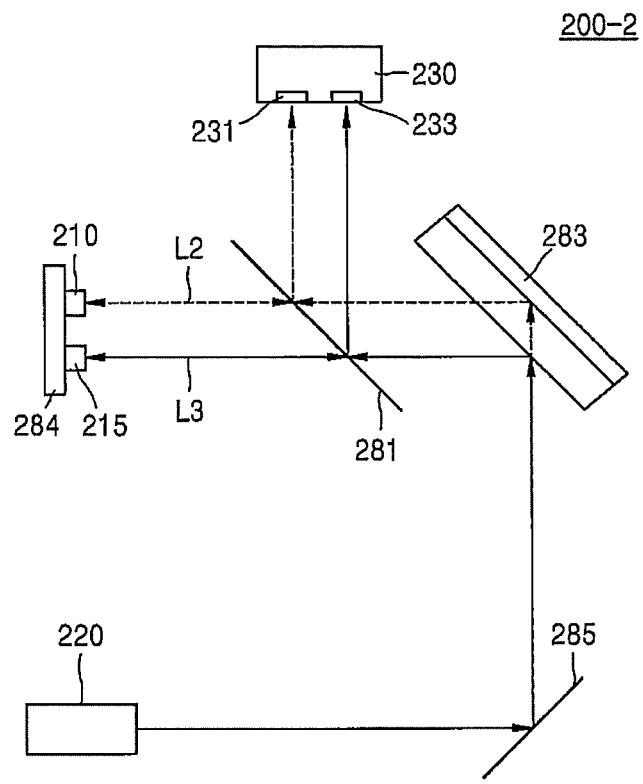
FIG. 13 is a schematic diagram of another example of the apparatus for detecting sample properties according to another embodiment.

FIG. 13 is a schematic diagram of another example of the sample property detecting apparatus 200-2 according to another embodiment.

Referring to FIG. 13, the sample property detecting apparatus 200-2 according to the embodiment may include the sample arranging portion 210, a reference sample arranging portion 215, an antibiotic applier (not shown), the wave source 220, the detector 230, the controller 240, a beam splitter 281, and a multiple beam reflector 283. The present example is the same as the above embodiment, except that the reference sample arranging portion 215 is further provided and the wave path varies accordingly, and thus, descriptions about the same components are omitted.

The sample arranging portion 210 may accommodate a sample S.

The reference sample arranging portion 215 is adjacent to the sample arranging portion 210, and may accommodate a reference sample. Here, the reference sample may include external environmental conditions to which the sample may be exposed, for example, the reference sample may include air in which the sample is placed. In other words, the reference sample may be a control group of the sample for reducing noise that may be caused by external environmental elements.

Although the antibiotic applier is not shown, the antibiotic applier may inject the antibiotic to the sample in the sample arranging portion 210.

The wave source 220 may irradiate waves to the sample in the sample arranging portion 210 and the reference sample in the reference sample arranging portion 215. Here, the multiple beam reflector 283 and the beam splitter 281 may be arranged between the wave source 220 and the sample arranging portion 210 and between the wave source 220 and the reference sample arranging portion 215. Also, a mirror 285 for changing a wave path provided from the wave source 220 may be further provided.

The multiple beam reflector 283 may split the wave incident from the wave source 220 to provide a plurality of wave paths. The multiple beam reflector 283 reflects the wave from a front surface and a rear surface thereof to provide a first wave L2 and a second wave L3 that are split in parallel with each other.

The beam splitter 281 is arranged on the plurality of wave paths provided by the multiple beam reflector 283, and may supply the first wave L2 and the second wave L3 respectively to the sample and the reference sample. After that, the beam splitter 281 may change the paths of the waves reflected and emitted from the sample and the reference sample, to provide the waves to the detector 230.

The detector 230 may detect a first laser speckle and a reference laser speckle, which are caused by multiple scattering of the waves, respectively from the sample and the reference sample, at every time point set in advance. The detector 230 may include a first detector 231 corresponding to a path of the first wave reflected from the sample, and a second detector 233 corresponding to a path of the second wave reflected from the reference sample.

The controller 240 obtains a temporal correlation of the first laser speckle by using the detected first laser speckle, and may estimate the existence of the microbes or concentration of the microbes in the sample before or after injecting the antibiotic to the sample, based on the obtained time correlation. The controller 240 may determine compatibility of the antibiotic according to the result of estimating the microbes or a variation in the concentration of the microbes. Here, the controller 240 may obtain reference information of the reference laser speckle by using the detected reference laser speckle. The controller 240 may reduce noise from the temporal correlation of the first laser speckle, by using the obtained reference information.

That is, the sample property detecting apparatus 200-2 additionally includes the reference sample arranging portion 215, and thus, the variation in the temporal correlation coefficient due to the external environment may be detected simultaneously. As such, the noise may be excluded from the temporal correlation coefficient of the actual sample, and the test may be accurately performed.

Figure 14:
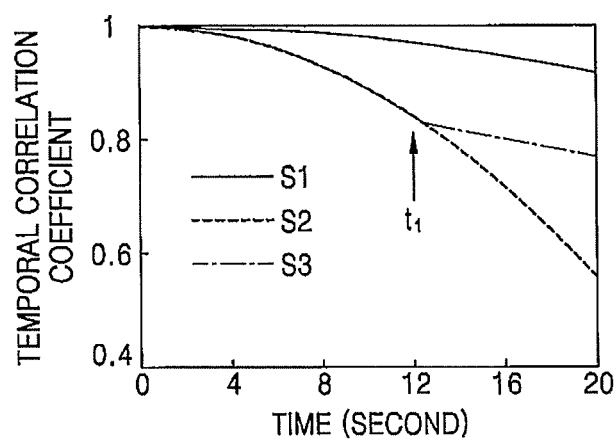
FIG. 14 is a graph schematically showing variation in a temporal correlation before and after injecting antibiotics, obtained by using the apparatus for detecting sample properties of FIG. 9.

FIG. 14 is a graph schematically showing variation in temporal correlation before and after injecting antibiotics, obtained by using the sample property detecting apparatus 200 of FIG. 9.

Figure 24:
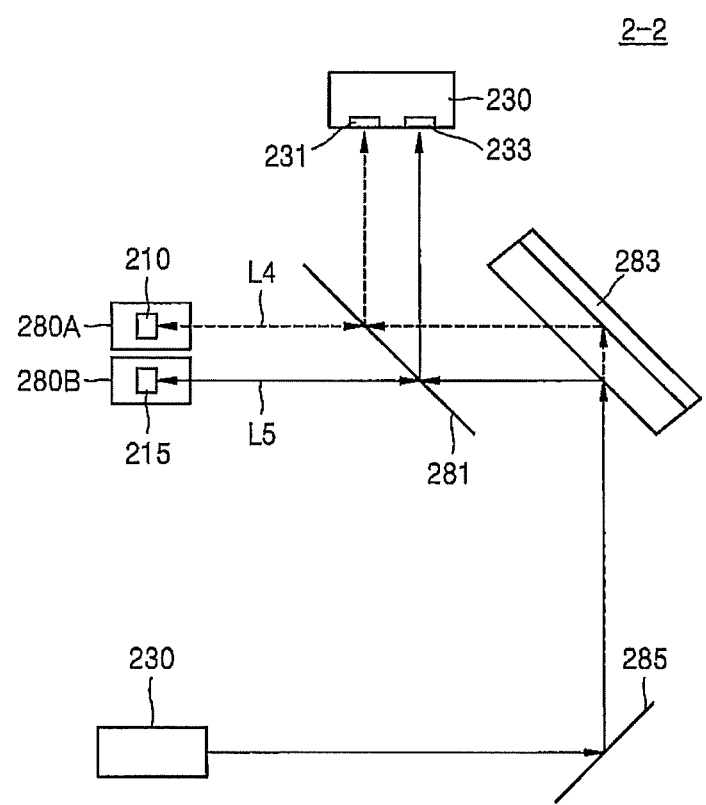
FIG. 24 is a schematic diagram of an entity discrimination apparatus according to another embodiment.

When the temporal correlation coefficient of the sample differs before and after injecting the antibiotic, the controller 240 may determine the injected antibiotic has compatibility. In the graph of FIG. 24, a solid line S1 denotes a temporal correlation coefficient of a sample in which microbes do not exist, a dashed line S2 denotes a temporal correlation coefficient of a sample in which microbes exist, and a dashed-dot line S3 denotes a temporal correlation coefficient when the antibiotic is injected. As shown in FIG. 14, the dashed-dot line S3, based on a time point t1 of injecting the antibiotic, has an inclination equal to that of the dashed line S2 before injecting the antibiotic and has an inclination equal to that of the solid line S1 after injecting the antibiotic. FIG. 14 shows an example before and after injecting the antibiotic, but actually, the dashed-dot line S3 may have an inclination value between those of the solid line S1 and the dashed line S2 after injecting the antibiotic. However, according to the variation, it may be determined whether the antibiotic is compatible with the sample S.

As described above, the sample property detecting apparatus 200 according to the embodiment is capable of estimating the existence of the microbes or concentration of the microbes rapidly with low expenses by using the variation in the temporal correlation of the laser speckle due to the microbes, and accordingly, the compatibility of the antibiotic with respect to the sample may be checked rapidly and accurately.

Hereinafter, a portable life sensing system 1 by using the microbe detecting method according to the embodiments will be described below.

Figure 15:
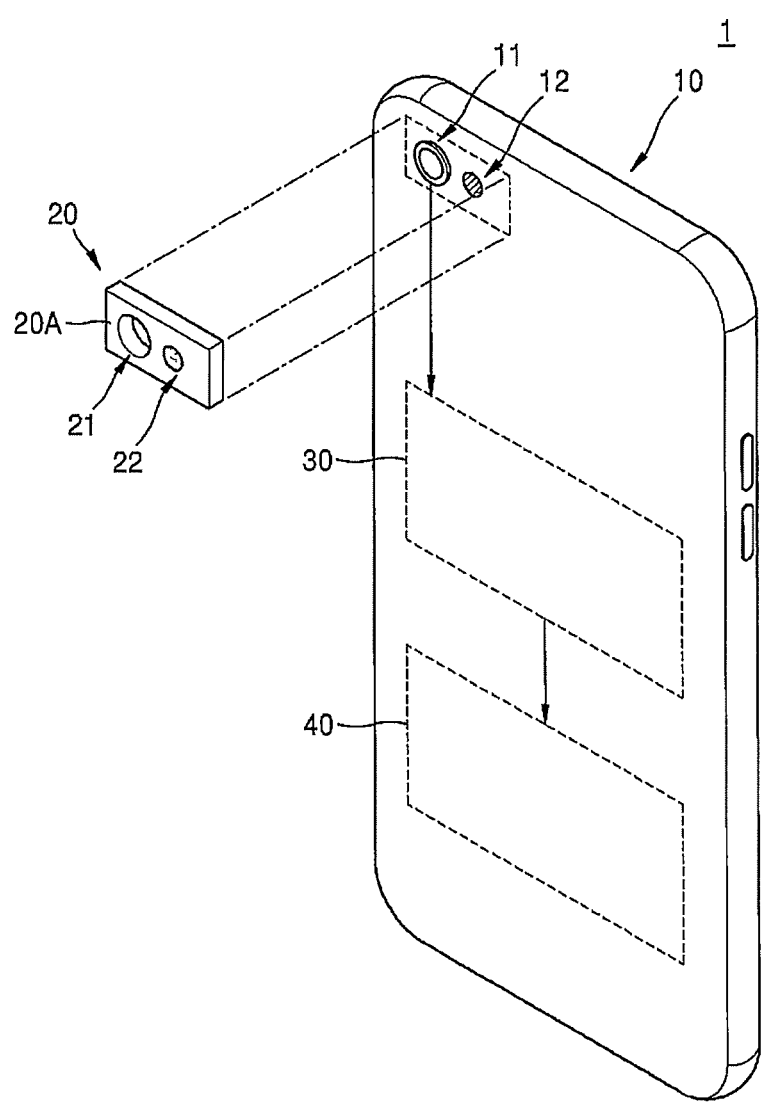
FIG. 15 is a conceptual diagram schematically showing a portable system for detecting lives, according to an embodiment.
Figure 16:
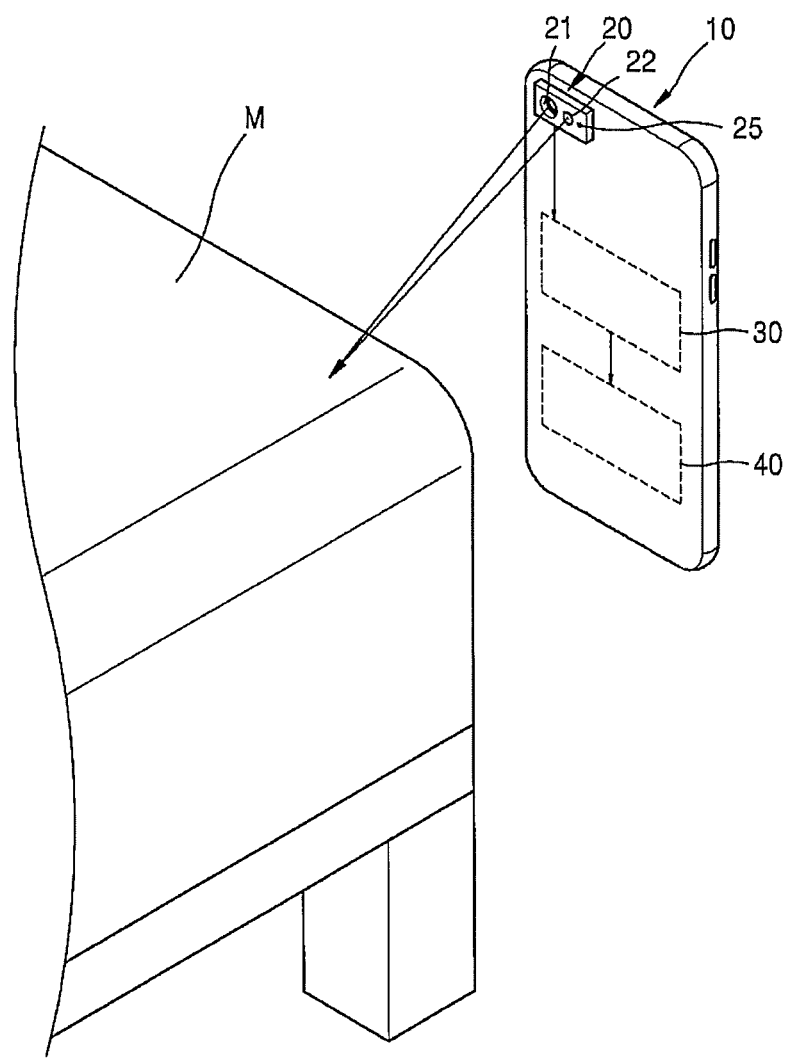
FIG. 16 is a diagram showing an example of the portable system for detecting lives of FIG. 15.

FIG. 15 is a schematic conceptual diagram of the portable life sensing system 1 according to an embodiment, and FIG. 16 is a diagram schematically showing the portable life sensing system 1 of FIG. 15 according to the embodiment.

Referring to FIG. 15, the portable life sensing system 1 according to the embodiment may include an electronic device 10, a life sensing device 20, a detector 30, and a controller 40. Here, the method for the controller 40 to detect microbes by using the laser speckle is the same as above, and thus, detailed descriptions thereof are omitted.

The electronic device 10 includes a light source 12 and a camera 11 arranged on a surface thereof, and may be a portable device. The electronic device 10 may include a display (not shown), and the above surface may face a surface in which the display (not shown) is arranged (see FIG. 15), or as another embodiment, may be equal to the surface in which the display (not shown) is arranged. As another embodiment, the electronic device 10 may include two or more light sources 12 and/or cameras 11, which may be arranged on both the surface including the display (not shown) and an opposite surface thereof. The electronic device 12 may be various kinds of portable devices that may be easily carried around, for example, a mobile phone, a tablet, a laptop computer, a graphing calculator, a portable game machine, a digital camera, a digital camcorder, a portable media player, etc.

The light source 12 is a light source used in an electronic device such as a general mobile phone and having a wide wavelength band, for example, a light source irradiating light of a total visible ray wavelength band. However, the present disclosure is not limited thereto, the light source may irradiate light of an infrared ray wavelength band, or other wavelength bands.

Although not shown in the drawing, the camera 11 may include a lens module including at least one lens and an image sensor for sensing an optical image provided to the lens module, to capture an optical image of the measurement target and generate imaging information.

In addition, the life sensing device 20 may sense existence of a life or a concentration of the lives in a state of being attached to the electronic device 10, or in a detached state from the electronic device 10. The life sensing device 20 may include a body 20A and a transformer 22.

The body 20A of the life sensing device 20 may be attached to/detached from the electronic device 10. The transformer 22 may be arranged on the body 20A, and the body 20A may be provided in various shapes for fixing the transformer 22 on a position corresponding to the light source 12 of the electronic device 10. Various embodiments of the body 20A will be described later. In addition, the body 20A may include an opening 21 for exposing the camera 11 of the electronic device 10. Since the opening 21 penetrates through the body 20A at a position corresponding to the camera 11, the camera 11 may be exposed.

The transformer 22 of the life sensing device 20 is arranged in the body 20A at a location corresponding to the wave source 120, and transforms the light irradiated from the light source 12 into a first wave of a predetermined wavelength band to irradiate the first wave into a measurement target on an outer portion. The transformer 22 is located at a location to which the light from the light source 12 is irradiated, and transforms the light into the first wave of the predetermined wavelength band to irradiate the first wave to the measurement target on the outer portion. For example, the transformer 22 may be a band pass filter. That is, the life sensing system 1 may irradiate the first wave of a certain wavelength band suitable for detecting the laser speckle via the transformer 22, and thus, may sense whether a life exist in the measurement target or a concentration of the life in the measurement target.

For example, the transformer 22 may transform the light into a spectral bandwidth having high coherence in order to form speckles on the measurement target, and when the spectral bandwidth of the irradiated light is reduced, the measuring accuracy may be improved. That is, when a coherence length increases, the measuring accuracy also increases.

In addition, the detector 30 may detect a first laser speckle at every time point set in advance, wherein the first laser speckle is generated when the first wave irradiated from the transformer 22 is multiple-scattered due to the measurement target. Here, the time point may denote one instant during continuous flow of time, and time points may be set in advance with constant time intervals therebetween, but is not limited thereto, that is, may be set in advance with an arbitrary time interval. The detector 30 may include a sensing unit corresponding to the first wave, or may use the camera 11 of the electronic device 10 without including a separate sensing unit. That is, the detector 30 may receive imaging information generated by the camera 11, and may detect the first laser speckle by using the imaging information. The detector 30 may detect the first laser speckle at the first time point at least, and may detect the first laser speckle at a second time point that is different from the first time point and provide the first laser speckle to the controller 40. The first time point and the second time point are just examples selected for convenience of description, and the detector 30 may detect laser speckles at a plurality of time points more than the first and second time points.

In detail, the method of detecting the first laser speckle in the detector 30 will be described with reference to FIG. 16.

Referring to FIG. 16, when the first wave is irradiated to a measurement target M, the first wave may generate the first laser speckle due to the multiple scattering. Here, the measurement target M may be any kind including a medium capable of forming chaotic waves. For example, as shown in FIG. 2, any kind of material that a human being may contact, for example, a mattress, a sofa, a cutting board, a desk, a door knob of a bathroom, a keyboard, etc., may be a measurement target, unless the material is a medium having regular reflectivity such as metal. In addition, the body part of a human being such as a tooth or a fingernail may be a measurement target. The laser speckle is generated by the light interference effect, and thus, when there is no motion in the measurement target, a constant interference pattern may be shown according to time. Compared to this, when a life such as bacteria, germs, mites, etc. exists in a measurement target M, the laser speckle may vary according to time due to the movement of the life. The detector 30 detects the laser speckle varying according to time at every time point set in advance, to provide the laser speckle to the controller 40. The detector 30 may detect the laser speckle at a sufficient speed to sense the movement of the life, for example, 25 frames to 30 frames per second.

In addition, when the medium is a liquid such as milk or purified water, the laser speckle may not be detected due to fluidity of the medium. Here, the life sensing system 1 according to the embodiment may further include a medium filter (not shown) that filters the medium, that is, liquid, and then, may detect the laser speckle by using the medium filter (not shown) including residual after filtering the medium as a measurement target. As such, existence of a life or a concentration of the life in the measurement target M such as a liquid, from which the laser speckle may not be detected, may be estimated.

In addition, the controller 40 may obtain a temporal correlation by using the first laser speckle, and may estimate in real-time the existence of the life or the concentration of the life in the measurement target M based on the obtained temporal correlation. In the present specification, real-time denotes estimating whether a life exists or estimating variation in concentration of the life within one hour, for example, the existence of the life or the variation in the concentration of the life may be estimated within five minutes. In detail, the existence of the life or the variation in concentration of the life may be estimated within twenty (20) seconds. The controller 40 may operate to provide a user with a result of estimating the existence of the life and a result of estimating the variation in the concentration of the life through a display (not shown) of the electronic device 10. The method of estimating the existence of the microbes or the variation in the concentration of microbes, performed by the controller 40, will be described later.

Here, the controller may include all kinds of devices capable of processing data, e.g., a processor. Here, the 'processor' may denote, for example, a data processing device built in hardware, and includes a physically structured circuit for executing functions expressed as codes or commands included in a program. As an example of the data processing device built into the hardware, a microprocessor, a central processing unit (CPU), a processor core, a multi-processor, an application-specific integrated circuit (ASIC), a field programmable gate array (FPGA), etc. may be used, but the scope of the present disclosure is not limited thereto.

In FIGS. 15 and 16, the controller 40 is arranged in the electronic device 10, but the present disclosure is not limited thereto. The controller 40 may be arranged in the life sensing device 20, or may be arranged in an external server (not shown) communicating with the electronic device 10 and the life sensing device 20. However, a case in which the controller 40 is arranged in the electronic device 10 will be described for convenience of description. Here, the controller 40 may implement the above-described operations by driving an application program or an application stored on a memory (not shown) of the electronic device 10.

In addition, the life sensing system 1 according to the embodiment estimates the existence of the life or the variation in the concentration of the life by using the temporal correlation of the first laser speckle, but variation in the laser speckle caused by other elements than the temporal correlation may apply as noise. In order to remove the noise, the life sensing system 1 may reduce noise caused by shivering hands of the user, by further providing an image stabilization function in the device in which the detector 30 is arranged, that is, the electronic device 10 according to the embodiment.

Also, the life sensing system 1 may provide the user with a reference focal length between the measurement target M and the life sensing device 20 in order to accurately detect the first laser speckle. As another embodiment, the life sensing system 1 may further include a distance sensor 25 for measuring a distance between the measurement target M and the life sensing device 20, and the distance sensor 25 may be arranged on the body 20A of the life sensing device 20. The distance sensor 25 measures the distance between the life sensing device 20 and the measurement target M, and may transfer information about the distance to the controller 40. The controller 40 determines whether the distance measured by the distance sensor 25 is included in a range set in advance, and may generate a first signal when the distance is included in the range set in advance. Here, the detector 30 may be configured to operate when receiving the first signal from the controller 40, and thus, the detector 30 may automatically detect the first laser speckle when a focus is adjusted.

Figure 17A:
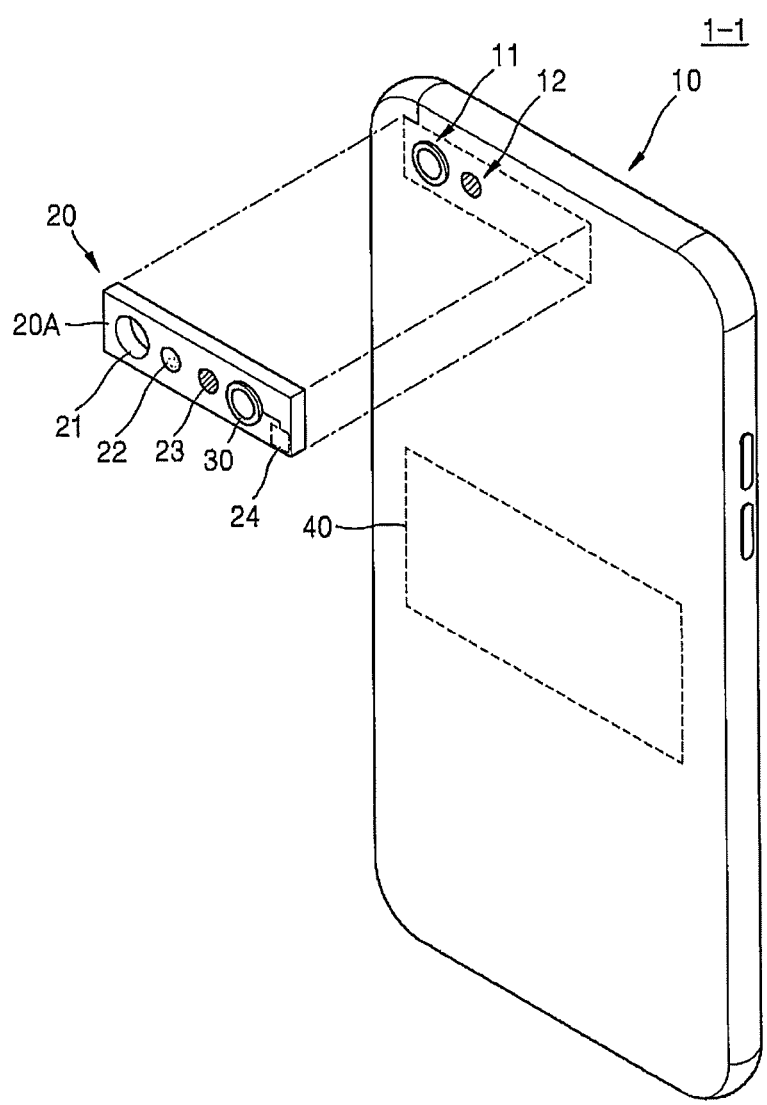
FIG. 17A and FIG. 17B are conceptual diagrams schematically showing a system for detecting lives according to another embodiment.
Figure 17B:
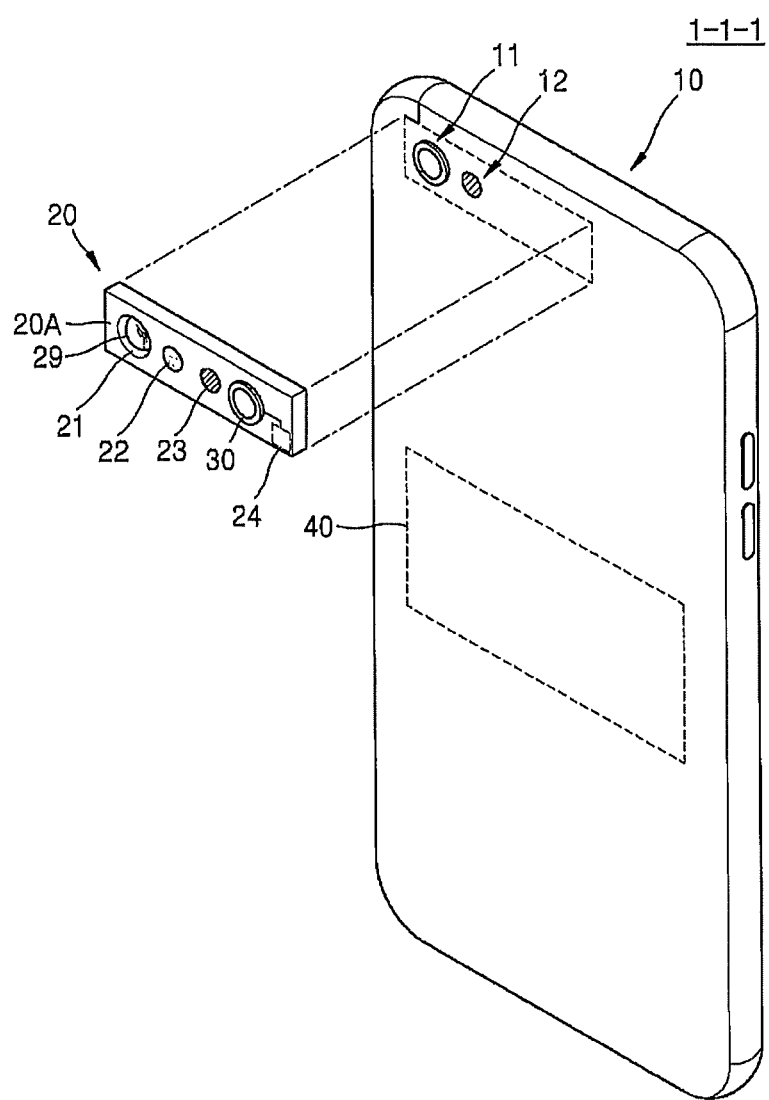

FIGS. 17A and 17B are conceptual diagrams schematically showing a life sensing system 1-1 according to another embodiment, and FIGS. 18A to 18D are exemplary diagrams schematically showing various examples of the body 20A of the life sensing device 20 of FIGS. 17A and 17B.

Referring to FIG. 17A, the life sensing system 1-1 according to the embodiment may include the electronic device 10, the life sensing device 20, the detector 30, and the controller 40. In the descriptions about FIGS. 17A and 17B, components that are the same as or corresponding to those of the life sensing system 1 of FIGS. 1 and 2 are denoted by the same reference numerals, and descriptions thereof will be omitted.

The electronic device 10 may be a portable device including a light source 12 and a camera 11 arranged on a surface thereof.

The life sensing device 20 according to another embodiment includes the body 20A and the transformer 22, and may further include a wave source portion 23 that is independently provided to sense lives even in a state of being detached from the electronic device 10, as well as being attached to the electronic device 10.

Figure 18A:
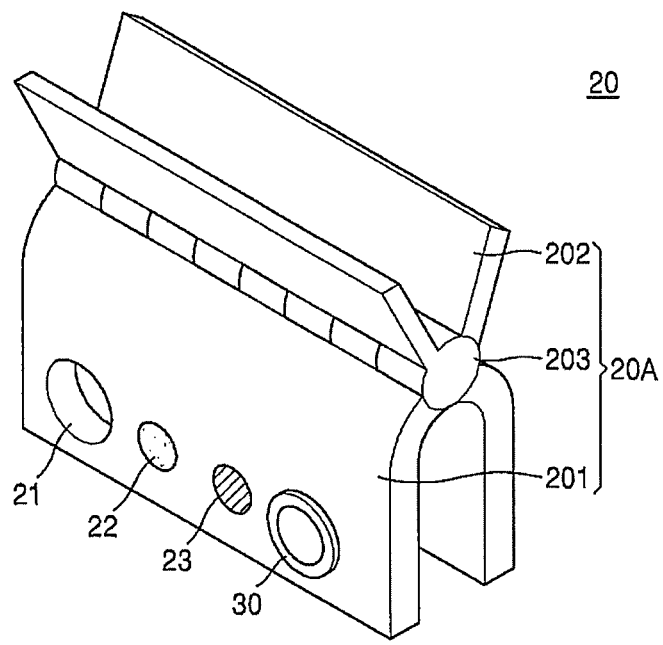
FIG. 18A, FIG. 18B, FIG. 18C, and FIG. 18D are schematic diagrams showing various examples of a body in the system for detecting lives of FIG. 17A and FIG. 17B.

The body 20A may be attached to/detached from the electronic device 10. Referring to FIG. 18A, the body 20A may be formed as tongs to be mounted at a side of the electronic device 10. The body 20A may include a main body 201 in which the opening 21, the transformer 22, and the wave source portion 23 are arranged, a grip 202 connected to the main body 201, and a hinge 203 having elasticity and connected between the main body 201 and the grip 202, and thus, may be attached to/detached from the electronic device 10 by a pressure applied to the grip 202. In addition, referring to FIG. 17B, the body 20A may further include a macro lens 29 overlapping with the opening 21 which corresponds to the camera 11 of the electronic device 10. Since the body 20A includes the macro lens 29 to reduce a focal length, the camera 11 of the electronic device 10 may detect the laser speckle from a region A1 (see FIG. 3) that is spaced apart from the surface of the sample S. Also, the body 20A may further include a screen (not shown), on which an image of the wave proceeding after being multiple-scattered by the sample S may be focused, at a location corresponding to the focal length of the macro lens 29. Here, the screen (not shown) may include a semi-transmission material through which the wave multiple-scattered from the sample S may transmit.

Figure 18B:
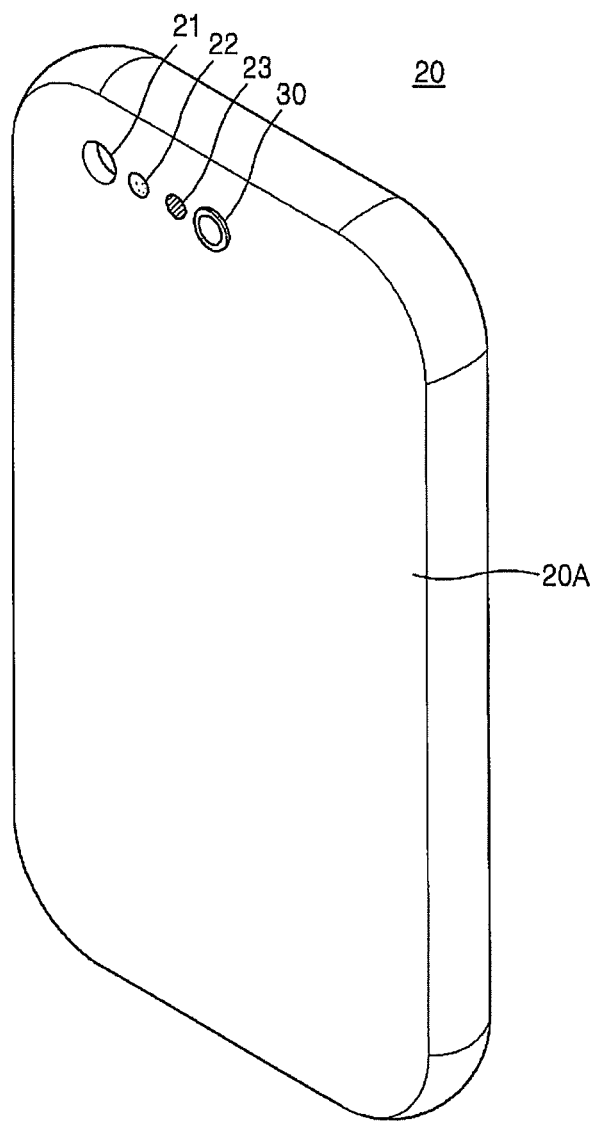
Figure 18C:
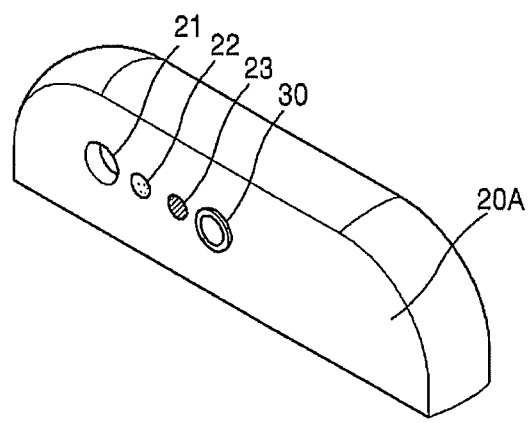
Figure 18D:
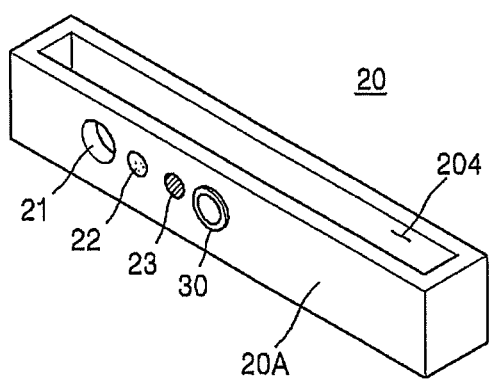

As another embodiment, the body 20A may be configured as a case that may be at least partially mounted on the electronic device 10. In detail, the body 20A may be formed as a case mounted at least partially on a surface of the electronic device 10, in which the light source 12 and the camera 11 are arranged. As shown in FIG. 18B, the body 20A may be provided as a case mounted entirely on a surface of the electronic device 10, and as shown in FIG. 18C, the body 20A may be at least partially covered on a surface in which the light source 12 and the camera 11 are located. Also, as shown in FIG. 18D, the body 20A may include an insertion hole 204 that penetrates through a center of the body 20A in parallel with the surface, in which the opening 21 and the transformer 22 are arranged, and the body 20A may be attached and detached by inserting the electronic device 10 to the insertion hole 204. The body 20A is not limited to the above example, and various embodiments attached to/detached from the electronic device 10 may be applied. As another embodiment, the body 20A may be attached to/detached from the electronic device 10 by applying an adhesive to a contact surface that contacts the electronic device 10.

Referring back to FIGS. 17A and 17B, the wave source portion 23 may irradiate a second wave towards the measurement target M. The wave source portion 23 may include all kinds of source devices capable of generating waves, for example, may be a laser irradiating light of a certain wavelength band. Although the present disclosure is not limited to the kind of wave source, for convenience of description, a case where the wave source is a laser will be described below.

For example, the laser having excellent coherence may be used as the wave source in order to form speckles on the measurement target M. Here, when a spectral bandwidth of the wave source is shorter, a measuring accuracy may increase, wherein the spectral bandwidth determines the coherence of the laser wave source. That is, when a coherence length increases, the measuring accuracy also increases. Accordingly, a wave source irradiating the laser having a spectral bandwidth that is less than a reference bandwidth set in advance may only be used as the wave source portion 23, and when the spectral bandwidth is reduced to be less than the reference bandwidth, the measuring accuracy may increase. For example, the spectral bandwidth of the wave source portion 23 may be set to satisfy the condition of Equation 1 above.

According to Equation 1 above, when the light is irradiated into the measurement target at every reference time in order to measure a variation in the laser speckle pattern, the spectral bandwidth of the wave source portion 23 may be maintained to be less than 1 nm.

In order for the life sensing device 20 according to another embodiment to separately operate from the electronic device 10, the detector 30 may be arranged at least in the life sensing device 20.

The detector 30 may include a sensing unit corresponding to the kind of the wave source portion 23, for example, a CCD camera that is an imaging device in a case where a light source of a visible ray wavelength band is used. The detector 30 may detect the laser speckle at a first time point at least, and may detect the laser speckle at a second time point, and then, may provide the controller 40 with the detected laser speckles. Here, the controller 40 may be arranged in the life sensing device 20 to perform the above-described operations. As another embodiment, the controller 40 may be arranged in the electronic device 10 as in the above-described embodiment. The location of the controller 40 is not limited thereto, and a case in which the controller 40 is arranged in the electronic device 10 will be described for convenience of description. When the controller 40 is arranged in the electronic device 10, the life sensing device 20 may further include a communicator 24 communicating with the electronic device 10 through wires or wirelessly, and may transfer the detected laser speckle to the controller 40. The communicator 24 may include hardware and software that is necessary for transmitting/receiving a signal such as a data signal via wired/wireless connection to the electronic device 10.

In addition, in a case where an image sensor is used as the detector 30, the image sensor may be arranged so that a side d of one pixel in the image sensor is equal to or less than a grain size of the speckle pattern. For example, the detector 30 may include an image sensor satisfying the condition of Equation 2 above.

As expressed by Equation 2 above, the size d of one pixel in the image sensor has to be equal to or less than the grain size of the speckle pattern, but the size of the pixel is too small, and thus, an undersampling may occur and it may be difficult to utilize the pixel resolution. Accordingly, in order to achieve an effective signal to noise ratio (SNR), the image sensor may be arranged to make five or less pixels correspond to the speckle grain size.

The detector 30 may detect a second laser speckle that is generated when a second wave irradiated from the wave source portion 23 is multiple-scattered by the measurement target in a state where the life sensing device 20 is separated from the electronic device 10. Also, the detector 30 may detect the first laser speckle that is generated when the first wave irradiated from the light source 12 of the electronic device 10 and transformed is multiple-scattered by the measurement target, in a state where the life sensing device 20 is attached to the electronic device 10, and at this time, the second laser speckle caused by the second wave may also be detected. In other words, the detector 30 may select and detect at least one of the first laser speckle and the second laser speckle.

In addition, the controller 40 may obtain a temporal correlation of the first laser speckle or the second laser speckle by using the detected first laser speckle or the second laser speckle, and may estimate in real-time existence of the life or a concentration of the life in the measurement target based on the obtained temporal correlation.

Figure 19A:
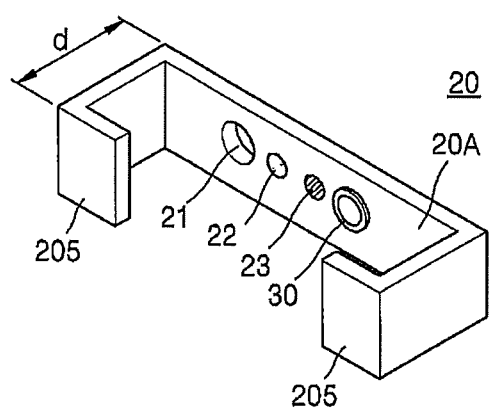
FIGS. 19A and 19B are conceptual diagrams schematically showing an apparatus for detecting lives according to another embodiment.
Figure 19B:
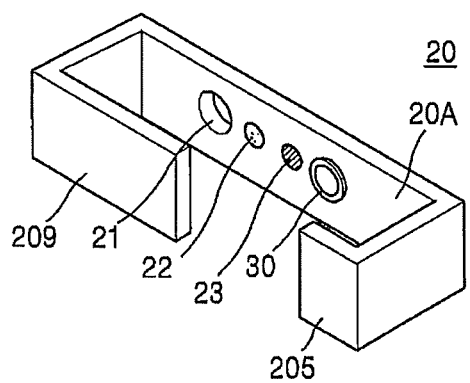
Figure 20:
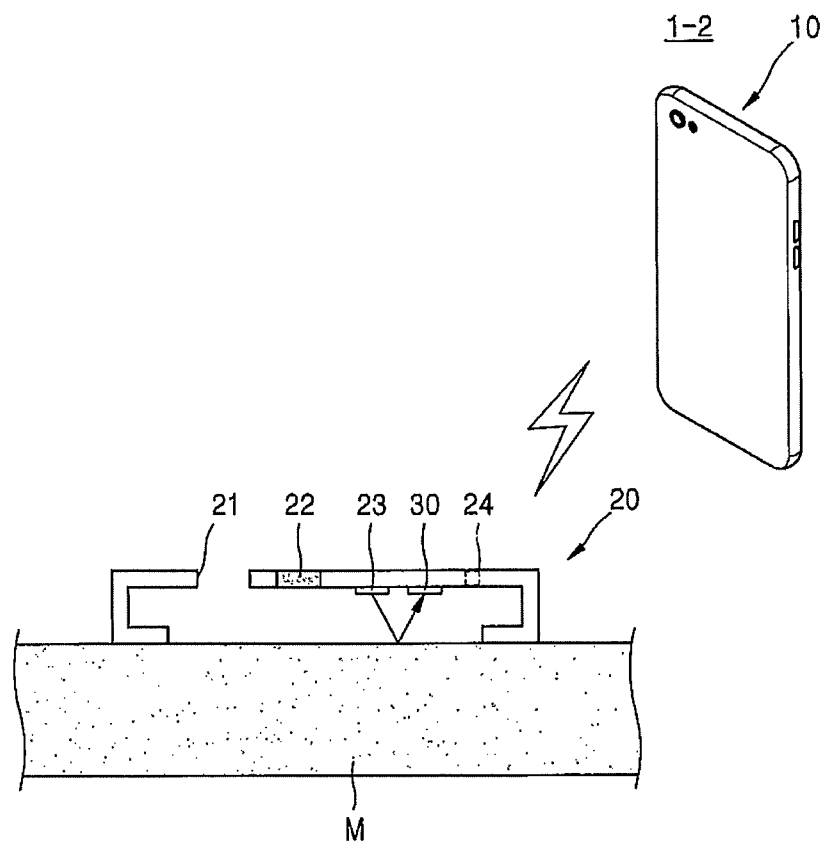
FIG. 20 is a schematic conceptual diagram of an example of a system for detecting lives including the apparatus for detecting lives of FIG. 19A and FIG. 19B.

FIGS. 19A and 19B are conceptual diagrams schematically showing the life sensing device 20 according to another embodiment, and FIG. 20 is a conceptual diagram schematically showing a life sensing system 1-2 including the life sensing device 20 of FIGS. 19A and 19B. In the descriptions about FIGS. 19A to 20, components that are the same as or corresponding to those of the life sensing system 1 of FIGS. 15 and 16 are denoted by the same reference numerals, and descriptions thereof will be omitted.

Referring to FIGS. 19A and 20, the life sensing device 20 may further include a supporter 205 extending from the body 20A to a preset length L towards the measurement target M from the transformer 22. As described above, the life sensing system 1-2 according to the embodiment estimates the existence of the life or the variation in the concentration of the life by using the temporal correlation of the first laser speckle, but variation in the laser speckle caused by other elements than the temporal correlation may apply as noise. The supporter 205 may support the life sensing device 20 to be stably located on the measurement target M, and moreover, may maintain the focal length L of the detector 30, thereby accurately detecting the laser speckle. Also, in FIG. 20, the life sensing device 20 is separated from the electronic device 10, but the measurement may be performed in a state where the life sensing device 20 is attached to the electronic device 10.

Referring to FIG. 19B, the life sensing device 20 may further include a reference measuring portion 209 for providing a reference value of the first laser speckle or the second laser speckle that is multiple-scattered by the measurement target M. The reference measuring portion 209 is located to correspond to the opening 21 and the transformer 22, and may be spaced from the opening 21 and the transformer 22 by a length L between the measurement target M and the detector 30 of the life sensing device 20. As shown in the drawings, the reference measuring portion 209 may extend from the supporter 205 described above, but is not limited thereto. Also, the reference measuring portion 209 may be arranged to correspond to the opening 21 and the transformer 22, or to correspond to the wave source portion 23 and the detector 30. That is, the reference measuring portion 209 measures a stabilized medium in order to provide a reference value of the measured laser speckle. When the life sensing device 20 is classified as two units irradiating and detecting the waves, one unit may measure the laser speckle from the measurement target and the other unit may measure the reference laser speckle of the reference measuring portion 209. As such, the life sensing device 20 may perform the measuring operation precisely, by excluding the noise caused by the movement or external environment.

Figure 21A:
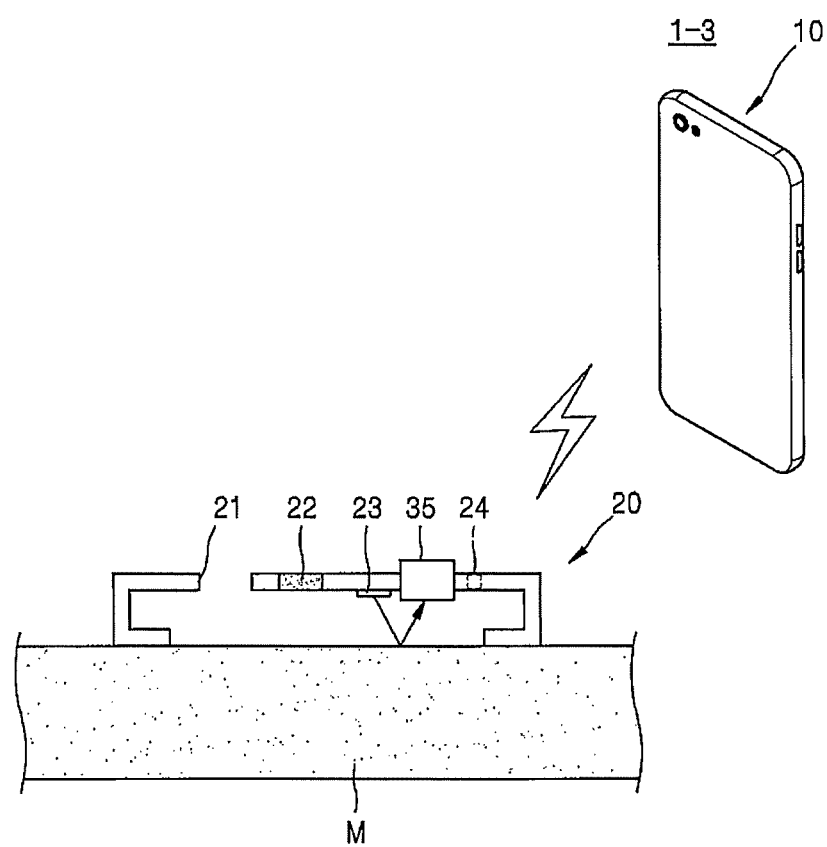
FIGS. 21A and 21C are conceptual diagrams schematically showing a system for detecting lives according to another embodiment.
Figure 21B:
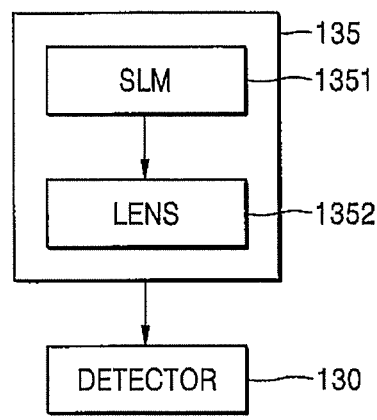
FIG. 21B is a block diagram schematically showing an optical portion of FIG. 21A.
Figure 21C:
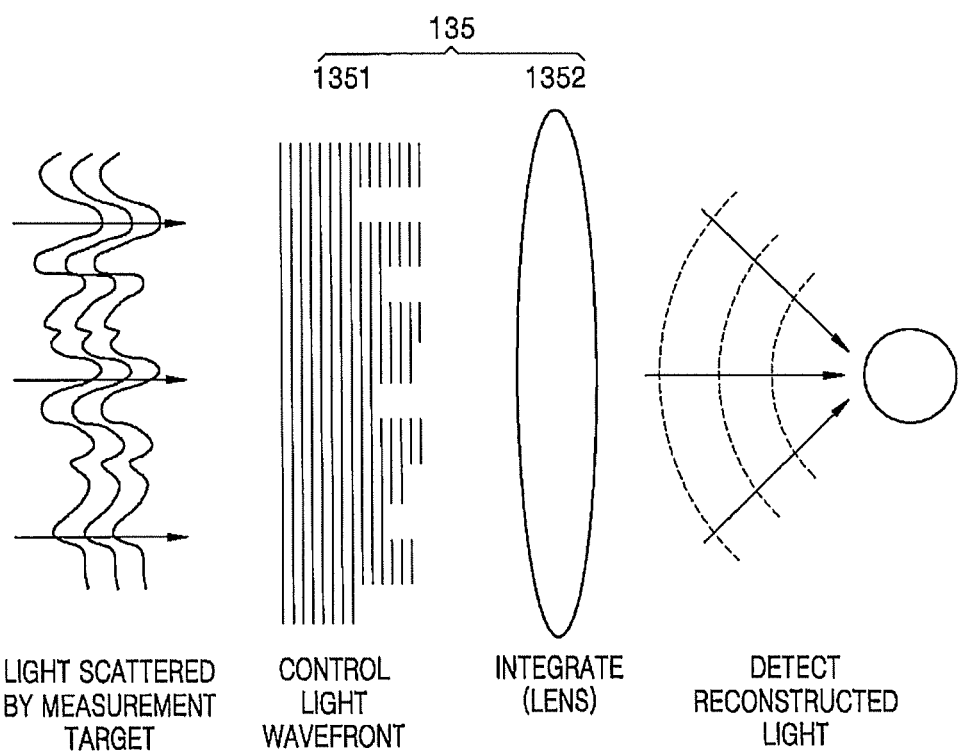

FIGS. 21A and 21C are conceptual diagrams schematically showing a life sensing system 1-3 according to another embodiment, and FIG. 21B is a block diagram schematically showing an optical portion 35 of FIG. 21A.

Referring to FIGS. 21A to 21C, the life sensing system 1-3 may further include the optical portion 135 that senses the first optical signal scattered by the measurement target M and reconstructs the first optical signal into a second optical signal before being scattered. Here, the optical portion 135 may include an SLM 1351 and a lens 1352. When the scattered light is incident to the optical portion 135 from the measurement target M, the optical portion 135 may reconstruct the scattered light into the light before being scattered and provides the reconstructed light to the detector 30.

The first optical signal scattered by the measurement target M may be incident to the SLM 1351. The SLM 1351 may control the scattered wave and then may provide the wave to the lens 1352. The lens 1352 may integrate the first optical signal provided from the SLM 1351, and reconstruct the second optical signal that is an original signal before being scattered and output the reconstructed signal.

Here, the optical portion 135 may reconstruct the first optical signal scattered by the measurement target M into the light before being scattered, in a case where there is no movement of a life in a stabilized medium, that is, the measurement target M. However, in a case where a life exists in the measurement target, the first optical signal varies due to movement of the life, a phase control wave front may not be sensed, and accordingly, the first optical signal may not be modulated into a second optical signal having an optical phase conjugate wave front. The life sensing system 1 including the optical portion 135 may accurately estimate the existence of the life or the concentration of the life by using the variation in the second optical signal.

In addition, as another embodiment, the optical portion 135 may further include an optical unit such as a mirror or a beam splitter that may change the paths of the first optical signal and the second optical signal.

As described above, the life sensing device and the life sensing system including the same according to the embodiments of the present disclosure may rapidly estimate whether a life exists or a concentration of the life with low expenses and provide a result to the user, by using a variation in the temporal correlation of the laser speckle caused by the life in the measurement target. As such, the user may directly identify the contamination state of peripheral environment, which is not visible. Also, the life sensing system may perform the measurement anywhere regardless of the location of the measurement target by using the life sensing device that is attachable to/detachable from the portable electronic device, thereby providing user convenience.

Hereinafter, an entity identifier 2 using the microbe detecting method according to the embodiments will be described below.

Figure 22:
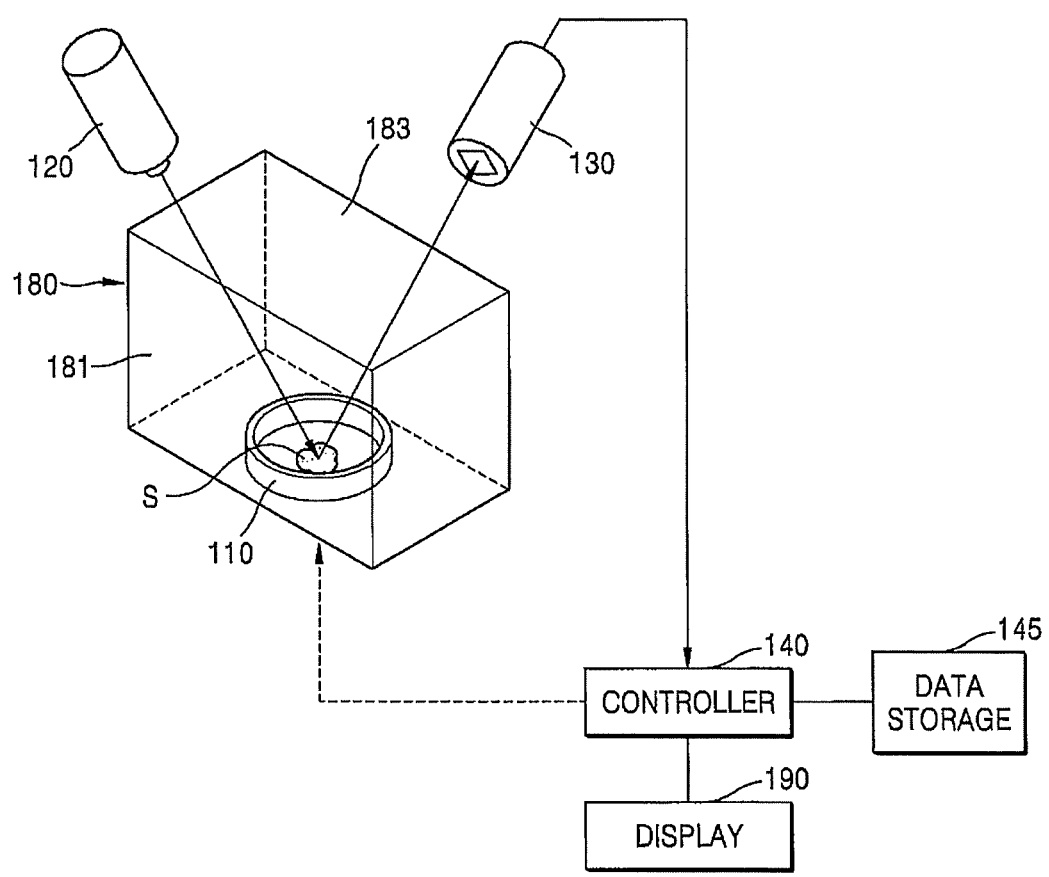
FIG. 22 is a schematic conceptual diagram of an entity discrimination apparatus according to an embodiment.
Figure 23:
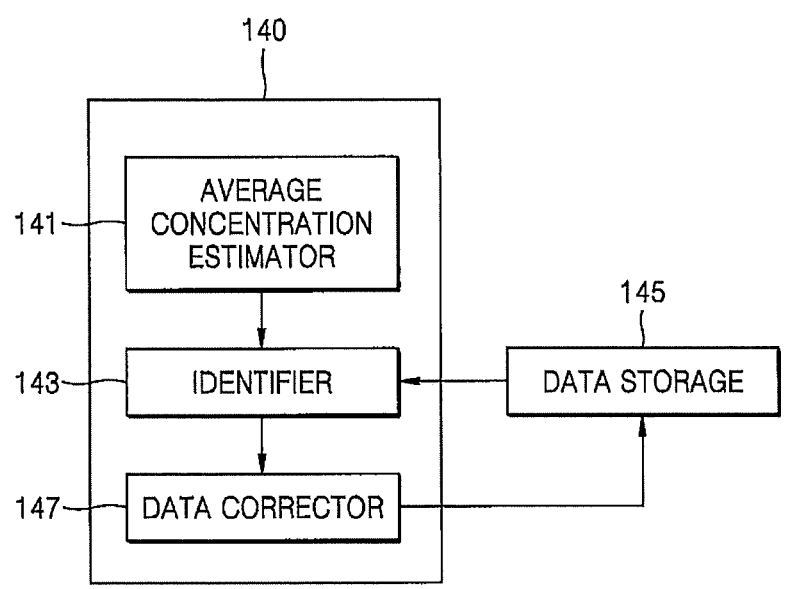
FIG. 23 is a block diagram schematically showing a relationship between a controller and a data storage of FIG. 22.

FIG. 22 is a conceptual diagram schematically showing the entity identifier 2 according to an embodiment, and the FIG. 23 is a schematic block diagram showing the relationship between a controller 140 and a data storage 145 of FIG. 22.

Referring to FIG. 22, the entity identifier 2 according to the embodiment may include a sample arranging portion 110, an environmental chamber 180, a wave source 120, one or more detectors 130, and the controller 140. Also, the entity identifier 2 may further include the data storage 145 and a display 190.

The sample arranging portion 110 may accommodate a sample S taken from a target entity. Here, the sample S may include saliva, blood, or tissues of the target entity, or stool, urine, or dead skin cells discharged out of the target entity. The sample S may be taken when the entity blows or is taken from the skin of the target entity, or may be taken by filtering stool, etc. Microbes existing in the body also exist in the sample S. If a human being snores, burps, or farts, the microbes in the body are discharged out of the body, and thus, the sample S for identifying the target entity may be taken in various ways. As another embodiment of taking the sample S, the target entity moves in a clean room for a predetermined time period, and then, the sample S including microbes may be taken from an air filter arranged in the clean room. The sample S may be entirely used, or may be prepared by using a unit to which microbes may be transferred, for example, a tape, a membrane, etc.

The environmental chamber 180 accommodates the sample arranging portion 110 therein, and may change environmental condition surrounding the sample S. The environmental chamber 180 may change at least one of conditions including temperature, humidity, pressure, magnetic field, whether to inject antibiotic, and a kind of antibiotic. In detail, the environmental chamber 180 may change the above environmental conditions by using a temperature adjusting device, a humidity adjusting device, a magnetic field adjusting device, etc. However, the above environmental conditions are examples, and are not limited the above examples. As another embodiment, the environmental chamber 180 may further include an antibiotic injection device that may inject one or more kinds of antibiotics. Also, in addition to the above environmental conditions, various environmental conditions affecting the microbes in the sample S may be applied. The environmetal chamber 180 may be controlled by the controller 140.

A shape of the environmental chamber 180 is not restricted, and the environmental chamber 180 may include a material and a structure that is not affected by an outer environment of the environmental chamber 180. For example, the environmental chamber 180 may include a heat-insulation material in order to maintain a constant temperature therein. Also, the environmental chamber 180 may have a pressure-resistant structure that may bear a predetermined pressure.

In addition, the environmental chamber 180 may have a surface 181 that is transparent on a path through which the wave is irradiated from the wave source 120. When the wave source 120 is arranged on an outer portion of the environmental chamber 180, the environmental chamber 180 may have at least one transparent surface 181 in order to transfer the wave irradiated from the wave source 120 to the sample S. As another embodiment, the environmental chamber 180 may have an opposite surface 183 including a diffusion material for diffusing the wave, wherein the opposite surface 183 is arranged on the path through which the wave is irradiated from the wave source 120. The above-described chaotic wave sensor may detect a laser speckle that is generated due to multiple scattering caused by the movement of the microbes in the sample S. Here, when the opposite surface 183 of the environmental chamber 180 includes a diffusion material, the multiple scattering effect due to the movement of the microbes may be increased more. As another embodiment, the opposite surface 183 of the environmental chamber 180 includes a multiple scattering material in order to amplify the number of multiple scattering of the wave in the sample S.

The wave source 120 may irradiate the wave towards the sample S in the sample arranging portion 110. The wave source 120 may include all kinds of source devices capable of generating waves, for example, may be a laser irradiating light of a certain wavelength band. Although the present disclosure is not limited to the kind of wave source, for convenience of description, a case where the wave source is a laser will be described below. For example, the laser having excellent coherence may be used as the wave source 120 in order to form speckles on the sample arranging portion 110.

Referring back to FIG. 22, the detector 130 may detect the laser speckle that is generated by the multiple scattering of the irradiated wave due to the sample S at every predetermined time point.

The controller 140 may estimate concentration of the microbes in the sample S by using the detected laser speckle, before and after the environmental condition is changed. The controller 140 may identify the target entity from among a plurality of entities by using a difference between the estimated concentrations of the microbes before and after the environmental condition is changed. The microbes may exist in or out of the entity, and kinds of the microbes may vary according to the entities. In other words, kinds of the microbes coexisting with the entity may be a piece of discrimination information by which the entity may be identified, like genes or fingerprints of the entity. However, microbes such as bacteria are not visible, and thus, it is difficult to analyze what kinds of microbes are included in the sample taken from the entity. Genes of the microbes included in the sample S taken from the entity may be analyzed, but complicated analyzing processes have to be performed like processes of analyzing genes of the entity.

According to the embodiment, the laser speckle that is generated due to the multiple scattering by the microbes in the sample S is used, and thus, simple and rapid analyzing processes may be performed. One or more kinds of microbes may exist in the sample S taken from the entity. The concentration of the microbes may change differently according to the kind or the environmental condition. According to the present disclosure, an average concentration variation of the one or more kinds of microbes according to the change of the environmental condition is used, without classifying the concentrations according to the kinds of the microbes, and the target entity may be identified from among a plurality of entities.

Referring to FIG. 23, the controller 140 may include an average concentration estimator 141, an identifier 143, and a data corrector 147.

The average concentration estimator 141 may receive the laser speckle detected by the detector 130, obtains the temporal correlation of the detected laser speckle, and estimate an average concentration of one or more kinds of microbes included in the sample S based on the obtained temporal correlation. The average concentration estimator 141 may estimate a first average concentration of the microbes before changing the environmental condition of the sample S, that is, in a case where a first environmental condition is applied to the sample S. Also, the average concentration estimator 141 may estimate a second average concentration of the microbes after changing the environmental condition of the sample S, that is, in a case where a second environmental condition that is different from the first environmental condition is applied to the sample S. Here, the first and second environmental conditions may include at least one of the temperature, the pressure, the magnetic field, and the humidity, as described above. Here, when only one kind of the environmental condition is changed, the other environmental conditions have to be fixed as constants, and then, the variation in the average concentration variation due to the difference between the first and second environmental conditions may be exactly identified. As another embodiment, when two or more environmental conditions are to be changed, the environmental conditions are sequentially changed with respect to one sample S, or the environmental conditions are respectively changed with respect to two or more samples S to estimate the concentration.

The identifier 143 generates discrimination data of the target entity by calculating a variation rate of the average concentration of the microbes according to the change of the environmental condition, and may identify the target entity from among the plurality of entities by using the discrimination data. The identifier 143 may generate the discrimination data by calculating a difference between the first average concentration according to the first environmental condition and the second average concentration according to the second environmental condition. For example, when the first environmental condition is a temperature of 30° C., the first average concentration of the microbes in the sample S is estimated to be 40%, and when the condition is changed to the second environmental condition, that is, a temperature of 60° C., the second average concentration of the microbes in the sample S may be changed to 20%. Here, the target entity has a kind of microbe having a characteristic that 20% in average becomes extinct due to the change in the temperature. Such above characteristic may be the discrimination information that the target entity only has.

The entity identifier 2 according to the embodiment may further include the data storage 145, in which reference data about the variation rate in the average concentration of the microbes according to the change in the environmental condition is stored in advance, corresponding to each of the plurality of entities. The identifier 143 may compare the discrimination data with the reference value to identify the target entity from among the plurality of entities.

As another embodiment, the identifier 143 may generate discrimination data respectively from two different samples S, may compare the discrimination data, and may determine that two samples are taken or discharged from an identical entity.

As another embodiment, in a case where the target entity is acknowledge in advance, the identifier 143 may compare the discrimination data of the target entity with the reference data stored in the data storage 145 to determine health condition of the target entity. In detail, the data storage 145 stores reference data for each entity, and the reference data may include an average concentration value of the microbes under a predetermined environmental condition, as well as the average concentration variation rate of the microbes according to the change of the environmental condition. In a case where the target entity is already known, it may be determined that the target entity is healthy when the discrimination data taken from the sample S is included in an error range set in advance with respect to the average concentration value under a predetermined environmental condition. On the contrary, when the discrimination data taken from the sample S exceeds the error range set in advance with respect to the average concentration value, it may be determined that the target entity is not healthy. The entity identifier 2 according to the embodiment may monitor the health of the target entity by using the discrimination data of the sample S that is regularly taken from the target entity.

In addition, when there is no reference data to be compared with in the data storage 145, the data corrector 147 may convert the discrimination data of the target entity S generated by the identifier 143 into reference data and store the generated reference data in the data storage 145. The entity identifier 2 may establish a database of the reference data with respect to a plurality of entities by using the data corrector 147. Also, the data corrector 147 may correct the reference data by using the discrimination data, in a case where the reference data stored in the data storage 145 has an error.

Referring back to FIG. 22, the controller 140 may determine the target entity in real-time from among the plurality of entities by using the variation rate of the estimated average concentration of the microbes. In the present specification, 'real-time' denotes identifying of the target entity by using the variation rate of the average concentration of the microbes within one hour, for example, within 5 minutes. In more detail, the target entity may be identified within 20 seconds.

In addition, the entity identifier 2 may further include the display 190. The display 190 may display the variation rate of the average concentration of the microbes estimated by the controller 140, and a result of identifying the target entity.

FIG. 24 is a schematic diagram of an entity discrimination apparatus 2-2 according to another embodiment.

Referring to FIG. 24, the entity discrimination apparatus 2-2 according to another embodiment may include a sample arranging portion 210, a reference sample arranging portion 215, an environmental chamber 280A, a reference chamber 280B, a wave source 220, a detector 230, and a controller 240. Also, the entity discrimination apparatus 2-2 may further include an optical unit such as a beam splitter 281 and a multiple beam reflector 283. The entity discrimination apparatus 2-2 according to the embodiment is the same as that of the previous embodiment, except that the reference sample arranging portion 215 and the reference chamber 280B are further provided, and detailed descriptions about the same elements are omitted.

The sample arranging portion 210 may accommodate a sample taken from a target entity.

The reference sample arranging portion 215 may accommodate the reference sample. The sample arranging portion 210 is accommodated in the environmental chamber 280A, in which the environmental condition changes, and the reference sample arranging portion 215 may be accommodated in the reference chamber 280B, in which the environmental condition does not change. Here, the reference sample is the same as the sample taken from the target entity, and may be a control group of the sample for reducing noise that may occur during estimating the average concentration of the microbes.

The environmental chamber 280A may change the environmental condition surrounding the sample, for example, from a first environmental condition to a second environmental condition that is different from the first environmental condition. For example, the first environmental condition may denote a case in which a temperature of the sample is 30° C., and the second environmental condition may denote a case in which the temperature of the sample is 60° C.

The reference chamber 280B accommodates the reference sample arranging portion 215 therein, and maintains the environmental condition of the reference sample constantly as the condition before being changed in the environmental chamber 280A. For example, the environmental condition of the reference sample may be maintained at the temperature of 30° C., that is, the first environmental condition.

The wave source 220 may irradiate waves to the sample in the sample arranging portion 210 and the reference sample in the reference sample arranging portion 215. Here, the multiple beam reflector 283 and the beam splitter 281 may be arranged between the wave source 220 and the sample arranging portion 210 and between the wave source 220 and the reference sample arranging portion 215. Also, a mirror 285 for changing a wave path provided from the wave source 220 may be further provided.

The multiple beam reflector 283 may split the wave incident from the wave source 220 to provide a plurality of wave paths. The multiple beam reflector 283 reflects the wave from a front surface and a rear surface thereof to provide a first wave L4 and a second wave L5 that are split in parallel with each other.

The beam splitter 281 is arranged on the plurality of wave paths provided by the multiple beam reflector 283, and may supply the first wave L4 and the second wave L5 respectively to the sample and the reference sample. After that, the beam splitter 281 may change the paths of the waves reflected and emitted from the sample and the reference sample, to provide the waves to the detector 230.

The detector 230 may detect a laser speckle and a reference laser speckle, which are caused by multiple scattering of the waves, respectively from the sample and the reference sample, at every time point set in advance. The detector 230 may include a first detector 231 corresponding to a path of the first wave reflected from the sample, and a second detector 233 corresponding to a path of the second wave reflected from the reference sample.

The controller 240 may obtain a temporal correlation of the detected laser speckle by using the detected laser speckle, and may estimate an average concentration of one or more kinds of microbes included in the sample based on the obtained temporal correlation. Here, the controller 240 may obtain reference information of the reference laser speckle by using the detected reference laser speckle. The controller 240 may use a difference in the average concentrations of the microbe according to the change in the environmental condition, and at this time, may exclude a time element from the difference between the average concentrations of the microbe by using the reference information of the reference laser speckle.

In other words, the entity discrimination apparatus 2-2 additionally includes the reference chamber 280B to obtain the variation in the average concentration of the microbe according to the change in the environmental condition. As such, noise according to the time may be removed, and there is no need to limit the measuring time, and thus, the entity identifying and analyzing may be simply performed.

Figure 25A:
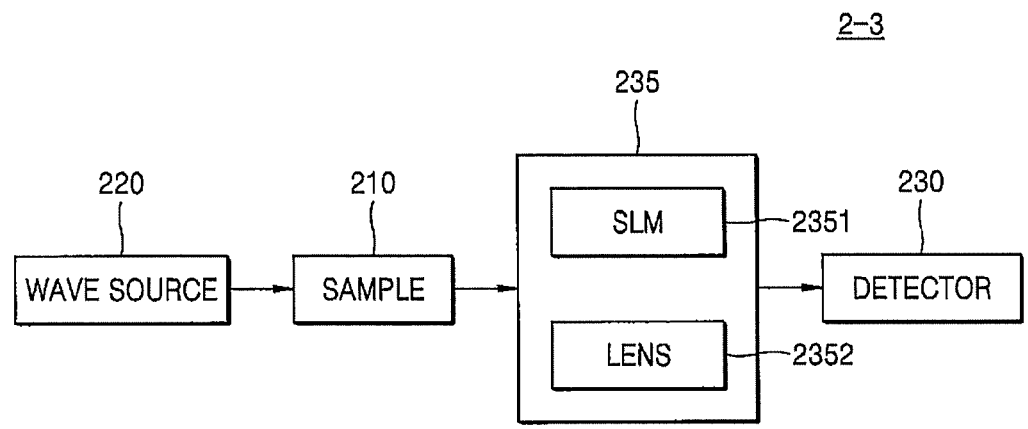
FIGS. 25A and 25B are conceptual diagrams showing schematically showing an entity discrimination apparatus according to another embodiment.
Figure 25B:
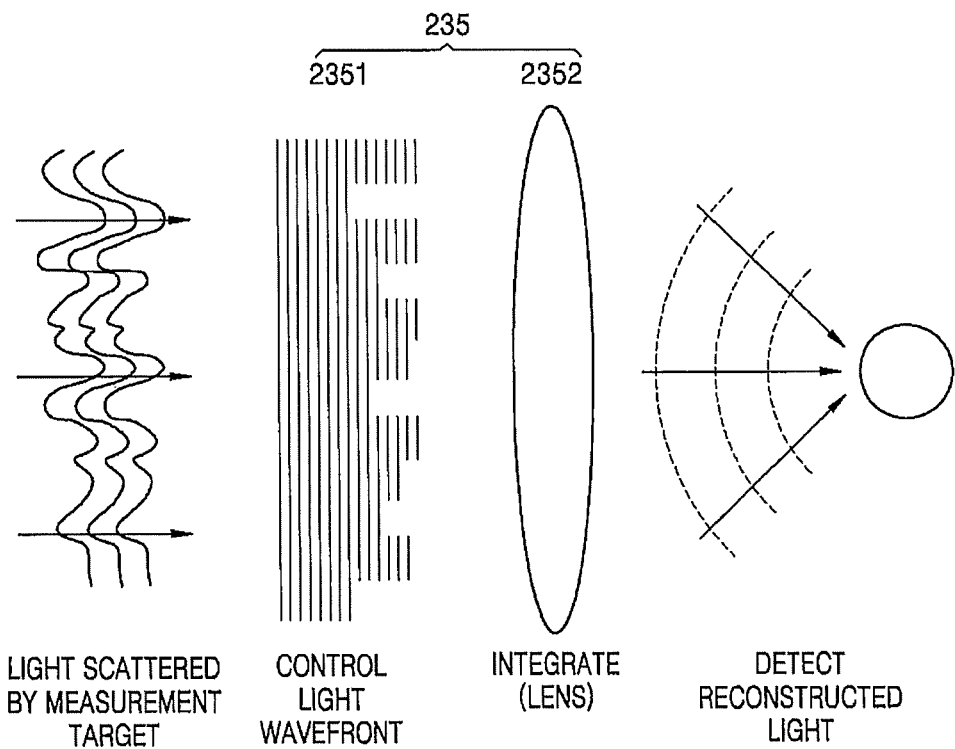

FIGS. 25A and 25B are conceptual diagrams showing schematically showing an entity discrimination apparatus 2-3 according to another embodiment.

Referring to FIGS. 25A and 25B, the entity discrimination apparatus 2-3 may further include an optical portion 235 that modulates to reconstruct a first wave signal scattered by the sample into a second optical signal before the wave of the wave source 220 is scattered by the sample. Here, the optical portion 235 may include a spatial light modulator (SLM) 2351 and the detector 230. When the waves scattered by a measurement target are incident to the optical portion 235, the optical portion 235 controls a wave front of the scattered wave to reconstruct the wave (light) before being scattered and provide the reconstructed wave to the detector 230.

The wave (light) scattered by the sample may be incident to the SLM 2351. The SLM 2351 may control the wave front of the wave scattered by the sample and provide the wave to the lens 2352. The lens 2352 may concentrate controlled light and provide the concentrated light to the detector 230. The detector 230 senses wave concentrated on the lens and reconstructs the wave output from the wave source before being scattered, and then, outputs reconstructed wave.

Here, the optical portion 235 may reconstruct the first optical signal scattered by the sample into the light before being scattered, in a case where there is no movement of a life in a stabilized medium, that is, the measurement target. However, in a case where a life exists in the measurement target, the first optical signal varies due to movement of the life, a phase control wave front may not be sensed, and accordingly, the first optical signal may not be modulated into a second optical signal having an optical phase conjugate wave front. The entity discrimination apparatus 2-3 including the optical portion 235 may minutely estimate the existence of the life or the concentration of the life by using the variation in the second optical signal.

Figure 26:
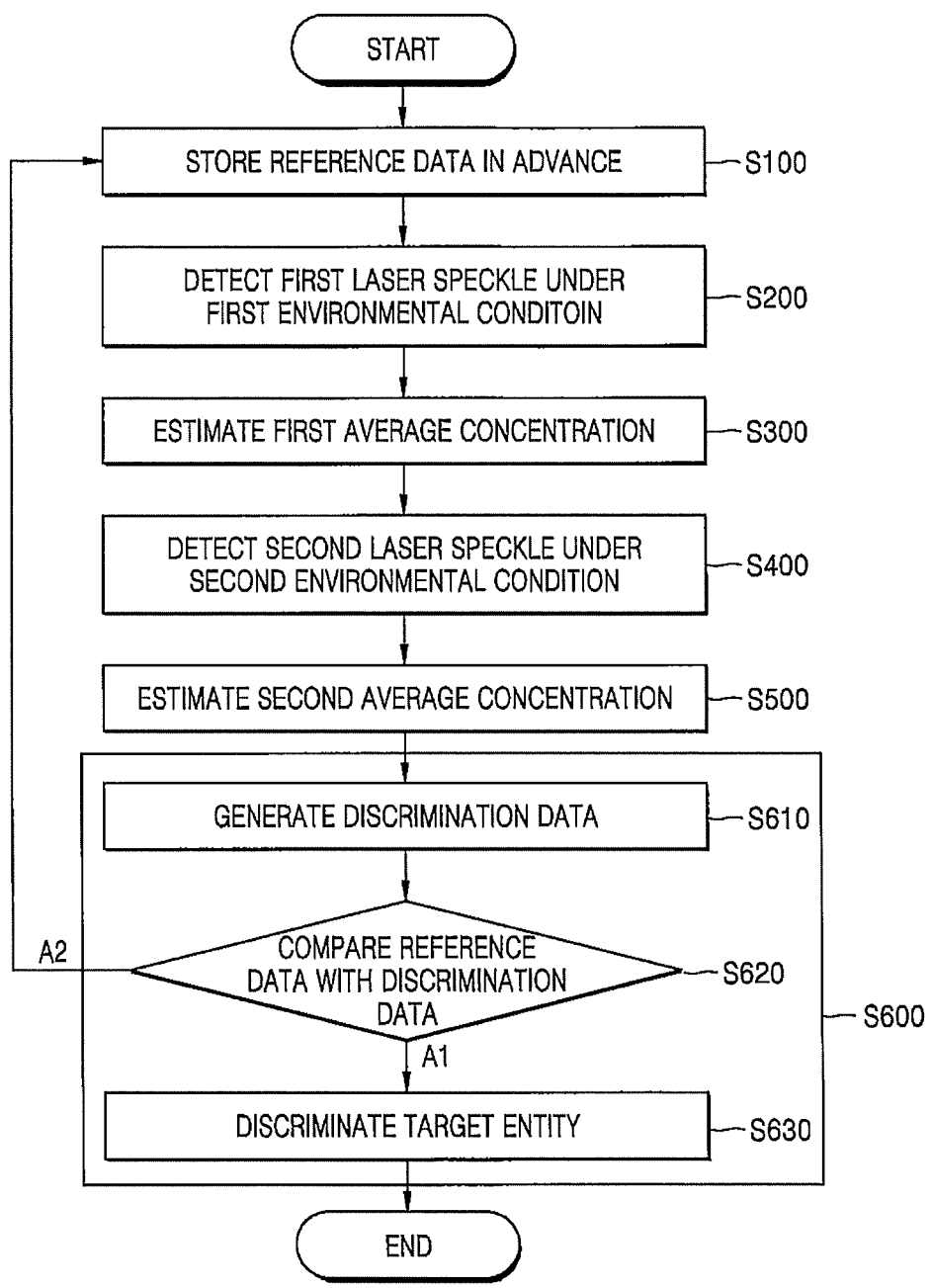
FIG. 26 is a flowchart illustrating an entity identifying method by using the entity discrimination apparatus according to an embodiment.

FIG. 26 is a flowchart illustrating an entity identifying method by using the entity discrimination apparatus according to an embodiment.

Referring to FIG. 26, reference data corresponding to each of a plurality of entities is stored in advance to establish a database (S100). The reference data may include a variation rate of the average concentration of the microbe according to the change in the environmental condition, with respect to each of the plurality of entities. The variation rate of the average concentration of the microbe may be individually stored according to a kind of the environmental condition. For example, reference data of an entity A may include plural pieces of data corresponding to a plurality of environmental conditions, for example, first reference data representing that 30% of microbes in average is reduced when the temperature is changed from 30° C. to 60° C., and second reference data representing that 45% of microbes in average is reduced when an antibiotic B is injected.

Next, the detector 130 may detect a first laser speckle that is generated when the wave irradiated to a sample taken from the target entity is multiple-scattered under a first environmental condition, at every time point set in advance (S200). After that, the controller 140 may estimate a first concentration of the microbes in the sample under the first environmental condition by using the detected first laser speckle (S300). The process of estimating the first concentration by the controller 140 may include obtaining a temporal correlation of the first laser speckle by using the detected first laser speckle, and estimating a first average concentration of one or more kinds of microbes included in the sample based on the obtained temporal correlation.

Next, the environmental chamber 180 may change the environmental condition of the sample from the first environmental condition to a second environmental condition. After changing the environmental condition to the second environmental condition, the detector 130 may detect a second laser speckle that is generated when the wave irradiated towards the sample in the second environmental condition is multiple-scattered, at every time point set in advance (S400). After that, the controller 140 may estimate a second concentration of the microbes in the sample under the second environmental condition by using the detected second laser speckle (S500). The process of estimating the second concentration by the controller 140 may include obtaining a temporal correlation of the second laser speckle by using the detected second laser speckle, and estimating a second concentration of one or more kinds of microbes included in the sample based on the obtained temporal correlation.

Next, the controller 140 may discriminate the target entity from among a plurality of entities by using a difference between the first concentration and the second concentration (S600). In detail, discrimination data may be generated by calculating a variation rate between the first average concentration of the microbe under the first environmental condition and the second average concentration of the microbe under the second environmental condition (S610). The discrimination data may act to exclude discrimination information of the target entity. The controller 140 may discriminate the target entity from among the plurality of entities by comparing the discrimination data with the reference data stored in advance (S620).

If there is reference data matching the discrimination data (A1), the controller 140 may determine the entity corresponding to the matching reference data to be equal to the target entity and discriminate the target entity (S630). However, if there is no matching reference data in the data storage 145 (A2), the data corrector 157 transforms the discrimination data of the target entity as one piece of reference data and stores the reference data in the data storage 145 to establish a database.

As described above, the entity discrimination apparatus according to the embodiments of the present disclosure may analyze information about exclusive microbes that each entity has rapidly with low costs by using the variation in the temporal correlation of the laser speckle caused by the microbes, and accordingly, the target entity may be rapidly and accurately discriminated from among a plurality of entities.

Hereinafter, a virus detecting apparatus 3 using the microbe detecting method according to the embodiments will be described below.

Figure 27:
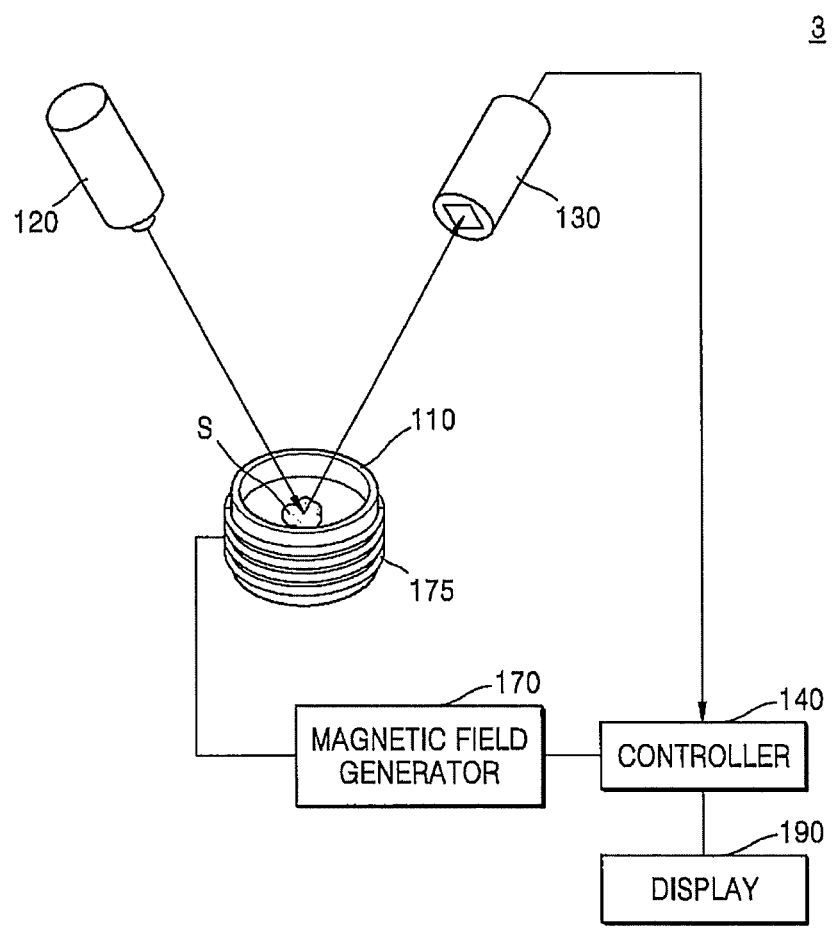
FIG. 27 is a schematic conceptual diagram of an apparatus for detecting virus according to an embodiment.
Figure 28:
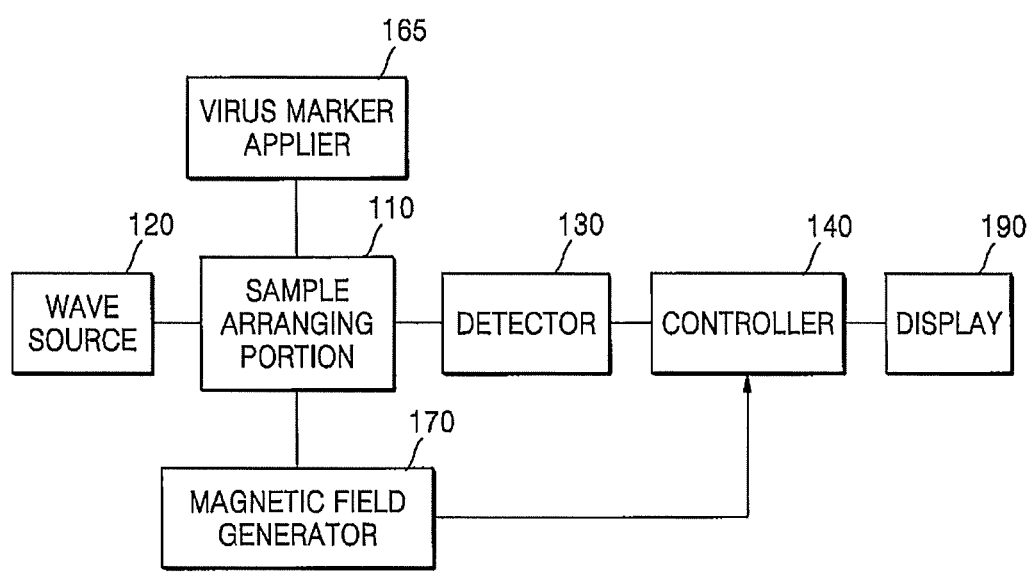
FIG. 28 is a block diagram schematically showing the apparatus for detecting virus of FIG. 27.
Figure 29A:
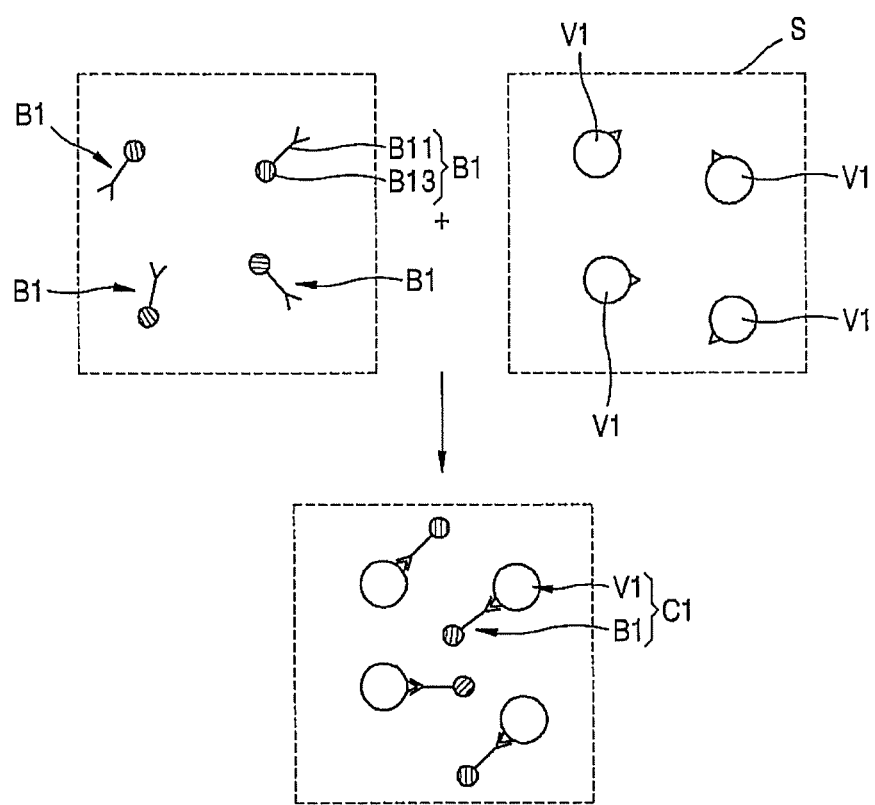
FIGS. 29A and 29B are schematic diagrams illustrating processes of applying a virus marker in a virus marker applier of FIG. 27.
Figure 29B:
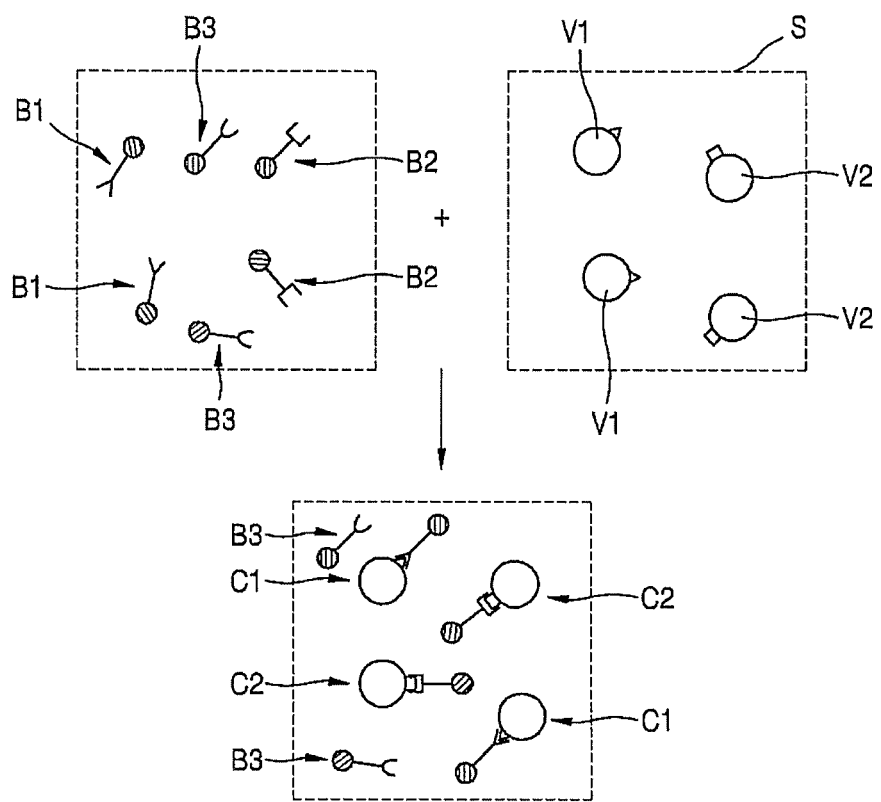

FIG. 27 is a conceptual diagram schematically showing the virus detecting apparatus 3 according to an embodiment, and FIG. 28 is a schematic block diagram of the virus detecting apparatus 3 of FIG. 27. FIGS. 29A and 29B are schematic diagrams illustrating processes of applying a virus marker in a virus marker applier 165 of FIG. 27.

Referring to FIGS. 27 and 28, the virus detecting apparatus 3 according to the embodiment may include the sample arranging portion 110, the virus marker applier 165, a magnetic field generator 170, the wave source 120, the detector 130, and the controller 140.

The sample arranging portion 110 may accommodate a sample S. Here, the sample S may include saliva, blood, or tissues of an entity, or stool, urine, or dead skin cells discharged out of the entity. Also, the sample S may be an organic sample such as food, or may be taken from a surface of a material by using a cotton swab, a tape, etc. The sample S may be entirely used, or may be prepared by using a unit to which viruses may be transferred, for example, a tape, a membrane, etc. The sample arranging portion 110 may have a container shape in which the sample S may be accommodated. The sample arranging portion 110 may support the sample S while restricting the movement of the sample S. In other words, the detection is performed in a state where the motion of the sample S is restricted.

The virus marker applier 165 applies a virus marker including magnetic particles to the sample S to form a detection complex, in which the virus marker is combined with the virus in the sample S. The virus marker applier 165 may be adjacent to the sample arranging portion 110. As another embodiment, the virus detecting apparatus 3 may perform a process of applying the virus marker to the sample after moving the sample arranging portion 110 to the virus marker applier 165. As another embodiment, the sample S may be moved to the virus marker applier 165 to apply the virus marker thereto, and then, may be arranged in the sample arranging portion 110. As described above, the location of the virus marker applier 165 is not restricted according to the present disclosure.

Referring to FIG. 29A, the virus marker B1 may be formed by combining a magnetic particle B13 with a material including a matching gene of a certain virus. In detail, the virus marker B1 may include an antibody B11 conjugated with a virus V1 in the sample S, and the magnetic particle B13 combined with the antibody B11. The antibody B11 of the virus marker B1 may be combined with the virus V1 in the sample S through an antigen-antibody reaction, and as such, the virus V1 may form a detection complex C1 that is combined with the magnetic particle B13 of the virus marker B1.

The magnetic particle may be a particle having a diameter of nano-meter level. Since the magnetic particle strongly scatters the wave irradiated from the wave source, it may be easy to detect the laser speckle. In addition, the magnetic particle may be, in more detail, a superparamagnetic nano-particle. Here, the superparamagnetic nano-particle may denote a material showing a strong magnetic property when a magnetic field is applied thereto from outside thereof. For example, the superparamagnetic nano-particle may include one or more selected from the group consisting of iron (Fe(III)), manganese (Mn), magnesium (Mg), zinc (Zn), and cobalt (Co). The superparamagnetic nano-particle according to the embodiment has an average particle diameter of 3 nm to 100 nm, for example, 4 nm to 30 nm. Also, the superparamagnetic nano-particle may have an average magnetizing force of 60 emu/g to 150 emu/g, for example, 80 emu/g to 130 emu/g.

Referring to FIG. 29B, the sample S may include a plurality kinds of viruses. In order to detect the plural kinds of viruses, the virus marker applier 165 may apply a plural kinds of virus markers, each including an antibody conjugated with one of the plural kinds of viruses and a magnetic particle combined with the antibody, to the sample S. In the drawing, an example in which two kinds of viruses are included in the sample S is shown for convenience of description. Since the viruses actually included in the sample S are not visible, a plural kinds of virus markers may be applied to the sample S to detect the viruses.

Here, the number of the kinds of the virus markers is not necessarily equal to the number of kinds of the viruses in the sample S. For example, as shown in FIG. 29B, the virus marker applier 165 may apply three kinds of virus markers, that is, a first virus marker B1, a second virus marker B2, and a third virus marker B3 to the sample S. When the sample S includes the first virus V1 matching to the first virus marker B1 and the second virus V2 matching to the second virus marker B2, a first detection complex C1 in which the first virus V1 and the first virus marker B1 are combined and a second detection complex C2 in which the second virus V2 and the second virus marker B2 are combined may be generated. The virus detecting apparatus 3 may detect kinds of the viruses, as well as the existence of the viruses in the sample S, via the first detection complex C1 and the second detection complex C2.

In addition, the virus marker applier 165 may remove a virus marker that may not be combined with a virus from the sample S. For example, the virus marker applier 165 may remove magnetic particles that have not been combined with the virus from the sample S, by using a porous filter. Here, the porous filter may filter the detection complex, in which the virus is combined with the virus marker, while transmitting the virus marker. In detail, as an embodiment, the virus marker applier 165 may remove the third virus marker B3 that may not match to any virus from the sample S, by using the porous filter (not shown). As such, the first detection complex C1 and the second detection complex C2 that are combined with the virus markers including the magnetic particles are only remained in the sample S, and then the viruses may be exactly detected.

Referring back to FIGS. 27 and 28, the magnetic field generator 170 is adjacent to the sample arranging portion 110 to form a magnetic field around the sample arranging portion 110 and move the detection complex. The magnetic field generator 170 may move the magnetic particles included in the detection complexes by using the magnetic force. Here, the viruses combined with the magnetic particles may be also moved. Since the virus does not move, unlike the microbe such as germs, laser speckles do not generate even when a wave is irradiated to the sample S, in which the virus marker is not applied, and thus, the virus may not be detected. Therefore, when the virus exists in the sample S, the detection complex in which the magnetic particles are combined with the virus may be generated by the virus marker applier 165, and a magnetic force is applied to the detection complex to make the virus move. Here, the magnetic field generator 170 may generate the magnetic field by using a radio frequency (RF) coil 175 surrounding the sample arranging portion 110, as shown in the drawings. However, the present disclosure is not limited thereto. The magnetic field may be generated around the sample S in the sample arranging portion 110 simply by using a permanent magnet. The magnetic field generator 170 may use a micro nuclear magnetic resonance (micro-NMR).

The magnetic field generator 170 may make the detection complex move by changing a direction or an intensity of the magnetic field at every predetermined first time period. When the magnetic field generator 170 applies the magnetic field having a constant direction and intensity to the sample S, the detection complex C1 moves in a direction and stops moving, and thus, it may be difficult to exactly detect the viruses. Therefore, the magnetic field generator 170 may change the direction or the intensity of the magnetic field at every predetermined first time period, to continuously make the detection complex move while the virus detecting apparatus 3 detects the virus.

The wave source 120 may irradiate the wave towards the sample S in the sample arranging portion 110. The wave source 120 may include all kinds of source devices capable of generating waves, for example, may be a laser irradiating light of a certain wavelength band. Although the present disclosure is not limited to the kind of wave source, for convenience of description, a case where the wave source is a laser will be described below.

For example, the laser having excellent coherence may be used as the wave source 120 in order to form speckles on the sample arranging portion 110. Here, when a spectral bandwidth of the wave source is shorter, a measuring accuracy may increase, wherein the spectral bandwidth determines the coherence of the laser wave source. That is, when a coherence length increases, the measuring accuracy also increases. Accordingly, a wave source irradiating the laser having a spectral bandwidth that is less than a reference bandwidth set in advance may only be used as the wave source 120, and when the spectral bandwidth is reduced to be less than the reference bandwidth, the measuring accuracy may increase.

The detector 130 may detect the laser speckle that is generated by the multiple scattering of the irradiated wave due to the movement of the detection complex C1 in the sample S at every predetermined time point. The detector 130 may include a sensing unit corresponding to the kind of the wave source 120, for example, a CCD camera that is an imaging device in a case where a light source of a visible ray wavelength band is used. The detector 130 may measure the surface of the sample S on which the laser speckle is generated, but the laser speckle may be detected from a region between the surface of the sample S and the detector 130. Also, the detector 130 may detect the laser speckle without using a lens portion having a predetermined focal length. The detector 130 may detect the laser speckle at a first time point at least, and may detect the laser speckle at a second time point, and then, may provide the controller 140 with the detected laser speckles. The first time point and the second time point are just examples selected for convenience of description, and the detector 130 may detect laser speckles at a plurality of time points more than the first and second time points.

In addition, an interval between the time points that are set in advance for the detector 130 to perform the detection may be less than the first time period through which the magnetic field generator 170 makes the detection complex move. That is, when duration of the movement of the detection complex is shorter than the interval between the detection time points, the fast movement of the detection complex may apply as noise. Therefore, the detector 130 may detect the laser speckle with a time interval that is less than the first time period for changing the direction or intensity of the magnetic field by the magnetic field generator 170, for performing the detection accurately.

In addition, in a case where the image sensor is used as the detector 130, the image sensor may be arranged so that a side d of one pixel in the image sensor is equal to or less than a grain size of the speckle pattern.

The controller 140 may obtain a temporal correlation of the detected laser speckle, by using the detected laser speckle. The controller 140 may estimate in real-time the existence of the virus or a concentration of the virus in the sample S, based on the obtained temporal correlation. Here, the controller 140 may receive magnetic field information about changed direction or intensity from the magnetic field generator 170, and may obtain the temporal correlation of the detected laser speckle by using the magnetic field information. In the present specification, real-time denotes estimating whether a virus exists or estimating variation in concentration of the virus within one hour, for example, the existence of the virus or the variation in the concentration of the virus may be estimated within five minutes. In more detail, the virus may be detected within 20 seconds. The method of obtaining the temporal correlation of the laser speckle in the controller 140 will be described later.

In addition, the virus detecting apparatus 3 may further include the display 190. The display 190 may display the existence of the virus, a concentration of the virus, or a kind of the virus estimated by the controller 140 to outside.

Figure 30:
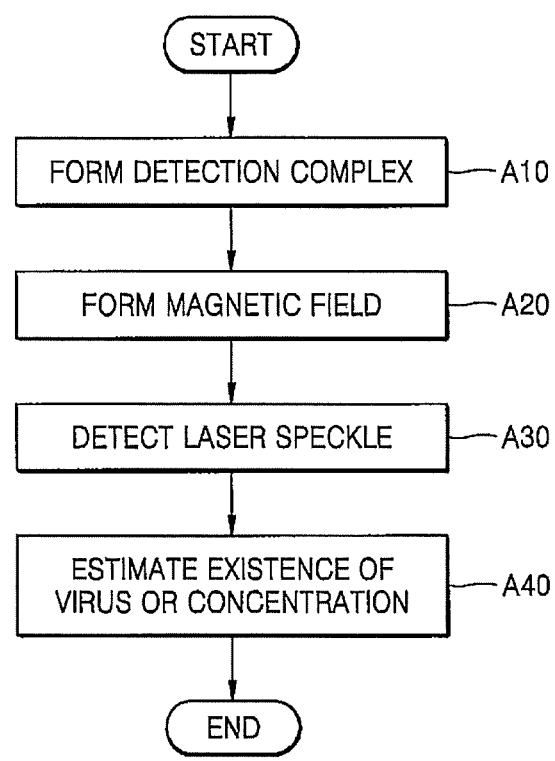
FIG. 30 is a flowchart illustrating a method of detecting virus, according to an embodiment.

FIG. 30 is a flowchart illustrating a method of detecting virus, according to an embodiment.

Referring to FIG. 30, a virus marker including magnetic particles is applied to the sample S to form a detection complex in which the virus marker and the virus in the sample S are combined (A10). Since there may be a plural kinds of viruses in the sample S, there may be a plural kinds of virus markers, and the number of the kinds of the viruses is not necessarily equal to the number of the kinds of the virus markers. Here, the virus markers may have different antibodies corresponding to the viruses, and the same magnetic particles combined with the antibodies. As such, when the magnetic field is formed around the sample S to make the detection complex move, the movement only varies depending on the kinds of the viruses, and thus, the viruses may be classifies.

After that, the magnetic field is formed around the sample S to make the detection complex move (A20). The magnetic field generator 170 may change the direction or intensity of the magnetic field at every first time period, and accordingly, continuous movement of the detection complex may be caused.

After that, the wave is irradiated towards the sample S, and the laser speckle generated when the irradiated wave is multiple scattered by the movement of the detection complex is detected at every time point set in advance (A30). Here, the interval between the time points set in advance may be less than the first time period for changing the direction or intensity of the magnetic field in the magnetic field generator 170.

After that, the controller 140 may obtain the temporal correlation of the detected laser speckle by using the detected laser speckle, and may estimate in real-time the existence of the virus or a concentration of the virus in the sample S based on the obtained temporal correlation (A40).

Figure 31:
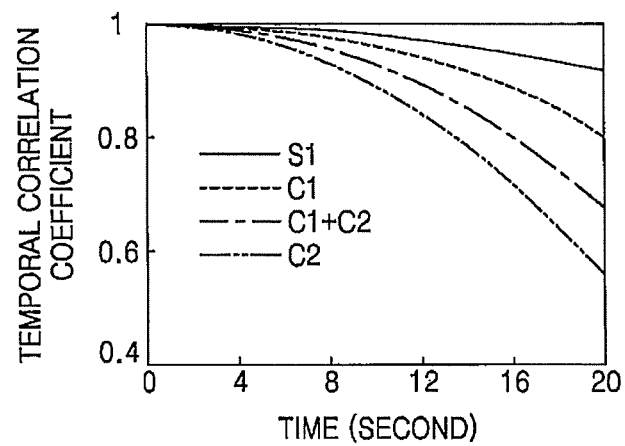
FIG. 31 is a graph showing a temporal correlation coefficient according to kinds of viruses in a sample.

FIG. 31 is a graph showing a temporal correlation coefficient according to kinds of viruses in a sample. In the graph of FIG. 31, a solid line S1 denotes a temporal correlation coefficient of a sample in which the virus does not exist, and a first dashed line C1 denotes a temporal correlation coefficient of a sample in which only a first virus V1 exists. A third dashed line C2 denotes a temporal correlation coefficient of a sample in which only a second virus V2 exists, and a second dashed line C1+C2 denotes a temporal correlation coefficient of a sample in which both the first virus V1 and the second virus V2 exist. Here, when the first virus V1 and the second virus V2 coexist, it may be assumed that the concentration thereof is equal to that of a case where the first virus only exists or a case where the second virus only exists. In FIG. 29B, the first virus V1 and the second virus V2 have the same shape, that is, a circular shape, but the first virus V1 and the second virus V2 may have different shapes and weights from each other. Therefore, even when the first detection complex C1 including the first virus V1 and the second detection complex C2 including the second virus V2 are placed in the same magnetic field, the first and second detection complexes C1 and C2 show different aspects of moving. Thus, the temporal correlations of the laser speckles may vary depending on the different movements. By using the above difference, the kinds of the viruses in the sample S may be discriminated.

As described above, the virus detecting apparatus according to the embodiments of the present disclosure may rapidly estimate the existence of the virus, the concentration of the virus, and the kind of the virus with low costs, by using the variation in the temporal correlation of the laser speckle caused by the detection complex including the virus and the magnetic particles.

Hereinafter, various types of installation spaces and operations of the sample property detecting apparatus 100 according to one or more embodiments will be described below with reference to FIGS. 32 to 37.

Figure 32:
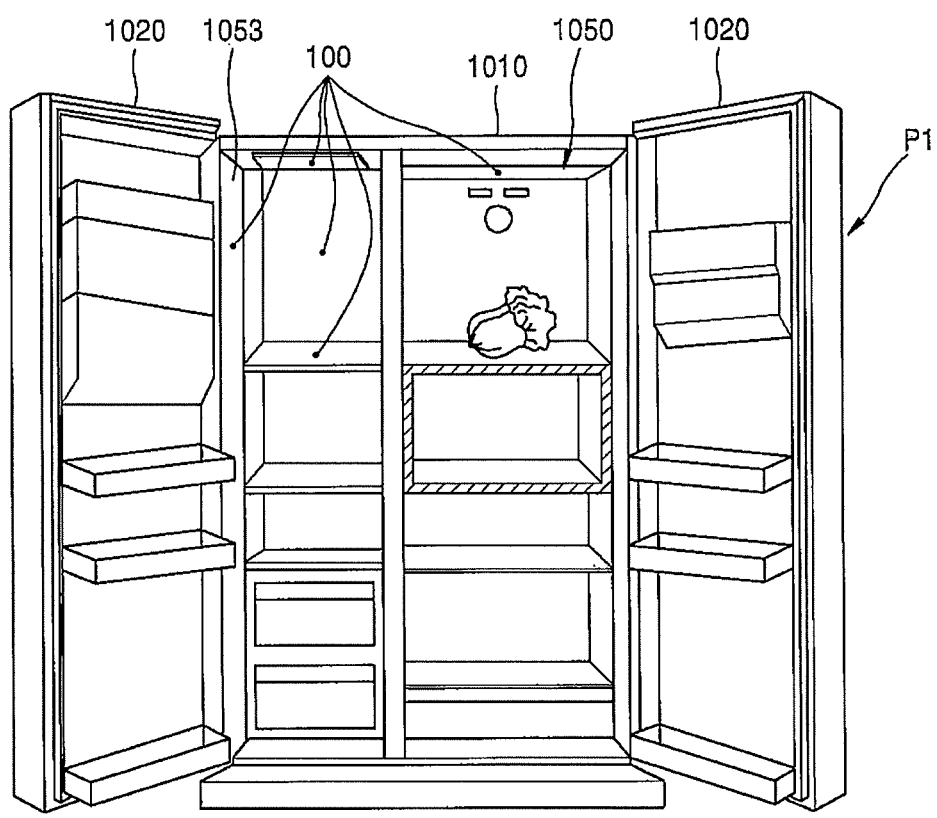
FIG. 32 is a diagram showing an example, in which the apparatus for detecting sample properties according to the embodiments is installed in a refrigerator.
Figure 33:
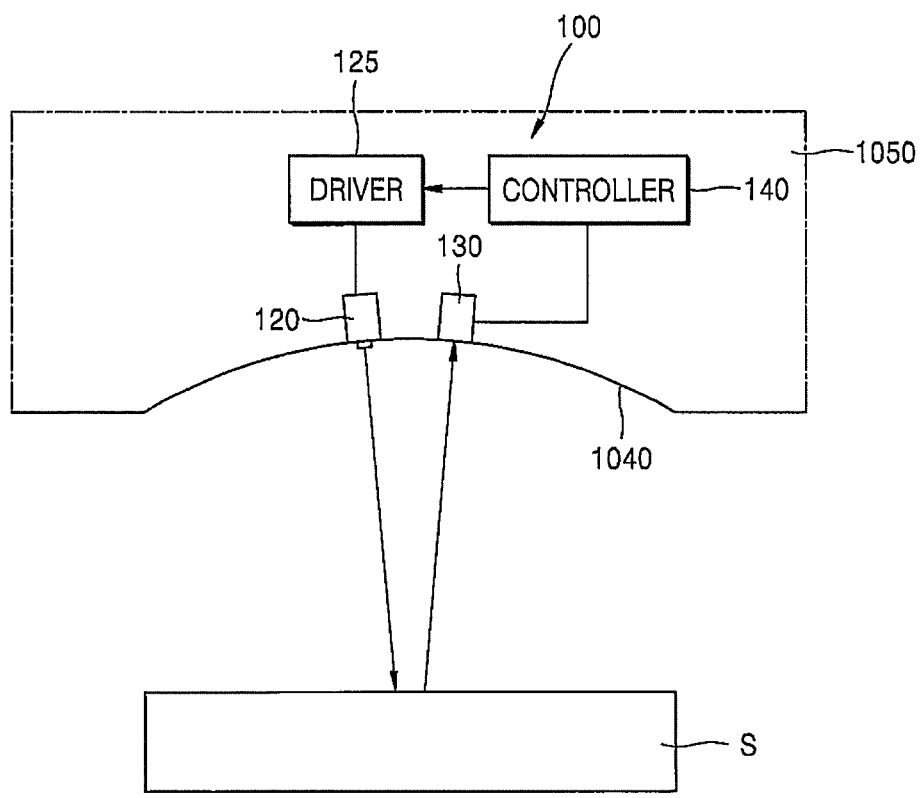
FIG. 33 is a schematic diagram showing an example, in which the apparatus for detecting sample properties of FIG. 32 is provided on a ceiling of a refrigerator.

FIG. 32 is a diagram showing an example, in which the sample property detecting apparatus 100 according to the embodiment is installed in a refrigerator P1, and FIG. 33 is a diagram schematically showing an example in which the sample property detecting apparatus 100 is provided on a ceiling portion 1050 of the refrigerator P1.

Referring to FIGS. 32 and 33, the refrigerator P1 may include a main body 1010 and a door 1020, and the sample property detecting apparatus 100 may be installed on various locations, e.g., a side surface 1053, a shelf 1051, the ceiling portion 1050, etc. of the refrigerator P1. In the present embodiment, the refrigerator P1 may include one or more recess portions 1040, and the sample property detecting apparatus 100 may be located in the recess portions 1040. The sample property detecting apparatus 100 may be located in the recess portion 1040 in order to ensure an appropriate distance for measuring chaotic waves in a case where food is full in the refrigerator P1.

The wave source 120 may be a laser light source. The wave source 120 may include a driver 125 for switching the direction of the laser. The driver 125 may change an irradiating direction of the wave source 120 for measuring germs on various portions of the refrigerator P1.

The detector 130 may be, for example, a camera including an image sensor, and may include an additional driver. Also, focusing may be adjusted so that one laser speckle may correspond to two or more pixels. As another embodiment, the detector 130 may be an image sensor.

Figure 34:
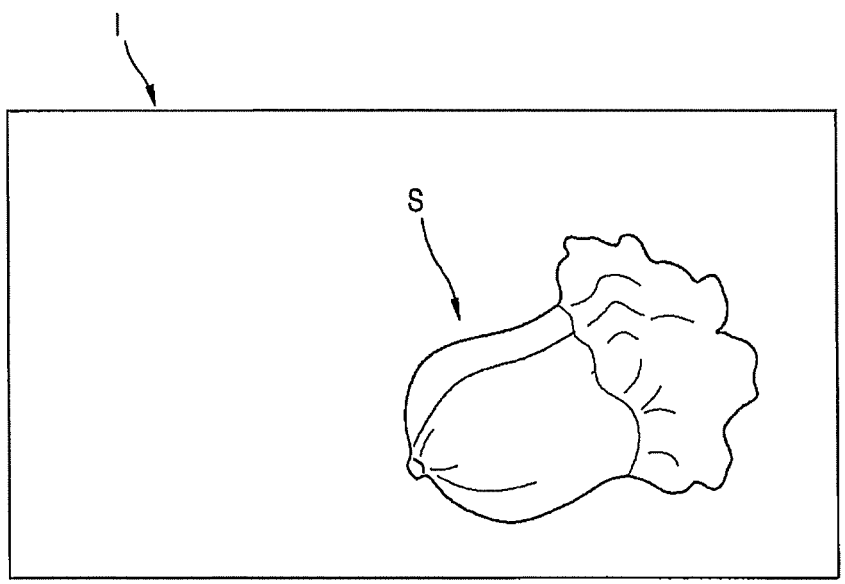
FIG. 34 shows an example of an image captured by the apparatus for detecting sample properties of FIG. 32.

FIG. 34 shows an example of an image captured by the sample property detecting apparatus 100 of FIG. 32.

Referring to FIG. 34, the detector 130 may capture images of the inside the refrigerator. In this case, a captured image of the refrigerator may include a region I where food S is stored and a region with no food, and the detector 103 may detect the region I where the food is stored and control the driver 125 to make the wave source 120 irradiates light to the region I. Also, in order to exactly capture an image of the speckle on the portion where the wave is irradiated from the wave source 120, the detector 130 may change an imaging location by using the driver and may adjust a focusing location.

Also, for appropriate controlling operation, the detector 130 may measure a distance by using the wave source 120, before the measurement. For example, the wave source 120 may include a modulated laser beam, for example, a signal having modulated amplitude or frequency of the laser beam, and may receive the modulated light via the detector 130 or an additional light receiver (not shown) and measure the distance.

The detector 130 may adjust the focus according to the measured distance.

Figure 35:
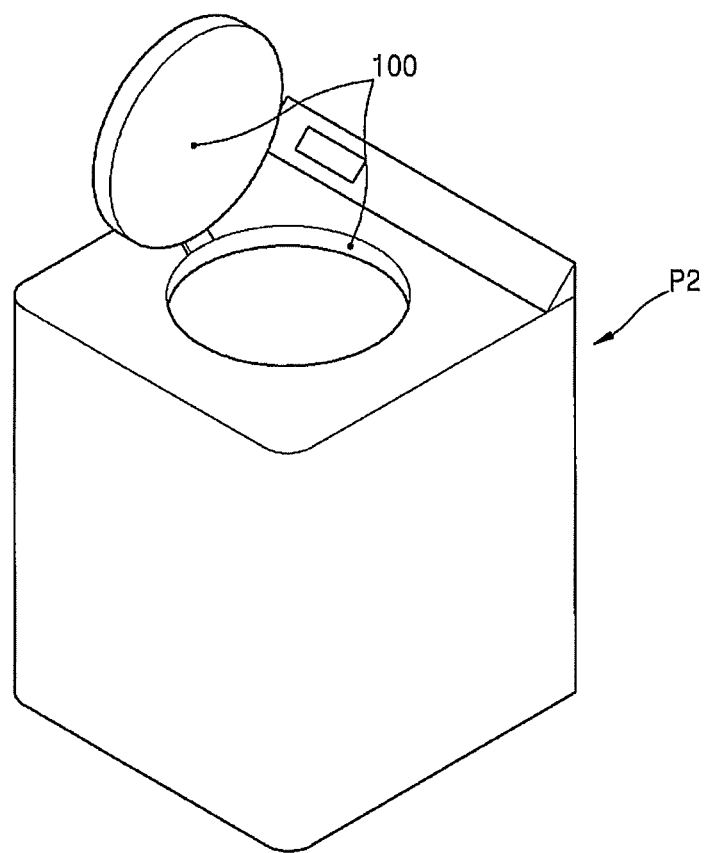
FIGS. 35 and 36 are diagrams showing examples, in which the apparatus for detecting sample properties according to the embodiments is provided on a lid of a washer or an outer circumference of a laundry feeding hole, or on a lid or a wall surface of a toothbrush sterilizer.
Figure 36:
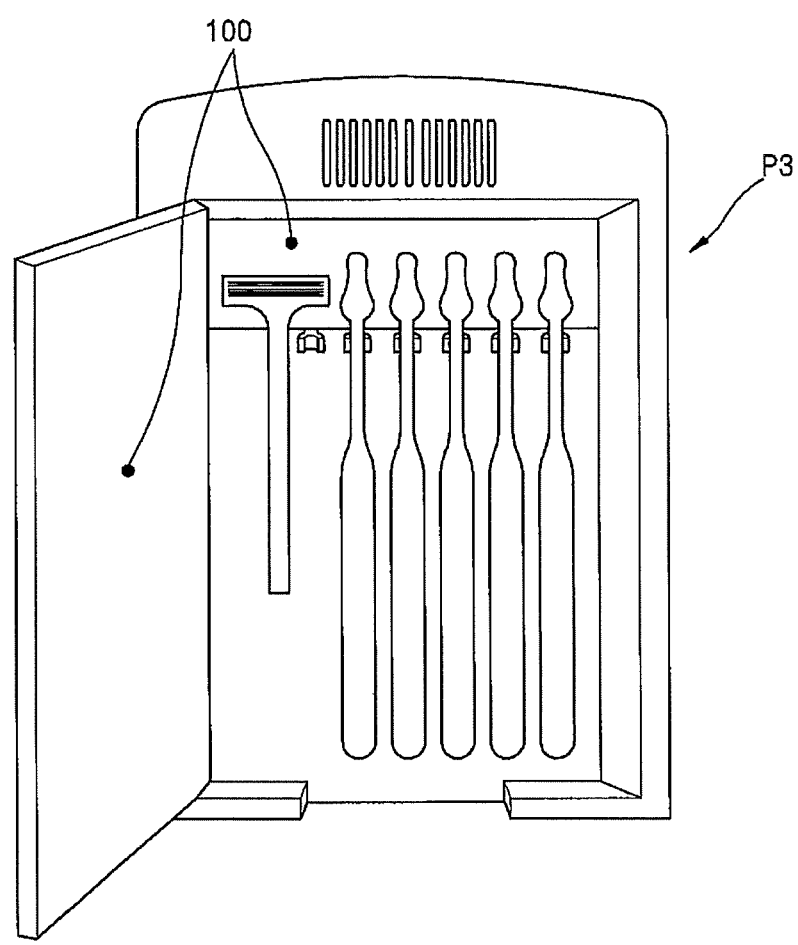

FIGS. 35 and 36 are diagrams showing examples, in which the sample property detecting apparatus according to the embodiments is provided on a lid of a washer or an outer circumference of a laundry feeding hole, or on a lid or a wall surface of a toothbrush sterilizer. The sample property detecting apparatus 100 provided on a lid of a washing machine P2 or an outer circumference of a laundry feeding hole has the structure described above with reference to FIGS. 32 and 33, and may operate.

Figure 37:
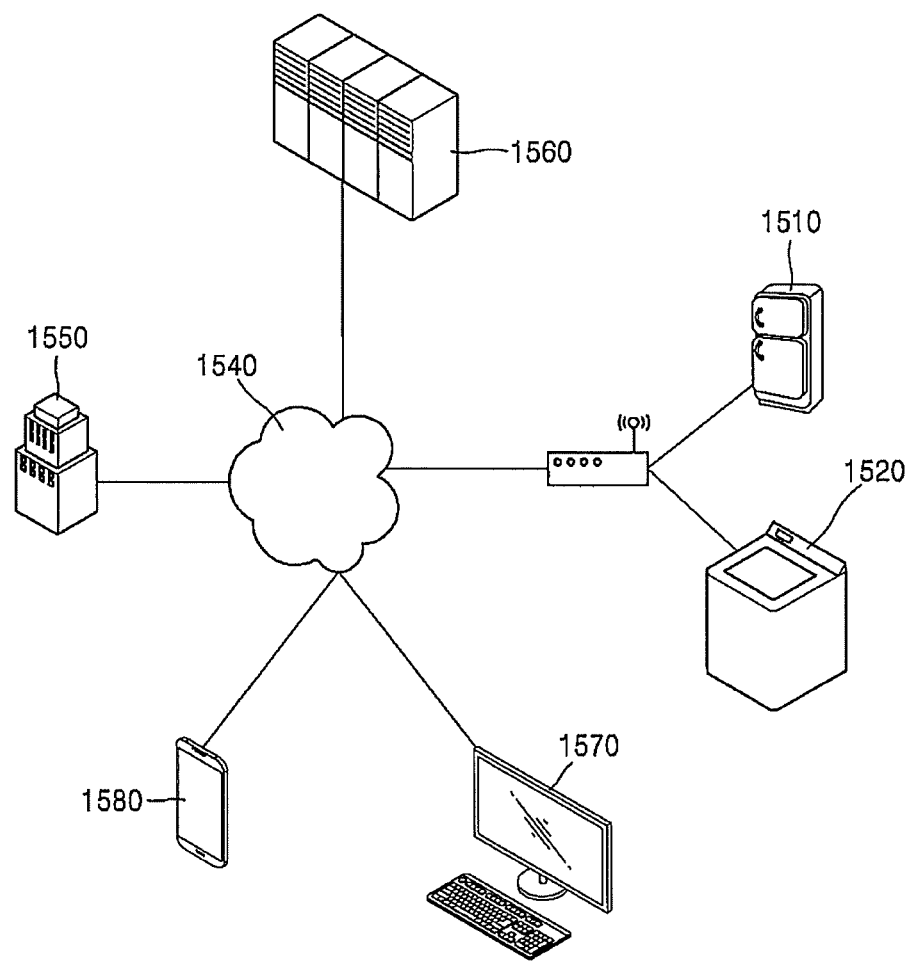
FIG. 37 is a diagram of a network for utilizing existence of microbes, concentration of the microbes, and kinds of the microbes measured by a sample property detecting apparatus according to the embodiments.

FIG. 37 is a diagram of a network for utilizing the existence of microbes, the concentration of the microbes, and the kinds of the microbes measured by the sample property detecting apparatus 100 according to the embodiments of the present disclosure.

Referring to FIG. 37, a home server 1530 collects data about the concentration, existence of the microbes, and the kinds of the microbes from apparatuses 1510 and 1520 each including the sample property detecting apparatus 100.

When the apparatuses 1510 and 1520 including the sample property detecting apparatus 100 may communicate directly through the Internet, an external server 1560 may perform functions of the home server 1530.

The home server 1530 or the external server 1560 measures a degree of risk based on the collected concentration, the existence of the microbes, and the kinds of the microbes, and when the home server 1530 or the external server 1560 determines the degree of risk is equal to or greater than a predetermined level, the home server 1530 or the external server 1560 sends a notification to a user terminal 1570 or 1580.

After receiving the notification, the user may click a link included in the notification to request an outside company 1550 to clean or to take prevention of epidemics in the corresponding apparatus 1510.

Otherwise, if a new kind of microbe is found, the user may request the outside company 1550 to analyze the microbe, and the home server 1530 or the external server 1560 may update the newly found microbe based on the analyzing result.

The user terminal 1570 or 1580 may include various types of terminals, e.g., a computer, a mobile phone, a tablet computer, etc. The user terminal 1570 or 1580 may identify the current concentration of the microbe by sending a request to the apparatuses including the sample property detecting apparatus 100. Also, the user terminal 1570 or 1580 may control the wave source 120 and the detector 130 of the sample property detecting apparatus 100 to measure an appropriate location. In particular, the user terminal 1570 or 1580 may receive the image captured by the detector 130 via the network, and may control the wave source 120 and the detector 130 based on the image.

As described above, the existence of the microbe is detected by measuring a temporal variation in the speckle pattern, and thus, the microbe may be rapidly detected within a few seconds without cultivating the microbes for a few days, and moreover, reactivity to an antibiotic may be precisely measured in a non-contact manner. For example, the cultivation process that takes one to four days may be omitted (that is, without the cultivation process), the existence of the microbe may be instantly detected only by irradiating the laser beam to a test target such as a petri dish and measuring a laser speckle. Accordingly, when it is detected that the microbe exists, reactivity with respect to the detected microbe may be measured instantly. Thus, the time may be enormously saved in fields dealing with the microbes, e.g., life science and medicine.

In addition, as described above, the optical system may be implemented only by using the laser light source and the image sensor, and thus, the optical system may be provided at low costs, and moreover, the optical system may be manufactured in a small size and may be applied widely to various fields. In addition, since the optical measurement is only used to detect microbes, there is no need to use target matters such as antigen-antibody, and there is no need to take the sample as in a gene amplification technique. Thus, costs incurred during the microbe measurement process may be reduced.

Hereinafter, the sample property detecting apparatus 100 according to another embodiment will be described below with reference to FIGS. 38 to 43.

Figure 38:
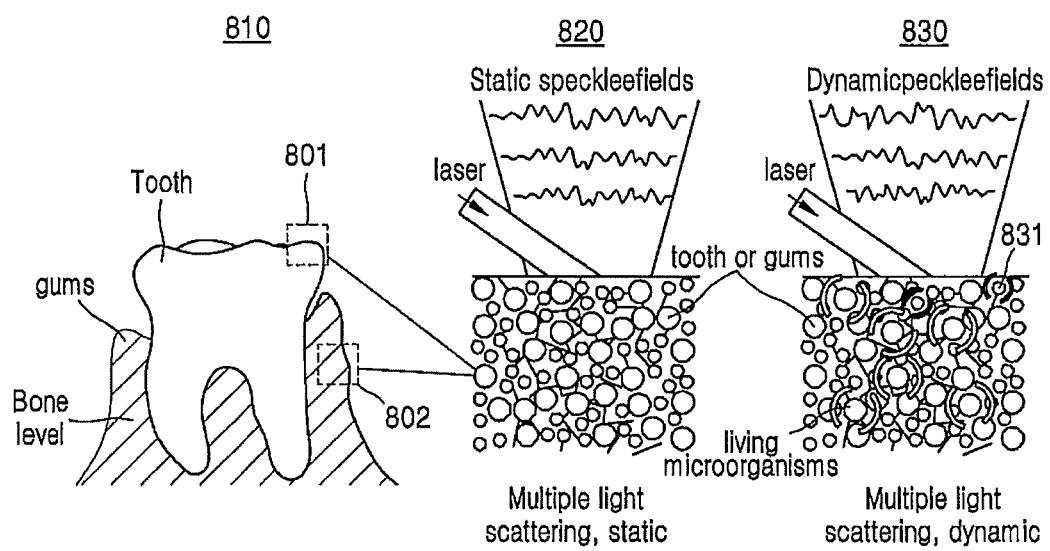
FIG. 38 is a diagram showing a shape of a laser speckle measured in relation to an oral cavity including gum and teeth, according to an embodiment.
Figure 39:
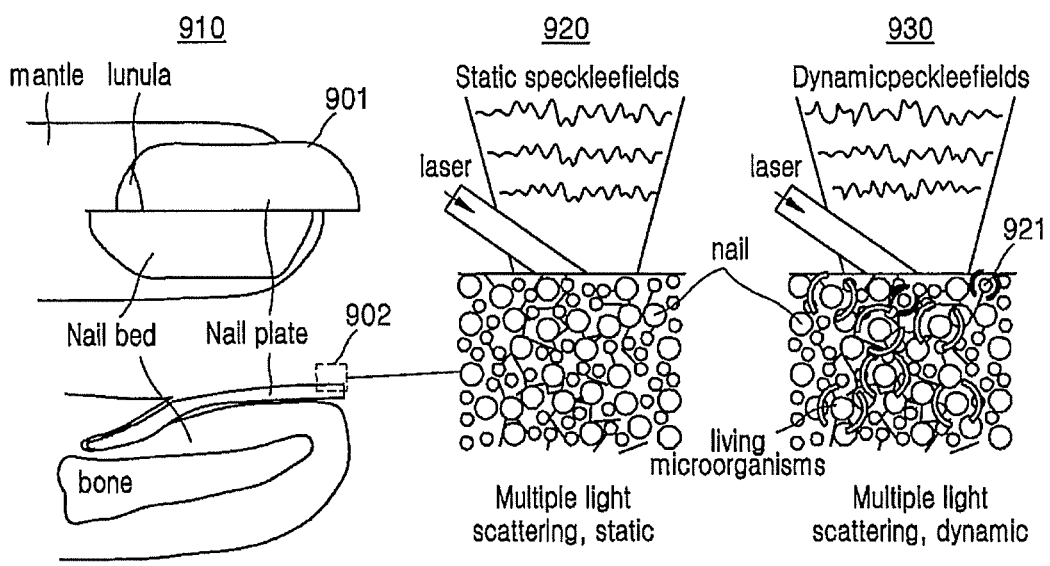
FIG. 39 is a diagram showing a shape of a laser speckle measured in relation to a nail and a toenail, according to an embodiment.

FIG. 38 is a diagram showing a shape of a laser speckle measured in relation to an oral cavity including gum and tooth, and FIG. 39 is a diagram showing a shape of a laser speckle measured in relation to a nail and a toenail.

Referring to FIGS. 38 and 39, light may be irradiated into or to a surface of an oral cavity 810 including tooth and gum that becomes a measurement target or a nail/toenail 901 and 902 by using a light source (e.g., laser beam) having high coherency. Here, the light irradiated from the light source 120 may be multiple scattered by materials included in a tooth 801, a gum 802, the nail 901, the toenail 902, etc. That is, multiple scattering of the light may occur. As described above, when the light is multiple scattered, the light may not form a long optical path. In addition, in a case where germs and microbes exist in or on the oral cavity 810 including the tooth 801 and the gum 802, the nail 901, or the toenail 902, the light may pass through the microbes a plurality of times.

As described above, spatial intensity distribution of the multiple-scattered light has very complicated shape, which may be referred to as a laser speckle pattern. That is, referring to FIGS. 38 and 39, the laser speckle may occur because a degree of generating constructive interference or destructive interference of the light on each point varies depending on each point of a measurement surface due to the complicated multiple scattering. Here, when the materials generating the scattering, that is, the tooth 801, the gum 802, the nail 901, the toenail 902, etc. do not move, the shape of the speckle may not change. That is, since the scattering is a phenomenon determined according to a wave equation, the shape of the laser speckle may not change provided that surfaces of the tooth, the gum, the nail, the toenail, etc. do not move.

Here, in a case where microbes exist on a surface of a certain body part (tooth, gum, nail, toenail, etc.), the optical path may minutely change according to time due to fine life activities (e.g., movement in cells, movement of microbes, etc.) of the microbes. Since the speckle pattern is generated due to interference of the light, a fine change in the optical path may cause variation in the laser speckle pattern. Accordingly, by measuring the temporal variation in the laser speckle pattern, the life activities of the microbes, that is, existence of the microbes in or on a certain body part, may be rapidly detected. That is, as described above, when the temporal variation in a plurality of laser speckle patterns measured at the reference time points through the multiple scattering is measured, it may be instantly measured whether the microbe exists or not.

Figure 40:
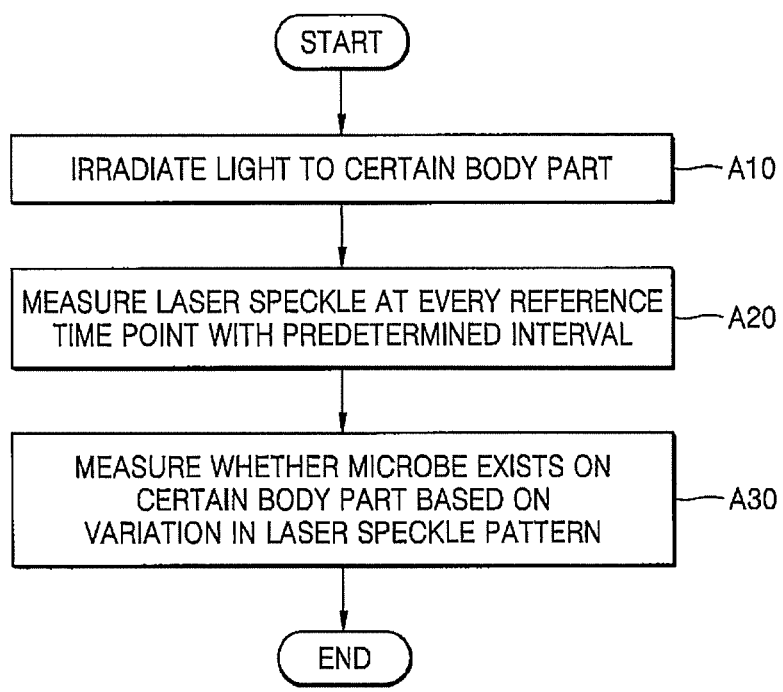
FIG. 40 is a flowchart illustrating a method of measuring whether a microbe exists in or on a surface of a certain body part, according to an embodiment.

FIG. 40 is a flowchart illustrating a method of measuring whether the microbe exists in or on a surface of a certain body part, according to an embodiment.

Each operation (1001 to 1003) shown in FIG. 40 may be performed by each element (e.g., the light source and the measuring portion) of the sample property detecting apparatus 100 according to the embodiment. In addition, when the certain body part is a nail and a toenail, the wave source 120, the detector 130, and the sample, e.g., the nail or the toenail, may be arranged in the structure shown in FIGS. 4A to 4C, and when the certain body part is an oral cavity, the wave source 120, the detector 130, and the sample, e.g., the oral cavity, may be arranged in the structure shown in FIGS. 4A and 4C.

In operation 1001, the wave source 120 may irradiate light towards inside or a surface of a certain body part such as the oral cavity, the nail, the toenail, etc. The light may be irradiated in the manner that the laser from the wave source 120 is reflected by the sample, that is, the certain body part (nail, toenail, oral cavity, etc.) or the laser from the wave source 120 transmits through the sample, that is, the certain body part (nail and toenail).

In operation 1002, the detector 130 may measure the laser speckle caused from the certain body part at every time point with a predetermined time interval. For example, since the light is irradiated to the certain body part at every reference time point with a predetermined interval, the laser speckle may be formed in or on the certain body part. In addition, inside or the surface of the certain body part where the multiple scattering occurs are photographed by a camera, etc., and thus, a laser speckle image on which the laser speckle is formed may be generated. Here, in order to measure the speckle pattern of a plurality of images, the camera including a two-dimensional image sensor or a one-dimensional optical sensor may be used as the detector 130. For example, the camera including an imaging device such as a charge coupled device (CCD) may be used as the detector 130.

Here, as shown in FIGS. 4A to 4C, locations the light incident to the certain body part and the sensor such as the camera, etc. may be freely arranged. For example, the locations of the incident light and the sensor such as the camera, etc. may be arranged in any type of arrangement, provided that a predefined condition between a size of a pixel of the camera and a speckle grain size is satisfied. Here, the distance from the laser light source to the camera may be restricted by a coherence length of the laser light source. For example, the coherence length may denote a distance within which the light may cause interference. When the light source having a long coherence length is used, the optical system in which the laser and the camera are spaced away from each other (that is, the distance between the laser light source and the camera) may be implemented.

In operation 1003, the detector 130 may measure whether the microbe exists in or on the surface of the certain body part, based on the variation in the laser speckle pattern representing the variation degree of the plurality of laser speckles according to time. That is, whether the microbe exists in the certain body part or on the surface of the certain body part may be measured based on dynamic change among the plurality of laser speckle patterns.

In order to compare dynamic change in the laser speckle pattern, at least two images measured at different time points from each other may be necessary. For example, in operation 1002, two or more laser speckle images may be generated at the reference time points with a predetermined interval, that is, a first laser speckle image generated by irradiating a laser beam and photographing the certain body part at a first time point and a second laser speckle image generated by irradiating light and capturing an image of the certain body part when a reference time (1 sec., 10 etc., etc.) has passed after the first time point, that is, at a second time point, may be generated. In addition, a third laser speckle image may be generated ten seconds later, and a fourth laser speckle image may be generated again ten seconds later. That is, the light may be irradiated with predetermined intervals (e.g., every ten seconds) after initially irradiating light, and then, n laser speckle images may be generated after n-1 seconds. Then, the difference among the generated laser speckle images may be analyzed to measure whether the microbe exists in the certain body part or on the surface of the certain body part.

Here, the method of measuring microbes may vary according to whether the existence of microbes is measured by using two speckle images or three or more speckle images. Here, detailed operations of measuring whether the microbe exists in or on the certain body part by using two or more laser speckle images will be described below with reference to FIGS. 41 and 42.

Figure 41:
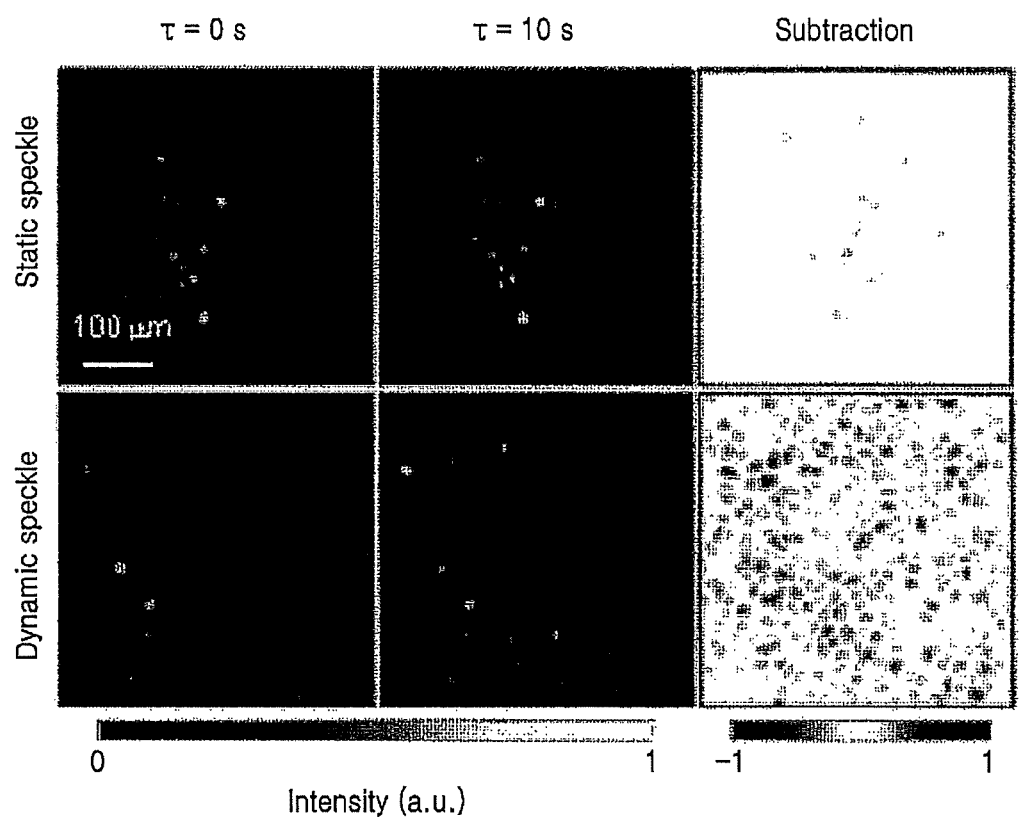
FIG. 41 is a diagram illustrating a method of measuring whether the microbe exists on the certain body part by using two laser speckle images.

FIG. 41 is a diagram illustrating a method of measuring whether the microbe exists on the certain body part by using two laser speckle images.

Referring to FIG. 41, when two laser speckle images generated by irradiating light with a predetermined time interval are used, a difference between the speckle image at 0 sec. and the speckle image at 10 sec. may be very small, that is, equal to or less than a first reference value defined in advance, if there is no microbe in or on the certain body part (static speckle). Although there may be a small difference, this may be interpreted as influence of noise existing during the experiment, e.g., moisture evaporation, vibration, etc. Here, when a microbe (e.g., B. cereus bacteria, etc.) exists in or on the certain body part (dynamic speckle), the difference between the speckle image generated at 0 sec. and the speckle image generated at 10 sec. may be equal to or greater than a second reference value that is defined in advance. That is, when there is a large difference in the laser speckle pattern, that is, equal to or greater than the second reference value between the speckle patterns measured at 0 sec. and 10 sec., it may be determined that the microbes such as bacteria exist in or on the certain body part.

As described above, the detector 130 checks whether the difference between two speckle images (e.g., difference between pixel values) is equal to or less than the first reference value and is equal to or greater than the second reference value, and determines whether the microbe exists in or on the certain body part. Here, the first reference value and the second reference value may be defined as equivalent values, or different values from each other.

Figure 42:
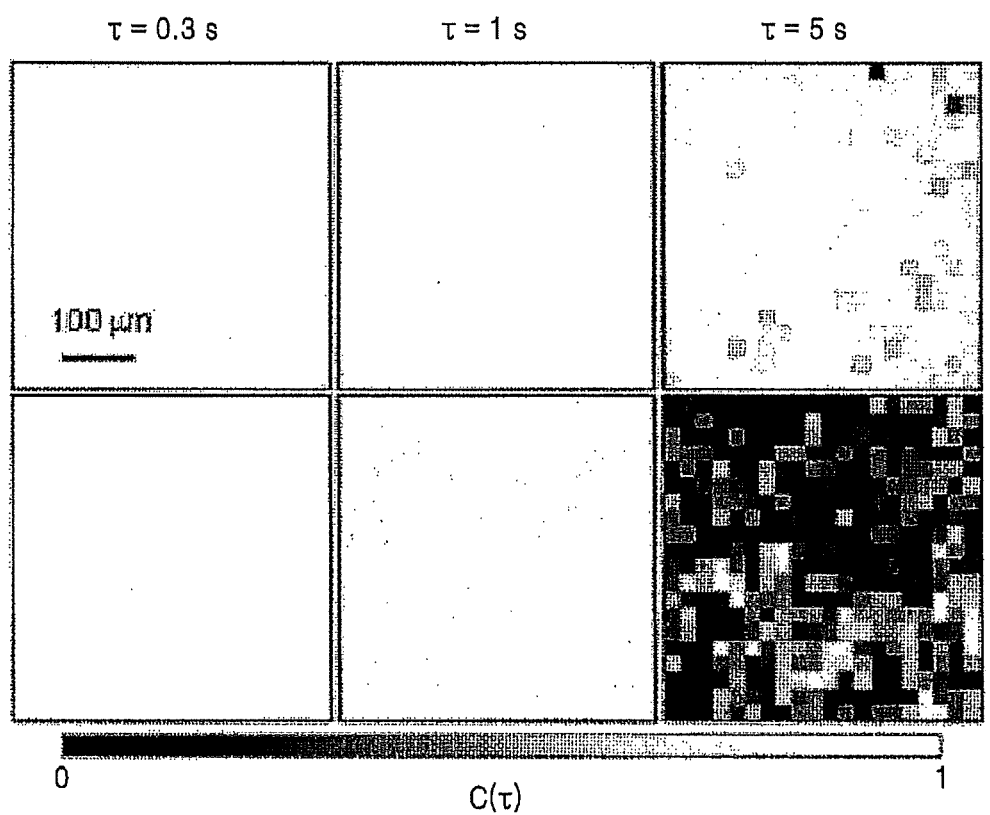
FIG. 42 is a diagram illustrating a method of measuring whether the microbe exists on the certain body part by using three or more laser speckle images.

FIG. 42 is a diagram illustrating a method of measuring whether the microbe exists on the certain body part by using three or more laser speckle images.

Referring to FIG. 42, when three or more speckle images generated with a predetermined time interval are used, the detector 130 may perform a time correlation analysis among the three or more speckle images to measure whether the microbe exists on the certain body part. That is, the detector 130 may measure whether the microbe exists on the certain body part based on the temporal correlation among the laser speckles that are generated when the light is irradiated into or onto the certain body part and multiple-scattered at different time points with a predetermined interval. For example, assuming that data standardizing the speckle image measured at each time point t is I(x,y;t), the detector 130 may calculate the temporal correlation coefficient at each time point by using Equation 3 above, with respect to a certain time delay τ. In addition, the detector 130 may measure whether the microbe exists in or on the certain body part based on a variation degree in the calculated temporal correlation coefficient, and FIG. 42 shows a result of measurement. Here, calculation of the temporal correlation coefficient based on Equation 3 above and measuring whether the microbe exists on the certain body part based on the calculated temporal correlation coefficient have been already described above with reference to Equation 3, and thus, detailed descriptions thereof are omitted.

As described above, the existence of the microbe is measured by measuring a temporal variation in the speckle pattern, and thus, the microbe may be rapidly detected within a few seconds without cultivating the microbes for a few days. For example, the cultivation process that takes one to four days may be omitted (that is, without the cultivation process), the existence of the microbe may be instantly detected only by irradiating the laser beam to the sample and measuring a laser speckle. Accordingly, when the sample (nail, toenail, oral cavity, food, etc.) is prepared, the existence and activity of the microbes and germs may be measured instantly, and thus, the existence of the microbes and germs may be measured rapidly and simply in dental clinics, dermatology clinics, households, grocery stores, etc.

Figure 43:
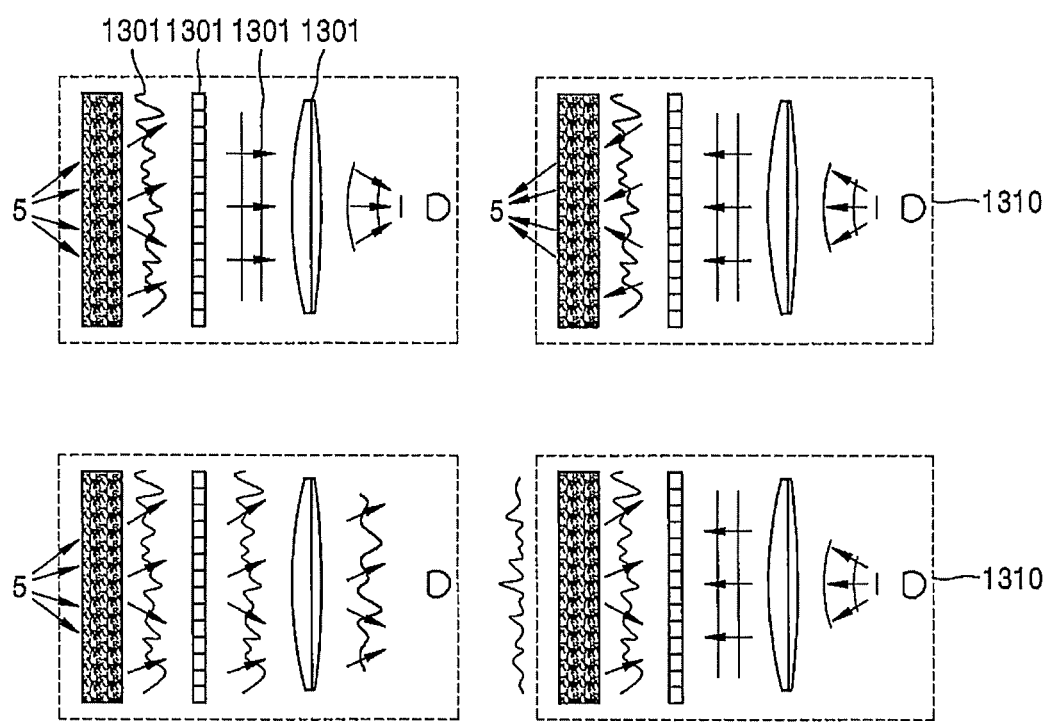
FIG. 43 is a diagram of an optical system configured by using a time-reversal mirror, according to an embodiment.

FIG. 43 is a diagram of an optical system configured by using a time-reversal mirror, according to an embodiment.

In FIG. 43, 1310 denotes a case in which an optical path is reversed in a scatter by using a time-reversal mirror, and 1320 denotes a case an optical path reversal does not occur due to a change in the optical path when a moving object exists in the scatter. That is, 1310 shows a case where a time-reversal reflection occurs, and 1320 shows a case where the time-reversal reflection does not occur.

The time-reversal mirror may denote a mirror causing an effect that the light reflected by a mirror surface and returning to an original point is reversed backward along an optical path towards the mirror surface as it is (that is, the time-reversal reflection effect). Although a general mirror does not generate the time-reversal reflection effect, the time-reversal reflection effect may occur under a certain condition.

Korean Registered Patent No. 10-1599147 discloses an apparatus for common-channel digital optical phase conjugation by using the time-reversal mirror, and when the optical system is configured by using the time-reversal mirror, existence of a moving object in a scatter (e.g., a sample such as a tooth, a gum, nails, toenails, food) may be sensitively measured. Since the time-reversal reflection occurring in a complex scatter is a physical phenomenon that has to be precisely controlled, the time-reversal reflection effect may not occur due to a small change in the scatter as shown in 1320 of FIG. 43. Accordingly, it may be measured whether an object such as a germ or a microbe exists in the scatter (e.g., sample) based on the time-reversal reflection effect that occurs in the scatter by using the time-reversal mirror.

Referring 1310 of FIG. 43, light of an arbitrary pattern may be incident from a front portion of a scatter. That is, the light having an arbitrary pattern may be incident to the scatter. Here, the pattern may be generated by a fixed aperture or a mask, or may be realized as a display pattern. Then, the light incident to the scatter may be scattered by the scatter. Then, an SLM 1302 may convert light 1301 scattered by the scatter into a plane wave 1303. The plane wave 1303 converted by the SLM 1302 is reflected by a surface of a mirror 1304, and may be emitted as the light of original state due to the time-reversal reflection that occurs automatically.

Here, as shown in 1320 of FIG. 43, when a moving object (a matter to be detected such as germs, microbes, etc.) exists in the scatter, the optical path may not go along with the time-reversal reflection any further. That is, light of different pattern from the light initially incident to the scatter may be generated. Then, a user or a measurement portion may measure movement in the scatter by observing or measuring the pattern of the light reflected and returned from the mirror 1304. That is, by comparing the pattern of returning light with the pattern of the light that is initially incident to the scatter, the existence of the moving object (e.g., microbes, germs, etc.) in the scatter may be detected based on the comparison result, that is, a difference between the patterns. Referring to 1320 of FIG. 43, since the pattern of the returning light is different from the pattern of the incident light, it may be detected that the moving object exists in the scatter.

In addition, as shown in 1310 of FIG. 43, when the pattern of the returning light is equal to or similar to, within a predetermined reference range, the arbitrary pattern of the light initially incident to the scatter, that is, when the pattern of the returning light corresponds to the time-reversal reflection effect, it may be detected that the moving object does not exist in the scatter. That is, it may be detected that microbes or germs do not exist in the scatter.

Figure 44:
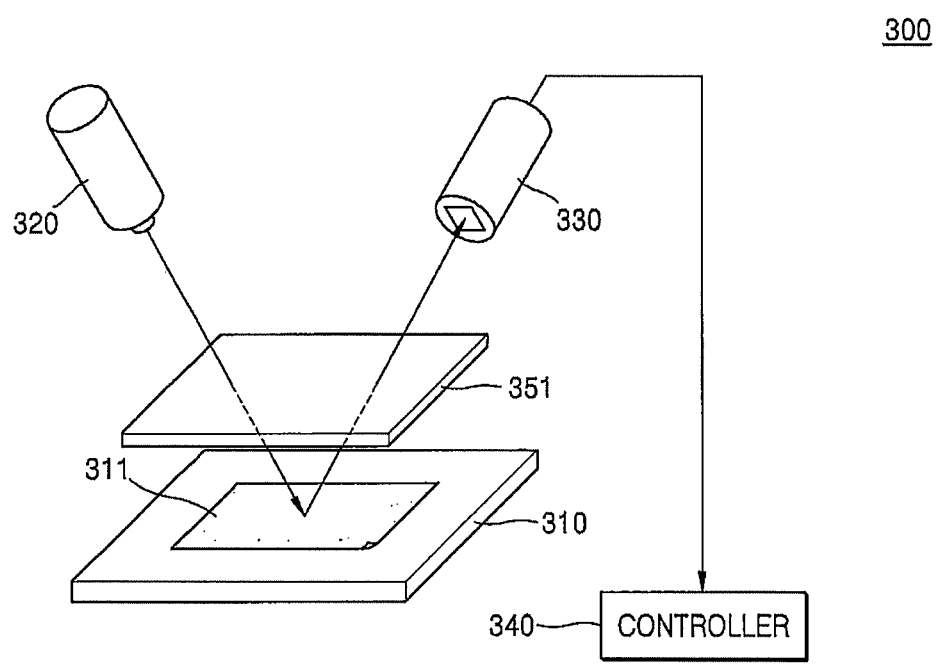
FIG. 44 is a conceptual diagram schematically showing an apparatus for detecting sample properties, according to another embodiment.
Figure 45:
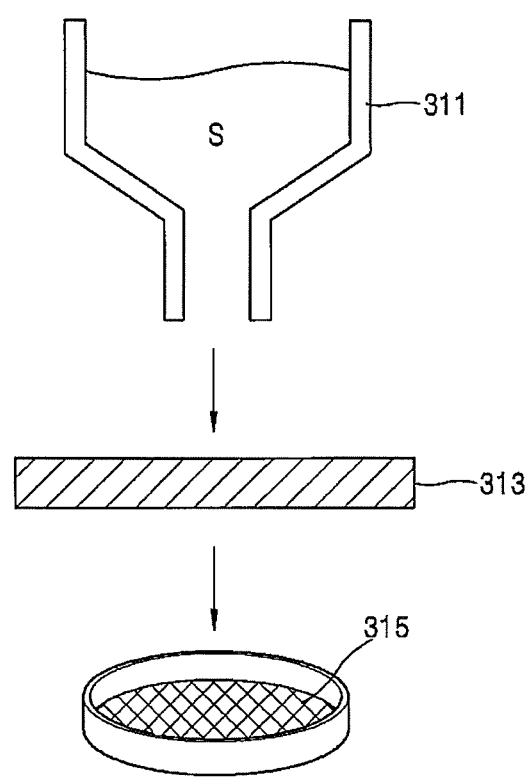
FIG. 45 is a conceptual diagram of another example of a sample collection unit of FIG. 44.
Figure 46:
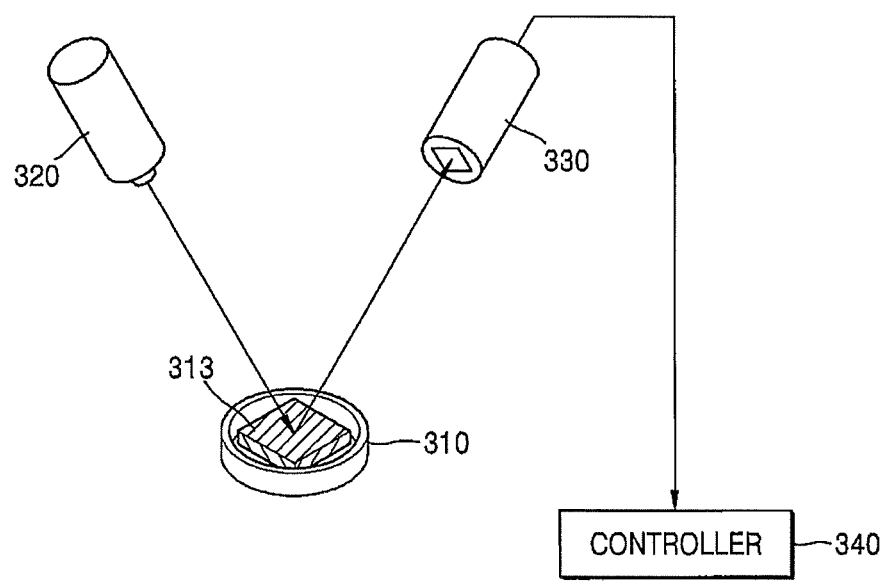
FIG. 46 is a conceptual diagram schematically showing a sample property detecting apparatus using the sample collection unit of FIG. 45.

FIG. 44 is a conceptual diagram schematically showing a sample property detecting apparatus 300 according to another embodiment, and FIG. 45 is a conceptual diagram of another example of a sample collection unit 311 of FIG. 44. Also, FIG. 46 is a conceptual diagram schematically showing the sample property detecting apparatus 300 using the sample collection unit 311 of FIG. 44.

Referring to FIG. 44, the sample property detecting apparatus 300 according to the embodiment may include a wave source 320, a detector 330, a controller 340, a sample arranging portion 310, and the sample collection unit 311. Structures of the wave source 320, the detector 330, and the controller 340 and the method of detecting microbes by using the elements according to the embodiment are the same as those of the previous embodiment, detailed descriptions thereof are omitted here.

The wave source 320 may irradiate the wave towards the sample S in the sample arranging portion 310. The wave source 320 may include all kinds of source devices capable of generating waves, for example, may be a laser irradiating light of a certain wavelength band.

The detector 330 may detect the laser speckle that is generated by the multiple scattering of the irradiated wave due to the sample S at every predetermined time point. Here, the time point may denote one instant during continuous flow of time, and time points may be set in advance with constant time intervals therebetween, but is not limited thereto, that is, may be set in advance with an arbitrary time interval. The detector 330 may include a sensing unit corresponding to the kind of the wave source 320, for example, a CCD camera that is an imaging device in a case where a light source of a visible ray wavelength band is used. The detector 330 may detect the laser speckle at a first time point at least, and may detect the laser speckle at a second time point, and then, may provide the controller 340 with the detected laser speckles.

The controller 340 obtains temporal correlation by using the detected laser speckles, and may estimate the existence of the microbes or concentration of the microbes in the sample S based on the temporal correlation.

The sample collection unit 311 may collect the sample S including microbes from an object. As an embodiment, the sample collection unit 311 of FIG. 44 may include an adhesive member of a plane shape. The sample collection unit 311 of FIG. 44 may be attached to and detached from skin of a human being via the adhesive member, and then, may be accommodated in the sample arranging portion 310. Many microbes exist on the skin of a human being, parasites such as *Demodex folliculorum* may exist. Since invisible microbes or parasites such as *Demodex folliculorum* are collected by the sample collection unit 311 and analyzed by using the sample property detecting apparatus 300, the existence of the microbes or parasites in the skin of a human being, that is, the object, may be identified. As another embodiment, the sample collection unit 311 may be attached to and detached from materials actively contacting human beings, and then, existence of the microbes in the materials may be identified. For example, such an object as a carpet may not be suitable to be used as a sample directly, because of a large volume and movement of carpet fibers. Then, the sample collection unit 311 is attached to and detached from the object and analyzed by using the sample property detecting apparatus 300, and thus, existence of the microbes in the object may be identified.

Referring to FIGS. 45 and 46, as another embodiment, the sample collection unit 311 may collect liquid sample. Here, the sample S may be a liquid having fluidity, e.g., urine, blood, etc. Otherwise, the sample S may be include a sample having non-fluidity such as stool mixed with a solvent such as water. Here, the mixed solvent may not affect growth of microbes in the sample S. The sample S having the fluidity may be collected by the sample collection unit 311 and filtered by a filter 313. When the microbe is to be detected by directly using the sample S having fluidity, it may be difficult to exactly detect the microbe because it is difficult to discriminate the flow from the movement of the microbe. Therefore, the sample property detecting apparatus 300 according to the embodiment may filter the microbes from the sample S, by using the filter 313 that may filter microbes such as bacteria and transmits liquid, for example, a porous filter.

In a case where the sample S is urine, microbes in the urine may be filtered by the filter 313 and water 315 may mostly pass through the filter 313. Alternately, when the sample S is blood, red blood cells, white blood cells, or microbes having a size as that of bacteria are filtered by the filter 313, and blood plasma may pass through the filter 313. As described above, a wave is irradiated onto the filter 313 on which the microbes are filtered, and then, a laser speckle caused by the microbes is detected, thereby identifying the existence of the microbe in the sample S or the concentration of the microbe.

Figure 47:
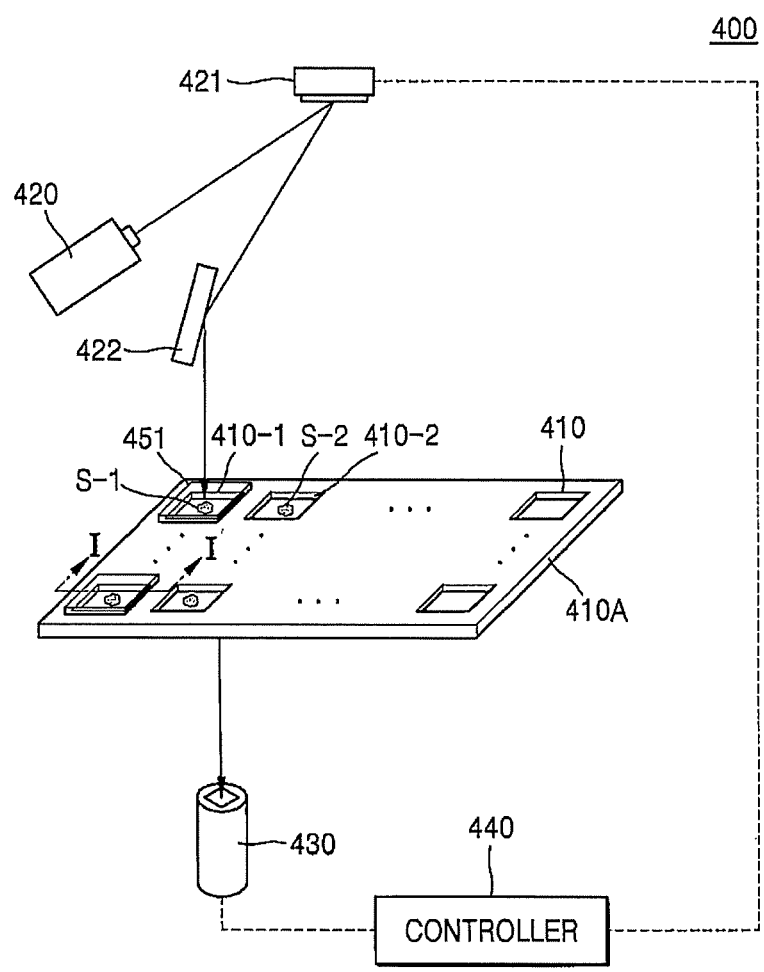
FIG. 47 is a conceptual diagram schematically showing a sample property detecting apparatus according to another embodiment.
Figure 48:
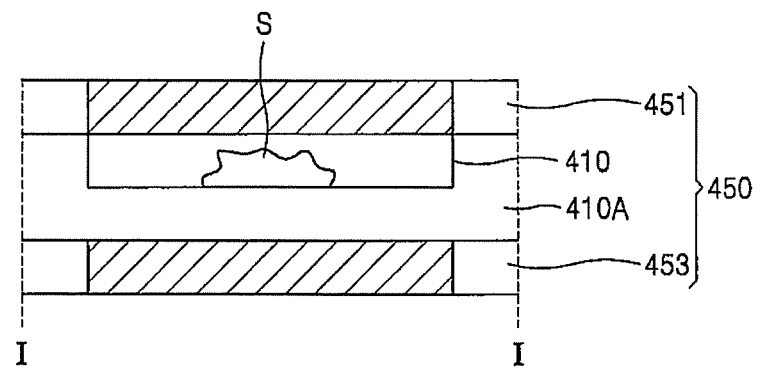
FIG. 48 is a cross-sectional view taken along a line I-I of FIG. 47.

FIG. 47 is a conceptual diagram schematically showing a sample property detecting apparatus 400 according to another embodiment, and FIG. 48 is a cross-sectional view taken along a line I-I of FIG. 47.

Referring to FIG. 47, the sample property detecting apparatus 400 according to the embodiment may include a wave source 420, a wave path changer 421, a detector 430, a controller 440, a sample arranging portion 410, a sample array portion 410A, and a multiple scattering amplifier 450. Structures of the wave source 420, the detector 430, and the controller 440 and the method of detecting microbes by using the elements according to the embodiment are the same as those of the previous embodiment, detailed descriptions thereof are omitted here.

The sample property detecting apparatus 400 according to the embodiment may include a plurality of sample arranging portions 410. The plurality of sample arranging portions 410 may be arranged with a predetermined spaced distance from one another, and as shown in the drawings, the plurality of sample arranging portions 410 may be arranged in one sample array portion 410A. Hereinafter, a case in which the plurality of sample arranging portions 410 are arranged in one sample array portion 410A will be described for convenience of description.

A plurality of samples may be accommodated in each of the plurality of sample arranging portions 410. The plurality of samples may be the same as one another, or may be different from one another. For example, a first sample S-1 may be accommodated in a first sample arranging portion 410-1, and a second sample S-2 may be accommodated in a second sample arranging portion 410-2. The first sample S-1 and the second sample S-2 may be taken from different objects from each other, or may be taken from different regions in one object.

The wave source 420 may irradiate the wave towards the sample S in the sample arranging portion 410. The wave source 420 may include all kinds of source devices capable of generating waves, for example, may be a laser irradiating light of a certain wavelength band. In order to irradiate waves to a plurality of samples by using the wave source 420, the sample property detecting apparatus 400 according to the embodiment may include the wave path changer 421. In other words, the wave is not directly irradiated onto the samples S from the wave source 420, but may be irradiated to the samples S via the wave path changer 421.

The wave from the wave source 420 may be incident to the wave path changer 421. The wave path changer 421 may include a micro-mirror. The wave path changer 421 includes a reflective surface in order to reflect the incident wave towards the plurality of samples S. The reflective surface is shown as a flat surface having no refractive power, but the present disclosure is not limited thereto. The wave path changer 421 may be minutely operated by a driving controller (not shown). As another embodiment, the wave path changer 421 may be minutely operated by the controller 440, and accordingly, the wave may be irradiated to each of the plurality of samples S. The micro-mirror included in the wave path changer 421 may include various structures, in which a mechanical displacement of the reflective surface may occur according to an electrical controlling, for example, may include a micro electromechanical system (MEMS) mirror, a digital micromirror device (DMD), etc. that are well known. The wave path changer 421 is shown to have one micro-mirror, but is not limited thereto, that is, may include a structure in which a plurality of micro-mirrors are arranged two-dimensionally.

In addition, the wave path changer 421 may further include a mirror 422 arranged on a wave path, in order to constantly adjust an angle of the wave irradiated to the sample arranging portions 410. That is, when the wave is irradiated to the plurality of sample arranging portions 410 by using the micro-mirror in the wave path changer 421, an incident angle of the wave may vary depending on a location of each sample arranging portion 410. Accordingly, a degree of multiple-scattering in the sample S may also vary according to the location of each of the plurality of sample arranging portions 410, and thus it is difficult to precisely perform the comparison. Thus, the mirror 422 may be further arranged so as to adjust the angles of the wave incident to the sample arranging portions 410 to be constant. Although the mirror 422 arranged above the first sample arranging portion 410-1 is only shown in the drawing for convenience of description, the mirror may be arranged above each sample arranging portion 410 to adjust the angle of the wave irradiated to each sample arranging portion 410.

Referring to FIGS. 47 and 48, the multiple scattering amplifier 450 may at least partially reflect the wave towards the sample S, wherein the wave is multiple-scattered and emitted from the sample S, in order to increase the number of multiple scattering in the sample S. The multiple scattering amplifier 450 may include a multiple scattering material. For example, the multiple scattering material includes titanium oxide ($TiO_2$), and the multiple scattering amplifier 450 may reflect at least some of the wave incident thereto. The multiple scattering amplifier 450 is arranged adjacent to the sample S, and thus, the waves multiple-scattered and emitted from the sample S may reciprocate at least once between the sample S and the multiple scattering amplifier 450.

The multiple scattering amplifier 450 may include a first multiple scattering amplifier 451 and a second multiple scattering amplifier 453. The first multiple scattering amplifier 451 is arranged between the sample arranging portion 410 and the wave path changer 421 to overlap with the sample arranging portion 410. As shown in the drawings, according to the present embodiment including the plurality of sample arranging portions 410, a plurality of first multiple scattering amplifiers 451 may be arranged on the plurality of sample arranging portions 410, and may be detachable to place the sample S in the sample arranging portion 410. As another embodiment, the first multiple scattering amplifier 451 may have a structure entirely covering the sample array portion 410A, and may have regions including the multiple scattering materials at locations corresponding to the plurality of sample arranging portions 410. Likewise, the first multiple scattering amplifier 451 according to another embodiment may be a lid type in order to inject the sample S into the sample arranging portion 410.

The second multiple scattering amplifier 453 may be arranged between the sample arranging portion 410 and the detector 430. The second multiple scattering amplifier 453 may be arranged to overlap with each of the plurality of sample arranging portions 410. The second multiple scattering amplifier 453 may be separately provided between the sample arranging portion 410 and the detector 430, but according to another embodiment, the second multiple scattering amplifier 453 may be integrally provided with the sample array portion 410A when the sample array portion 410A includes the multiple scattering material on overlapping regions with the sample arranging portions 410. Otherwise, the second multiple scattering amplifier 453 may be provided as one plate arranged entirely on the sample array portion 410A. In this case, the second multiple scattering amplifier 453 may only include the multiple scattering material in the regions corresponding to the sample arranging portions 410, and may not include a material that does not transmit the wave in remaining regions in order to reduce interferences of the waves scattered from the adjacent sample arranging portions 410.

The detector 430 may detect the laser speckle that is generated by the multiple scattering of the irradiated wave due to the sample S at every predetermined time point. Here, the time point may denote one instant during continuous flow of time, and time points may be set in advance with constant time intervals therebetween, but is not limited thereto, that is, may be set in advance with an arbitrary time interval. The detector 430 may include a sensing unit corresponding to the kind of the wave source 420, for example, a CCD camera that is an imaging device in a case where a light source of a visible ray wavelength band is used. The detector 430 may detect the laser speckle at a first time point at least, and may detect the laser speckle at a second time point, and then, may provide the controller 440 with the detected laser speckles.

The controller 440 obtains temporal correlation by using the detected laser speckles, and may estimate the existence of the microbes or concentration of the microbes in the sample S based on the temporal correlation. The controller 440 may estimate the existence of microbe or concentration of the microbe in each of the plurality of samples S accommodated in the plurality of sample arranging portions 410. Here, the controller 440 may electrically control the reflective surface of the wave path changer 421 to irradiate the waves after changing paths of the waves to the plurality of sample arranging portions 410 at every predetermined time point. The controller 440 may obtain a temporal correlation by classifying laser speckle images detected by the detector 430 in association with the timing of controlling the wave path changer 421. Therefore, the controller 440 may estimate the existence of microbe or concentration of the microbe in each of the plurality of samples S accommodated in the plurality of sample arranging portions 410, even by using one detector 430.

As described above, the sample property detecting apparatus 400 according to the embodiment may rapidly detect existence of microbe or concentration of the microbe in the plurality of samples S accommodated in the plurality of sample arranging portions 410 by using the wave path changer 421.

Figure 49:
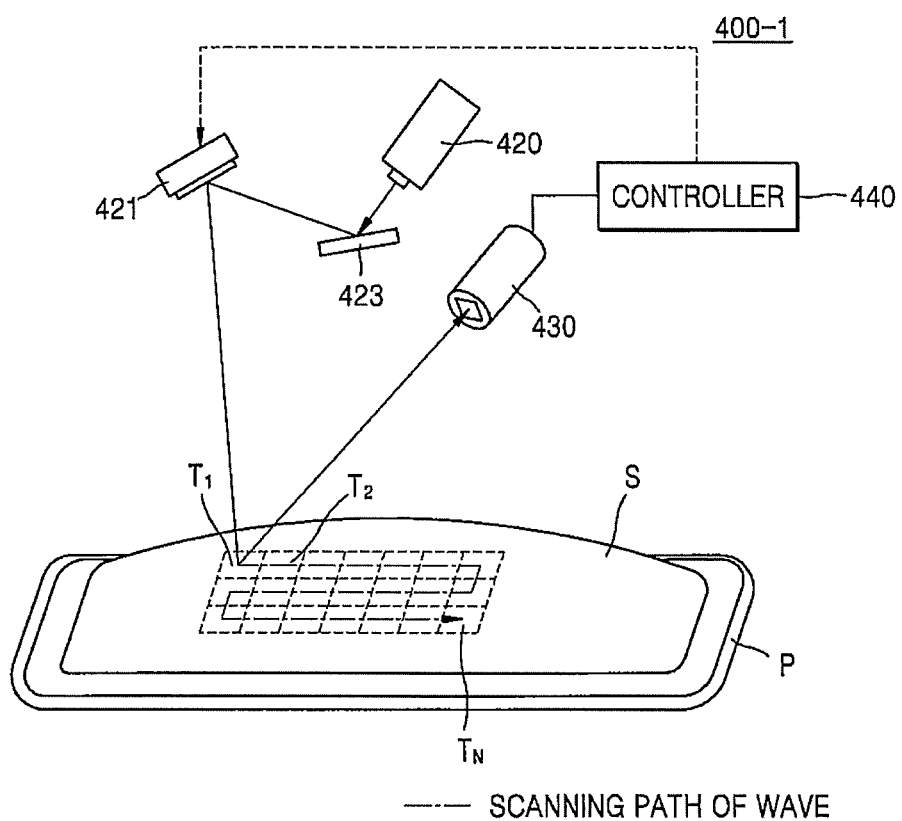
FIGS. 49 and 50 are schematic diagrams of another examples of the sample property detecting apparatus according to the embodiment.
Figure 50:
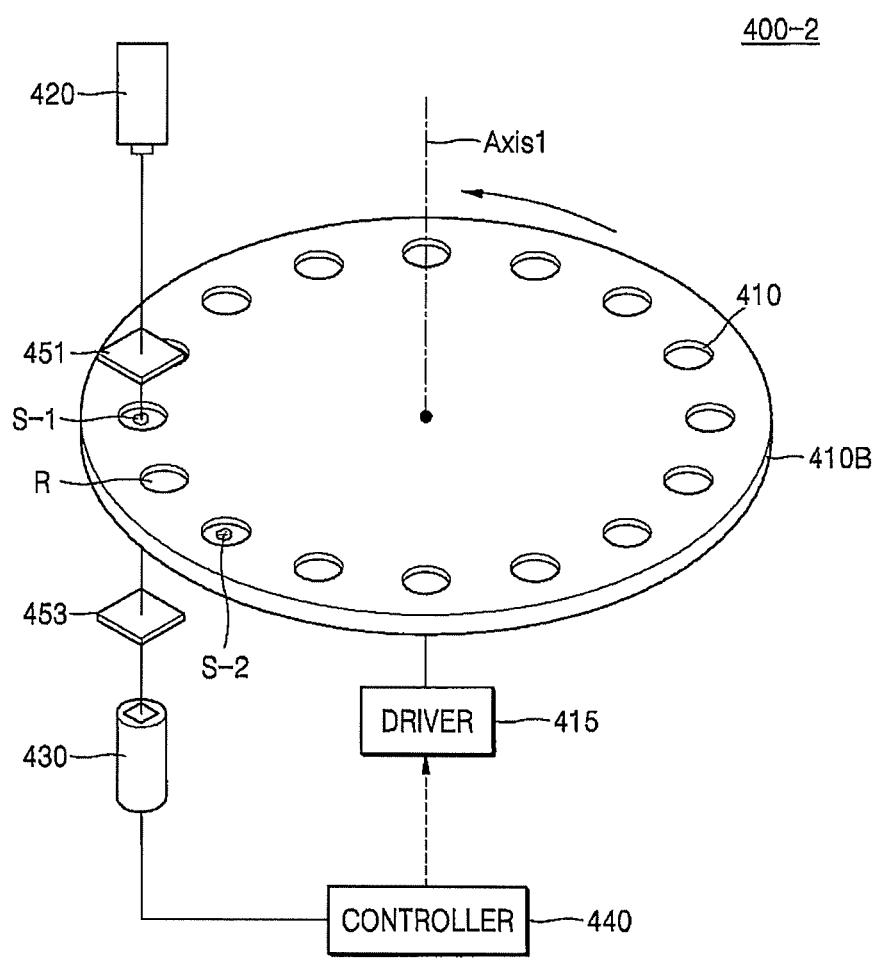

FIGS. 49 and 50 are schematic diagrams of another examples of the sample property detecting apparatus according to the embodiment.

Referring to FIG. 49, a sample property detecting apparatus 400-1 may include the wave source 420, the wave path changer 421, the detector 430, and the controller 440. The sample property detecting apparatus 400-1 according to the embodiment may estimate and compare existence of microbe or concentration of the microbe in each of regions that are obtained by partitioning the sample S. For example, it is necessary to identify the existence of the microbes such as germs with respect to food such as wrapped beef in the wrapped state. Here, the sample property detecting apparatus 400-1 including the wave path changer 421 sequentially irradiates the wave from the wave source 420 along with partitioned regions T1, T2, . . . , TN of the sample S, and then detects existence of the microbe or concentration of the microbe in each region of the sample S.

The sample property detecting apparatus 400-1 may be provided as a reflective optical system in order to detect the microbe in the sample S such as food. Here, the sample property detecting apparatus 400-1 may further include a mirror 423 for making the wave irradiated from the wave source 420 incident to the wave path changer 421. In the drawings, one mirror 423 is shown, but an additional lens or mirror may be further provided to change the wave path. As another embodiment, the sample property detecting apparatus 400-1 may be provided as a transmission type optical system. Here, the sample S may be food wrapped by a transparent wrapper.

In addition, the sample property detecting apparatus 400-1 may further include a multiple scattering amplifier (not shown) according to a kind of medium in the sample S. For example, if the sample has a medium having dense tissues such as beef, the multiple scattering may sufficiently occur without using the multiple scattering amplifier, and then, the microbe may be detected. However, with respect to different kinds of media, the multiple scattering amplifier (not shown) may be further provided to detect existence of microbe in the sample S, and thus, the analyzing may be precisely performed.

The controller 440 may obtain a temporal correlation by classifying laser speckle images detected by the detector 430 in association with the timing of controlling the wave path changer 421. As such, the controller 440 may detect whether microbe exists in each region by using the detected laser speckle images. Also, the controller 440 may control a scanning path (dashed-dot line) of the wave path changer 421, and thus may obtain a spatial correlation of the laser speckles. That is, the sample property detecting apparatus 400-1 according to another embodiment may obtain the spatial correlation, as well as the temporal correlation, may perform mapping of the existence of the microbes or concentration of the microbes in the sample.

Referring to FIG. 50, a sample property detecting apparatus 400-2 according to another embodiment may include a rotary array portion 410B including the plurality of sample arranging portions 410, and may also include the wave source 420, the detector 430, the controller 440, and the first and second multiple scattering amplifiers 451 and 453. Here, the optical system including the wave source 420, the detector 430, and the multiple scattering amplifiers 451 and 453 may measure the plurality of samples accommodated in the plurality of sample arranging portions 410 in a fixed state, because the rotary array portion 410B rotates.

The rotary array portion 410B may include a driver 415 that drives the rotary array portion 410B at a rotating speed that is set in advance. In the rotary array portion 420B, the plurality of sample arranging portions 410 may be arranged being spaced apart from one another with a predetermined interval in a circumferential direction. The plurality of sample arranging portions 410 in the rotary array portion 410B are spaced apart one another with a constant interval and rotate at a constant rotating speed, and thus, the existence of the microbe or the concentration of the microbe in the samples accommodated in the sample arranging portions 410 may be detected by using the fixed wave source 420 and the detector 430. The rotary array portion 410B may rotate about a center axis Axis1 passing through a center O thereof, and may be minutely operated not to tilt with respect to the center axis Axis1 while rotating. Tilting of the rotary array portion 410B may apply as noise in detecting the laser speckles. The controller 440 may rotate the rotary array portion 410B by controlling the driver 415, and at this time, the controller 440 may classify and analyze laser speckles detected from the sample arranging portions 410 according to the samples.

In addition, the rotary array portion 410B may include a reference sample arranging portion R among the sample arranging portions 410. The reference sample arranging portion R may be the same as the sample arranging portions 410, but the sample S may not be accommodated in the reference sample arranging portion R. By measuring a reference laser speckle from the reference sample arranging portion R, noise that may occur during the rotation of the rotary array portion 410B may be removed and the laser speckle may be accurately detected.

The multiple scattering amplifier may include the first multiple scattering amplifier 451 and the second multiple scattering amplifier 453. The first multiple scattering amplifier 451 may be arranged between the wave source 420 and the sample arranging portion 410. The first multiple scattering amplifier 451 may be arranged above the sample arranging portion 410 to which the wave is irradiated from the wave source 420, and prevents the wave from being irradiated to other sample arranging portions 410 to reduce noise. Also, the second multiple scattering amplifier 453 may be arranged between the sample arranging portion 410 and the detector 430, and likewise, may be located to correspond to the sample arranging portion 410 that is measured in order to only detect the wave multiple-scattered from the sample arranging portion 410. In the drawings, the first multiple scattering amplifier 451 and the second multiple scattering amplifier 453 are spaced apart from the sample arranging portions 410, but are not limited thereto. As another embodiment, the first multiple scattering amplifier 451 and the second multiple scattering amplifier 453 may be fixedly located on upper and lower portions of each sample arranging portion 410.

Hereinafter, a sample property detecting apparatus according to another embodiment will be described below with reference to FIGS. 51 to 56.

A laser speckle denotes irregular pattern that is generated by interference effect of reflected light when light having coherency is irradiated to a scatter. According to the technical concept of the present disclosure, pattern abnormality of a structure arranged on a substrate may be checked by analyzing the laser speckle.

Figure 51:
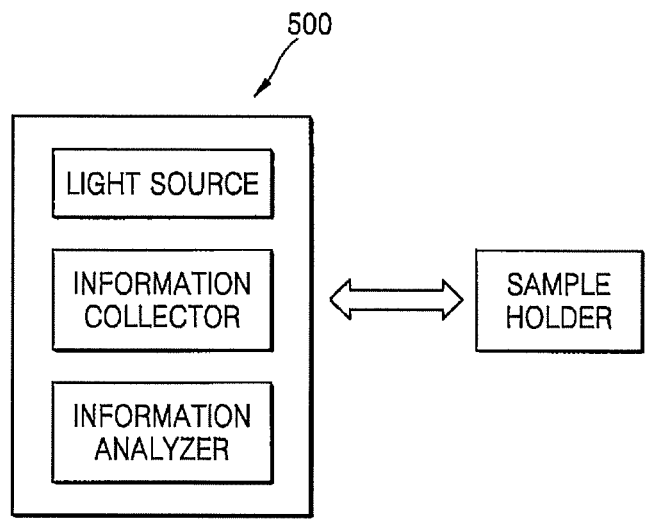
FIG. 51 is a diagram showing a sample property detecting apparatus according to an embodiment.

FIG. 51 is a diagram showing a sample property detecting apparatus according to an embodiment. Referring to FIG. 51, the sample property detecting apparatus 500 may include a light source irradiating laser beam, a sample holder supporting a sample, an information collector for collecting laser speckle information generated when light incident to the sample is multiple-scattered, and an information analyzer for analyzing collected information and outputting analyzing result to a user. Here, the light source may correspond to the wave source according to previous embodiments, the information collector may correspond to the detector in the previous embodiments, and the information analyzer may correspond to the controller in the previous embodiments.

The light source generates and irradiates laser to the sample, and one light source may be provided or two or more light sources irradiating light of different wavelengths may be provided.

Figure 52:
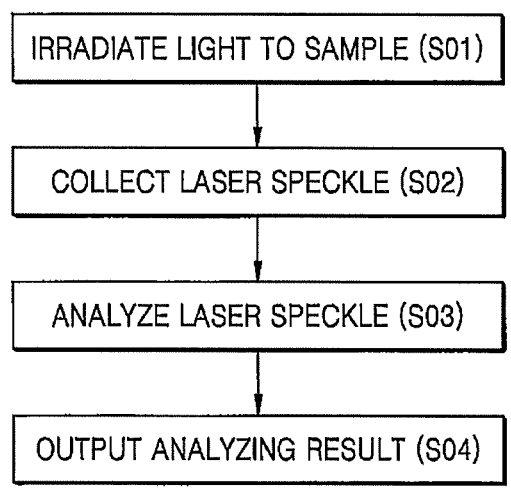
FIG. 52 is a diagram illustrating a testing method according to an embodiment.

FIG. 52 illustrates a testing method according to an embodiment. Referring to FIG. 52, the laser is irradiated to a sample supported by the sample holder (S01). Next, the information collector collects a laser speckle formed by interaction between the irradiated laser and the sample (S02). Information about the laser speckle collected by the information collector is analyzed by the information analyzer and an analyzing result is output to the user (S03).

The information collector may be, for example, a camera, and the optical system including the light source and the camera may be configured in various types such as a reflective type and a transmission type as shown in FIGS. 4A to 4C. FIG. 53 shows a multi-layered metal wiring structure of a semiconductor device as an example of the sample. A first insulating layer 64 is arranged between a first metal wiring 61 and a second metal wiring 62, and a second insulating layer 65 is arranged on the second metal wiring 62.

The first and second insulating layers 64 and 65 may include silicon oxide (SiO2), but may include any kind of insulating material that is transparent to transmit light. The first and second metal wirings 61 and 62 may include, for example, aluminum, tungsten, copper, etc.

Therefore, when laser is irradiated to the sample, some of the laser that has transmitted through the second insulating layer 65 that may transmit light is reflected by the second metal wiring 62, but some other transmits through the first insulating layer 64. Again, some of the laser is reflected or scattered in a via 63 or a structure in which the first metal wiring 61 is provided and then transmits through the first insulating layer 64 and the second insulating layer 65 to form the laser speckle. Therefore, the laser speckle pattern may be determined according to a shape of the structure (metal wiring, via, insulating layer, etc.) in the sample, and the laser speckle pattern may also change according to the change in the structure. Hereinafter, a method of analyzing a speckle pattern using the change in the sample structure will be described below with reference to FIGS. 53A to 53C.

Figure 53A:
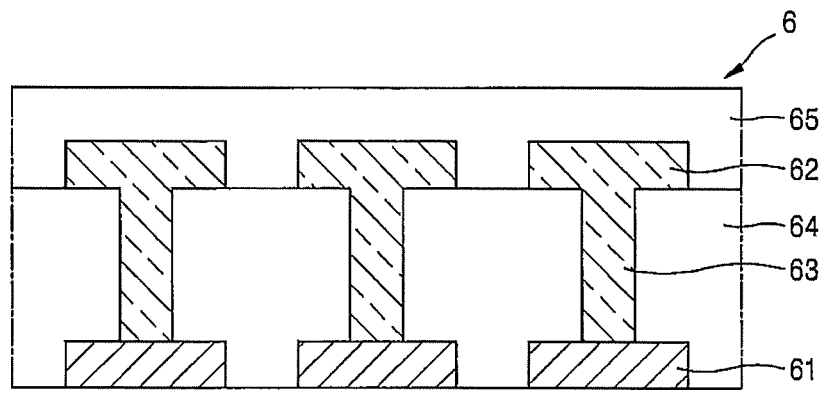
FIG. 53A, FIG. 53B, and FIG. 53C are diagrams of a multi-layered metal wiring structure of a semiconductor device as an example of the sample.
Figure 53B:
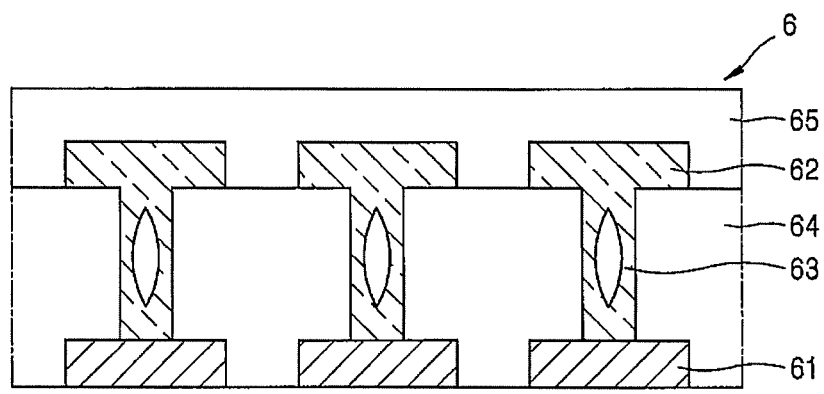
Figure 53C:
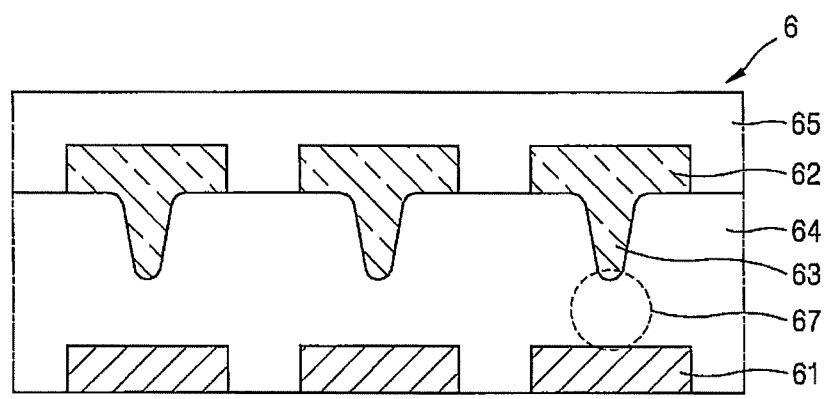

FIG. 53A shows that processes are normally performed, FIG. 53B shows that a through hole 610 is formed in the via, and FIG. 53C shows that a contact penetrating through an insulator is not formed.

The above sample is mounted in the sample holder and the laser is irradiated to the sample, and then, information about the laser speckle scattered from the sample is collected. The collected information is analyzed by the information analyzer. The information analyzer is connected to a DB in which laser speckle information of a standard sample, that is, a case where the processes are normally performed as in FIG. 53A. The information analyzer compares the collected laser speckle information with the laser speckle information of the standard sample stored in advance in the DB to calculate a difference value of the speckle patterns. When the difference value is equal to or less than a reference set in advance, it is interpreted that the analyzed sample has the same structure as the standard sample, and thus, it may be determined that the processes are normally performed.

However, as shown in FIG. 53B or FIG. 53C, the processes are abnormally performed and an abnormal region exists in the pattern, the difference between the collected laser speckle information and the laser speckle information of the standard sample may exceeds the reference value set in advance, and thus, it is determined that the processes are abnormally performed.

Figure 54A:
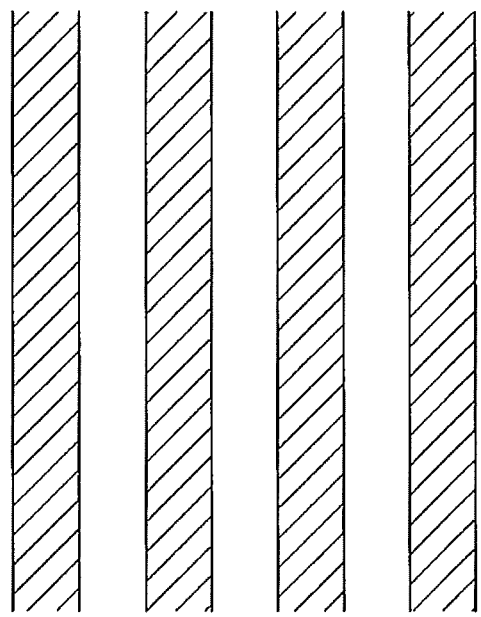
FIGS. 54A and 54B show an example of identifying a change in a line width of the metal wiring by analyzing laser speckle.
Figure 54B:
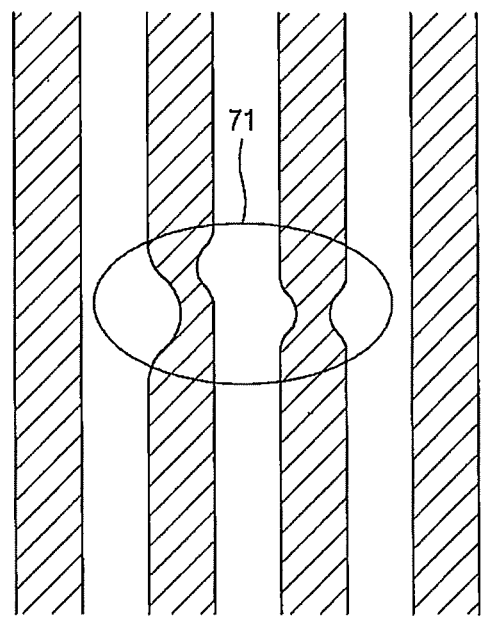

FIGS. 54A and 54B shows an example of identifying a change in a line width of the metal wiring by analyzing laser speckle. As shown in FIG. 54A, a normal line width may represent that the difference between the sample and the standard sample may be equal to or less than a reference set in advance. However, as shown in FIGS. 54A and 54B, when there is a region 71 having an abnormal line width, the difference from the standard sample is increased, and thus, it may be determined that the processes are abnormally performed.

As another example, abnormality of an active area formed in a silicon substrate by an ion implantation may be checked in the same manner as above.

Figure 55:
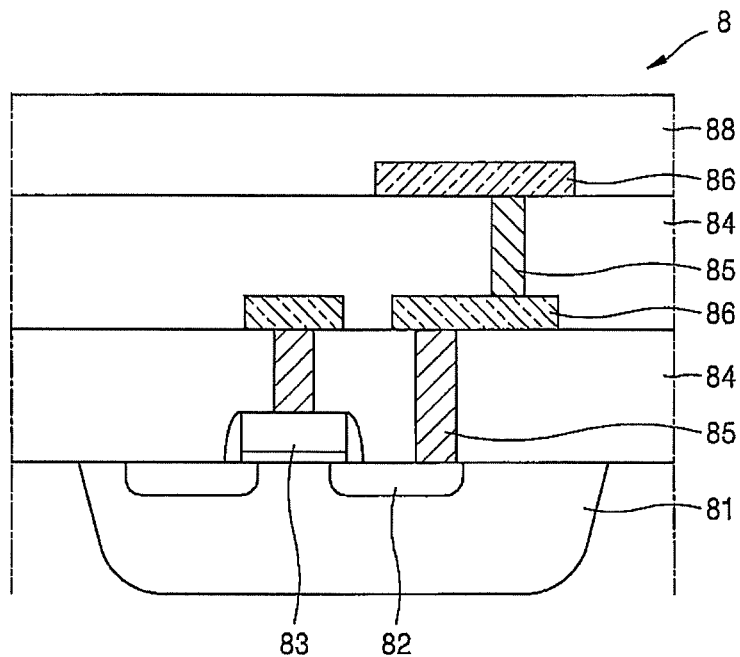
FIG. 55 is a diagram of an example in which a plurality of pattern regions are arranged on a silicon wafer.

The sample property detecting apparatus according to another embodiment may perform a function of determining whether there is the pattern shape with respect to all of a plurality of pattern regions arranged in a silicon wafer by sequentially checking the plurality of pattern regions provided in the silicon wafer. FIG. 55 shows an example in which a plurality of pattern regions are arranged on a silicon wafer. In this case, a pattern region is a region that is partitioned to be separated by sawing when the processes are finished and become one final device.

Figure 56:
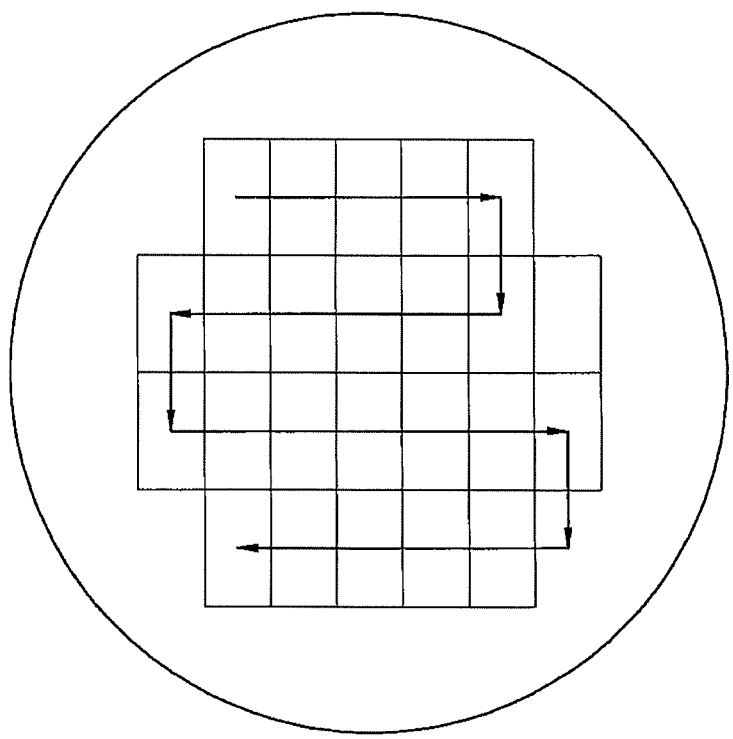
FIG. 56 is a diagram showing an example of testing patterns according to a test region by using the sample property detecting apparatus of FIG. 51.

FIG. 56 is a diagram showing an example of testing patterns according to a test region by using the sample property detecting apparatus of FIG. 51. When the sample property detecting apparatus according to the embodiment is used, the laser is sequentially irradiated to the plurality of pattern regions, for example, from a left uppermost pattern region as denoted by an arrow of FIG. 56, and the information collector collects and stores laser speckle information from each of the pattern regions in the DB. The information analyzer analyzes the laser speckle information of each pattern region stored in the DB to perform a statistical analyzing of an average value and a standard deviation in the entire pattern regions. In this case, the pattern region having the laser speckle information exceeding greatly average value may be interpreted to have different structure from the other pattern regions, and it may be determined that the processes are abnormally performed. Therefore, when information about the pattern region that is abnormally processed is output, the user may obtain information about the abnormal pattern region without locally cutting the silicon wafer.

The present disclosure may be applied to various fields utilizing the laser speckle, for example, a non-invasive blood flow measurement using the laser speckle, a laser speckle contrast imaging, a non-invasive blood vessel checking, a personal authentication using the blood flow measurement, etc. Also, the present disclosure may be also applied in a manufacturing inspection field such as a mirror-surface machining inspection, an isolation test of a multi-layered film, etc. Also, the present disclosure may be applied in such fields as a location tracking of a moving object by using a binary imaging, a rotation sensor using an optical encoder, etc.

While the present disclosure has been particularly shown and described with reference to preferred embodiments thereof, it will be understood by those skilled in the art that various changes in form and details may be made therein without departing from the spirit and scope of the present disclosure as defined by the appended claims. The preferred embodiments should be considered in descriptive sense only and not for purposes of limitation. Therefore, the scope of the present disclosure is defined not by the detailed description of the disclosure but by the appended claims, and all differences within the scope will be construed as being included in the present disclosure.

INDUSTRIAL APPLICABILITY

According to an aspect of the present disclosure, a sample property detecting apparatus using a chaotic wave sensor is provided.

What is claimed is:
1. An entity discrimination apparatus comprising:
a sample arranging unit configured to accommodate a sample taken from a target entity;
an environmental chamber configured to accommodate the sample arranging portion therein and change an environmental condition surrounding the sample;
a wave source configured to irradiate a wave towards the sample in the sample arranging portion;

one or more detectors configured to detect a laser speckle that is generated by multiple scattering of the irradiated wave due to the sample, at every predetermined time point; and a controller configured to estimate concentrations of microbes in the sample by using the detected laser speckle before and after the environmental condition is changed, and discriminate the target entity from among a plurality of entities by using a difference between the estimated concentrations of the microbes before and after the environmental condition is changed, and wherein the controller comprises:

an average concentration estimator configured to obtain a temporal correlation of the detected laser speckle by using the detected laser speckle, and estimate an average concentration of one or more kinds of microbes included in the sample based on the obtained temporal correlation; and an identifier configured to generate discrimination data by calculating a variation rate of the average concentration of the microbes according to the change in the environmental condition, and discriminate the target entity by using the discrimination data.

2. The entity discrimination apparatus of claim 1, further comprising a data storage in which reference data about the variation rate of the average concentration of the microbes according to the change in the environmental condition is stored in advance, wherein the identifier is further configured to discriminate the target entity from among the plurality of entities by comparing the discrimination data and the reference data.

3. The entity discrimination apparatus of claim 2, wherein the controller is further configured to, when the target entity is acknowledged in advance, determine a health condition of the target entity by comparing the discrimination data of the target entity and the reference data.

4. The entity discrimination apparatus of claim 1, wherein the wave source is arranged on an outer portion of the environmental chamber.

5. The entity discrimination apparatus of claim 4, wherein a surface of the environmental chamber on a path through which the wave is irradiated includes a transparent material.

6. The entity discrimination apparatus of claim 4, wherein a surface of the environmental chamber on a path through which the wave is irradiated includes a diffusion material for diffusing the wave.

7. The entity discrimination apparatus of claim 1, wherein the environmental chamber is configured such that at least one of a temperature, humidity, pressure, and a magnetic field is changeable.

* * * * *